United States Patent
Voziyanov

(10) Patent No.: US 12,024,726 B2
(45) Date of Patent: Jul. 2, 2024

(54) Flp-TAL RECOMBINASES

(71) Applicant: Louisiana Tech Research Corporation, Ruston, LA (US)

(72) Inventor: Yuri Voziyanov, Ruston, LA (US)

(*) Notice: Subject to any disclaimer, the term of this patent is extended or adjusted under 35 U.S.C. 154(b) by 0 days.

(21) Appl. No.: 17/943,127

(22) Filed: Sep. 12, 2022

(65) Prior Publication Data

US 2023/0383267 A1    Nov. 30, 2023

Related U.S. Application Data

(62) Division of application No. 16/679,201, filed on Nov. 9, 2019, now Pat. No. 11,473,066.

(60) Provisional application No. 62/758,512, filed on Nov. 9, 2018.

(51) Int. Cl.
*C12N 9/12*     (2006.01)
*C12N 15/90*    (2006.01)

(52) U.S. Cl.
CPC ......... *C12N 9/1241* (2013.01); *C12N 15/907* (2013.01); *C07K 2319/09* (2013.01); *C07K 2319/80* (2013.01)

(58) Field of Classification Search
None
See application file for complete search history.

(56) References Cited

PUBLICATIONS

Chen et al. (Crystal Structure of a Flp Recombinase-Holliday Junction Complex: Assembly of an Active Oligomer by Helix Swapping, Molecular Cell, vol. 6, 885-897, Oct. 2000).*

* cited by examiner

*Primary Examiner* — Suzanne M Noakes
*Assistant Examiner* — Jae W Lee
(74) *Attorney, Agent, or Firm* — Elliot C. Mendelson; Mendelson IP

(57) ABSTRACT

The present invention provides chimeric Flp-TAL recombinases, as well as nucleic acids, and methods for the use of the chimeric Flp-TAL recombinases for site-specific alteration of a target sequence in cells.

2 Claims, 18 Drawing Sheets
Specification includes a Sequence Listing.

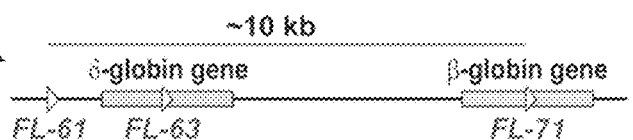

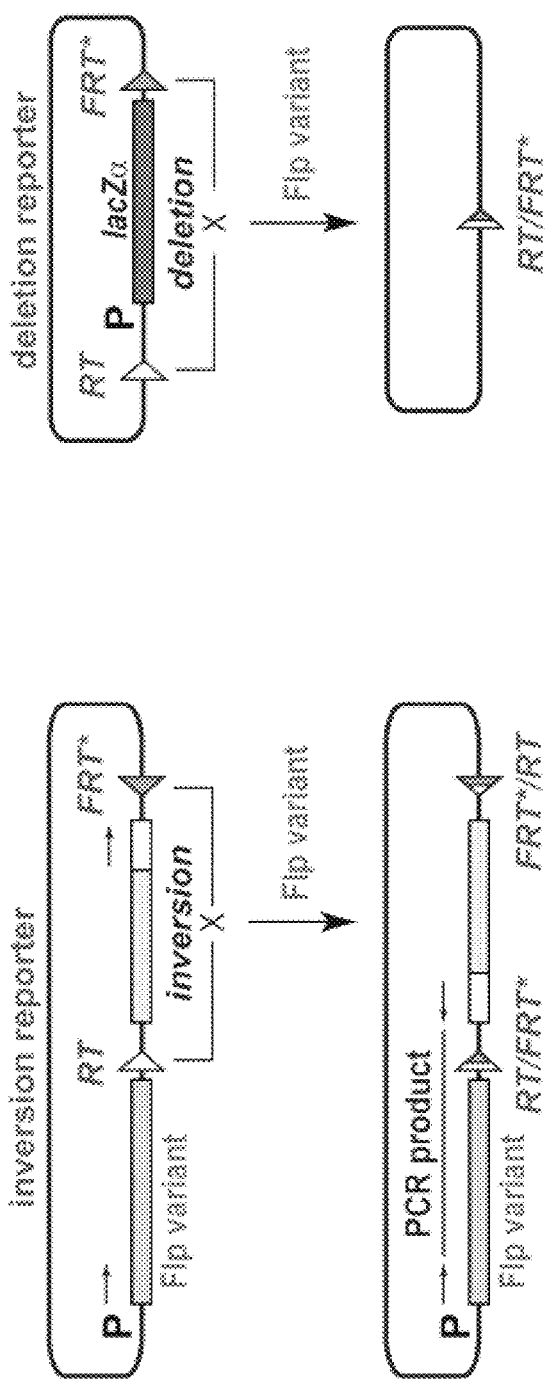

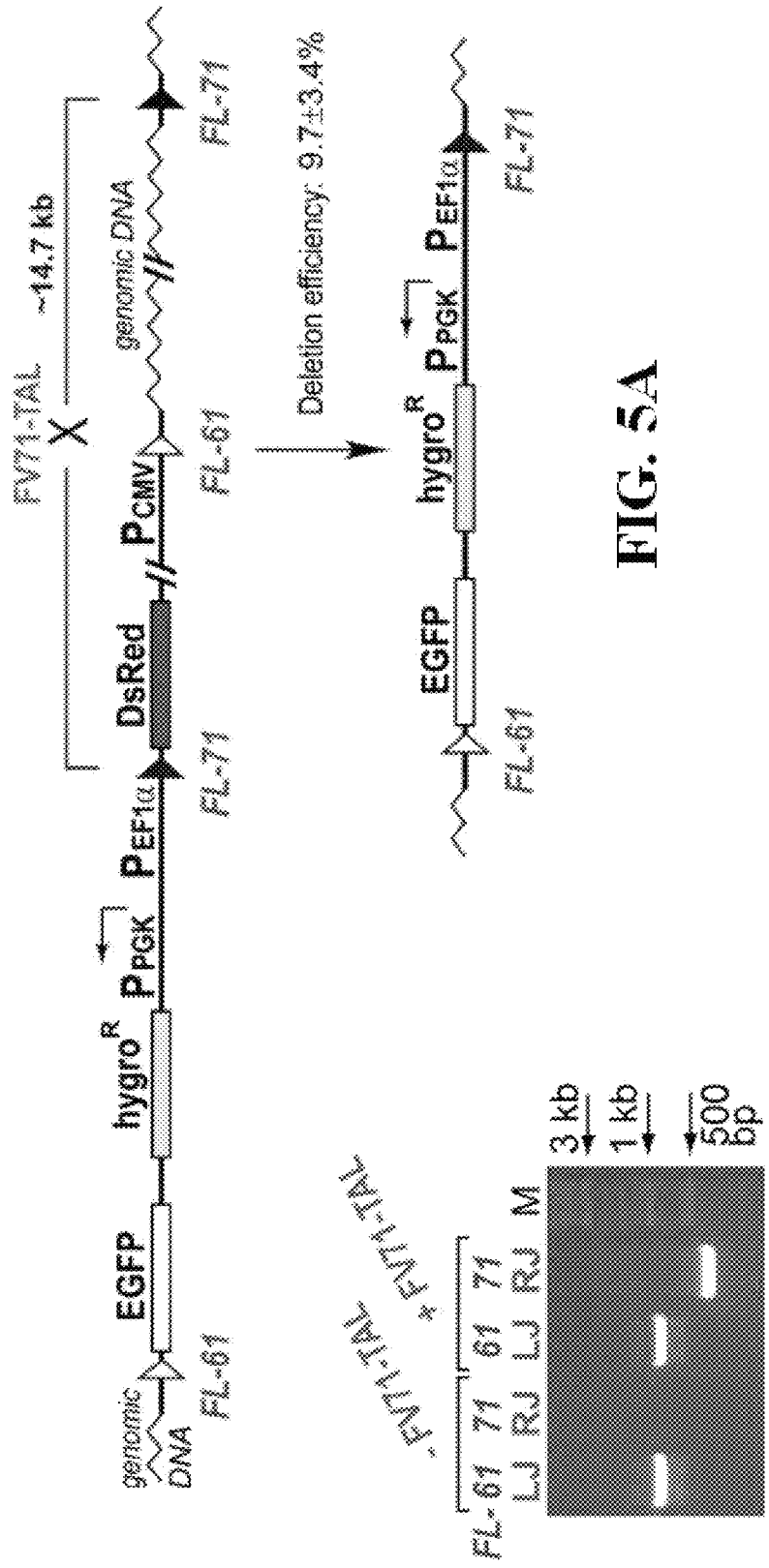
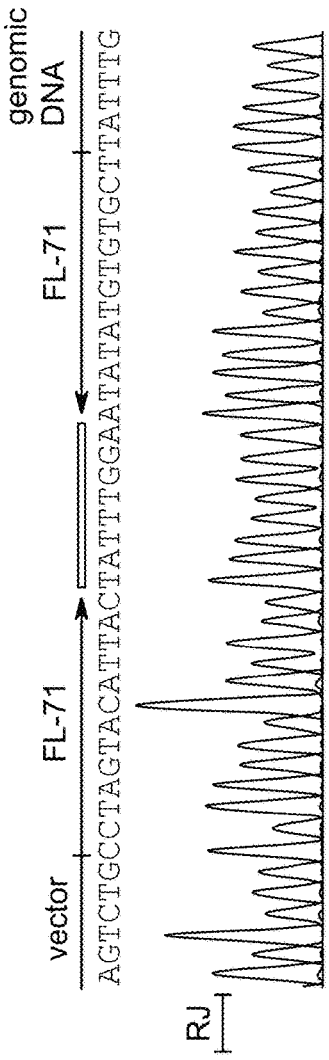
FIG. 5A
FIG. 5B
FIG. 5C

FRT_TAL-FL61 (outer FRT; the EM-7 promoter is located before the recombination site)

CMV promoter
ATCGGCATAGTATATCGGCATAGTATAATACGACAAGGTGAGGAACTAAACC
ACAATCAAATTATCATAACAACTT GAAGTTCCTATAC TgataAtA
GAAatGGcAtTgt ACTTTCCACTACTGCAATAGAAGTCTAGT
CTTC cctttgaaaaacacgatgataatatggccacaacc
vector FRT_TAL-FL63 (outer FRT; the EM-7 promoter is located before the recombination site)

CMV promoter
ATCGGCATAGTATATCGGCATAGTATAATACGACAAGGTGAGGAACTAAACC
ACAATCAAATTATCATAACAACTT GAAGTTCCTATAC TGCACTTA GAATAATCCTTTT
GCTTTCTACATCCTATGAACAGG
CTTC cctttgaaaaacacgatgataatatggccacaacc
vector FRT_TAL-FL71 (outer FRT site; the lacIQ promoter is located before the recombination site)

EF1a promoter
gactcactatagggagacccaagctggctagg
tggtgcaaaacttttcgcggtatggcatgatagcgcccggaagagagtcaattcagg
GAGATACATTAACTAACTAAAAAAAACTTTACACTT cctagTaCatTAC TaTtTgGA
GTATAGGAACTTC TATTCAATACATAAATCCCACTAATAAT
vector

FIG. 8

```
MDLRTLGYSQQQQEKIKPKVRSTVAQHHEALVGHGFTHAHIVALSQHPAALGTVAVTYQHIIALPEAT
HEDIVGVGKQWSGARALEALLTDAGELRGPPLQLDTGQLVKIARRGGVTAMEAVHASRNALTGAPLNLTP
DQVVAIASNNGGKQALETVQRLLPVLCQDHGLTPDQVVAIASNGGKQALETVQRLLPVLCQDHGLTPDQ
VVAIASNIGGKQALETVQRLLPVLCQDHGLTPDQVVAIASNGGKQALETVQRLLPVLCQDHGLTPDQVV
AIASNIGGKQALETVQRLLPVLCQDHGLTPDQVVAIASNGGKQALETVQRLLPVLCQDHGLTPDQVVAI
ASNGGGKQALETVQRLLPVLCQDHGLTPDQVVAIASNGGKQALETVQRLLPVLCQDHGLTPDQVVAIAS
NIGGKQALETVQRLLPVLCQDHGLTPDQVVAIASNGGKQALETVQRLLPVLCQDHGLTPDQVVAIASNI
GGKQALETVQRLLPVLCQDHGLTPDQVVAIASNGGKQALETVQRLLPVLCQDHGLTPDQVVAIASNGGG
KQALETVQRLLPVLCQDHGLTPDQVVAIASHGGKQALETVQRLLPVLCQDHGLTPDQVVAIASNGGGKQ
ALETVQRLLPVLCQDHGLTPDQVVAIASHGGKQALETVQRLLPVLCQDHGLTPDQVVAIASHDGGKQAL
ETVQRLLPVLCQDHGLTPDQVVAIASHGGKQALESIVAQLSRPDPALAALTNDHLVALACLGGRPAMDA
VKKGLPHAPELIRRVNRRIGERTSHRVADYAQVVRVLEFFQCHSHPAYAFDEAMTQFGMS
```

FIG. 9

>71-18_TAL

MSQFDILCKTPPEVLVPQFVEPFERPSGEKIASCTAKLIYLCRVVTHDGAAIKPSTFVNYNSIIGN
SLSFDIVNKSLQFKYKTQKATILEASLKKLIIAMEFTIIPYNGQKHQPDITDIVSSLQLQFESPEK
ADKGNSHSKKMLFALLSECESIWEITEKILNCFEYTSPCTKFALYQFLFLATFINCGRFSDIKNV
DFKSFKLVQNKYLGEIIQCLVTETKTSVSRGIYFFSARGRIDPLVYLDEFLRNCEPVLKRVNKTON
SSSNKQEYQLLKDNLVRSYNKALKKSAPYPFFAIKNGFRSHIGRHLMTSFLSMKGLTELTNVVGNW
SDKRASAVARTTYTHQITAIPDHYFALVSRYYAYDPISKEMIALKDETNPIEEWQHIEQLKGSAEG
SIRYPAMNGIISQEVLDYLSSYINRRIGT[L6 linker][delta 152]LTPDQVVAIASNNGGKQAL
ETVQRLLPVLCQDHGLTPDQVVAIASHDGGKQALETVQRLLPVLCQDHGLTPDQVVAIASNIGGKQ
ALETVQRLLPVLCQDHGLTPDQVVAIASNGGGKQALETVQRLLPVLCQDHGLTPDQVVAIASNIGG
KQALETVQRLLPVLCQDHGLTPDQVVAIASNGGGKQALETVQRLLPVLCQDHGLTPDQVVAIASNG
GGKQALETVQRLLPVLCQDHGLTPDQVVAIASHDGGKQALETVQRLLPVLCQDHGLTPDQVVAIAS
NIGGKQALETVQRLLPVLCQDHGLTPDQVVAIASNGGGKQALETVQRLLPVLCQDHGLTPDQVVAI
ASNIGGKQALETVQRLLPVLCQDHGLTPDQVVAIASNIGGKQALETVQRLLPVLCQDHGLTPDQVV
AIASNGGGKQALETVQRLLPVLCQDHGLTPDQVVAIASHDGGKQALETVQRLLPVLCQDHGLTPDQ
VVAIASNGGGKQALETVQRLLPVLCQDHGLTPDQVVAIASHDGGKQALETVQRLLPVLCQDHGLTP
DQVVAIASHDGGKQALETVQRLLPVLCQDHGLTPDQVVAIASHDGGKQALE[+95][SV40 NLS]G[...]

Color coding:
MSQFDILC... - Flp
GT and G - short connectors
[highlighted] - L6 linker
[highlighted] and [highlighted] - delta 152 and +95 sections of the TAL module
LTPDQVVAI... - TAL DBD unit (in this case 18 repeats)
[highlighted] - SV40 NLS

FIG. 10

>TAL/L24-TAL/R15
GTAACTTAAAAAAAAACTTTACACAGTCTG cctagtacattAC TaTtTgGA
gTATAGgAACTTg TATTTGCATATTCATAATCT >TAL/L18-TAL/R15
TAAAAAAAAACTTTACACAGTCTG cctagtacattAC TaTtTgGA gTATAGgAACTTg
TATTTGCATATTCATAATCT >TAL/L15-TAL/R15
AAAAAAACTTTACACAGTCTG cctagtacattAC TaTtTgGA gTATAGgAACTTg
TATTTGCATATTCATAATCT Codes:
- TAL binding sequences
- FL-71 binding sequences
- spacer in FL-71

FIG. 11

\>loxP
ATAACTTCGTATAA TGTATG TTATACGAAGTTAT

\>TAL/L15-TAL/R12_1
AAATAAGAAATTTGTAAA TTcCTTCtgATAA ctagaa ATAgAgGATccagt
TTCTTTTggTAACCTAAA \>TAL/L15-TAL/R15_2
CAATGGAAATAAGAAATTTGTAAA TTcCTTCtgATAA ctagaa ATAgAgGATccagt
TTCTTTTggTAACCTAAATT \>TAL/L15-TAL/R12_2
CAATGGAAATAAGAAATTTGTAAA TTcCTTCtgATAA ctagaa ATAgAgGATccagt
TTCTTTTggTAACCTAAA Codes:
- TAL binding sequences
- LL-69 binding sequences
- spacer in LL-69

FIG. 12

```
>iCreM24/69-TAL
ATGGTGCCCAAGAAGAAGAGGAAAGTCTCCAACCTGCTGACTGTGCACCAAAACCTGCCTGCCCTCCCTGTGG
ATGCCACCTCTGATGAAGTCATGAAGAACCTGATGGACATGTTCAGGGACAGGCAGGCCTTCTCTGAACACAC
CTGGAAGATGCTCCTGTCTGTGTGCAGATCCTGGGCTGCCTGGTGCAAGCTGAACAACAGGAAATGGTTCCCT
GCTGAACCTGAGGATGTGAGGGACTACCTCCTGTACCTGCAAGCCAGAGGCCTGGCTGTGAAGACCATCCAAC
AGCACCTGGGCCAGCTCAACATGCTGCACAGGAGATCTGGCCTGCCTCGCCCTTCTGACTCCAATGCTGTGTC
CCTGGTGATGAGGAGAATCAGAAAGGAGAATGTGGATGCTGGGGAGAGAGCCAAGCAGGCCCTGGCCTTTGAA
CGCACTGACTTTGACCAAGTCAGATCCCTGATGGAGAACTCTGACAGATGCCAGGACATCAGGAACCTGGCCT
TCCTGGGCATTGCCTACAACACCCTGCTGCGCATTGCCGAAATTGCCAGAATCAGAGTGAAGGACATCTCCCG
CACCGATGGTGGGAGAATGCTGATCCACATTGGCAGGACCAAGACCCTGGTGTCCACAGCTGGTGTGGAGAAG
GCCCTGTCCCTGGGGGTTACCAAGCTGGTGGAGAGATGGATCTCTGTGTCTGGTGTGGCTGATGACCCCAACA
ACTACCTGTTCTGCCGGGTCAGAAAGAATGGTGTGGCTGCCCCTTCTGCCACCTCCCAACTGTCCACCCGGGC
CCTGGAAGGGATCTTCGAGGCCACCCACCGCCTGATCTATGGTGCCAAGGATGACTCTGGGCAGAGATACCTG
GCCTGGTCTGGCCACTCTGCCAGAGTGGGTGCTGCCAGGGACATGGCCAGGGCTGGTGTGTCCATCCCTGAAA
TCATGCAGGCTGGTGGCTGGACCAATGTGAACATTGTGATGAACTACATCAGAAACCTGGACTCTGAGACTGG
XXXXXXXXXXXXXXXXXXXXXXXXXXXXXGGTACCGGATCAGGCGGAAGCGGACCGCATACAGCGGCTGCC
CCAGCAGAGTGGGATGAGGCGCAATCGGCTCTGCGTGCAGCCGATGACCCGCCACCCACCGTGCGTGTCGCTG
TCACTGCCGCGCGGCCGCCGCGCGCCAAGCCGGCCCCGCGACGGCGTGCTGCGCAACCCTCCGACGCTTCGCC
GGCCGCGCAGGTGGATCTACGCACGCTCGGCTACAGTCAGCAGCAGCAAGAGAAGATCAAACCGAAAGGTGCG
TTCGACAGTGGCGCAGCACCACGAGGCACTGGTGGGCCATGGGTTTACACACGCGCACATCGTTGCGCTCA
```

Codes:
▓ – end of Cre gene
⋯ – KpnI site
▓ – linker between the Cre and TAL modules
▓ – beginning of the TAL module (delta-117)

FIG. 13

Flp-TAL RECOMBINASES

CROSS-REFERENCE TO RELATED APPLICATION

The application is a DIV of U.S. patent application Ser. No. 16/679,201, filed Nov. 9, 2019, which claims the benefit of U.S. Provisional Application No. 62/758,512, filed Nov. 9, 2018, which is incorporated by reference in its entirety.

FEDERALLY SPONSORED RESEARCH OR DEVELOPMENT

This invention was made with government support under Grant No. R01GM085848 awarded by the National Institutes of Health. The government has certain rights in the invention.

SEQUENCE LISTING

The instant application contains a Sequence Listing which has been submitted in XML format via EFS Web and is hereby incorporated by reference in its entirety. Said XML copy, created Jan. 8, 2023 is named flp-tal_recombinases_sequence_listing.xml and is 107,784 bytes in size.

BACKGROUND OF INVENTION

The relative simplicity, with which target specificity of certain site-specific nucleases can be changed, particularly in the CRISPR/Cas9 and TALEN systems, has made these DNA manipulation enzymes some of the more preferred tools in the field of genome engineering in recent years. Miller J C, et al. (2011) A TALE nuclease architecture for efficient genome editing. Nat Biotechnol 29(2):143-148, Cong L, et al. (2013) Multiplex genome engineering using CRISPR/Cas systems. Science 339(6121):819-823. However, several inherent properties of these site-specific nucleases, which includes the necessity to introduce double strand breaks, the reliance on the endogenous cell DNA repair machinery to process these breaks, and the frequency at which they target unintended locations, limits their utility.

Tyrosine recombinases, such as popular genome engineering tools Flp and Cre, are highly specific for their targets, versatile in performing DNA manipulation reactions, and can be easily regulated. These features, however, are only useful for genome engineering if the native targets for these tyrosine recombinases are pre-introduced into a genome locale of interest. This limits the utility of the naturally occurring enzymes in applications that are aimed to manipulate the genome of previously unmodified cells.

Tyrosine recombinase variants can be evolved that are able to recognize target sequences that vary from the native enzyme's recombination target sequence. Buchholz F & Stewart A F (2001) Alteration of Cre recombinase site specificity by substrate-linked protein evolution. Nat Biotechnol 19(11):1047-1052, Sarkar I, et al. (2007) HIV-1 proviral DNA excision using an evolved recombinase. Science 316(5833):1912-1915, Bolusani S, et al. (2006) Evolution of variants of yeast site-specific recombinase Flp that utilize native genomic sequences as recombination target sites. Nucleic Acids Res 34(18):5259-5269, Shultz J L, et al., (2011) A genome-wide analysis of FRT-like sequences in the human genome. PLoS One 6(3):e18077. The total number of such target-like sequences in a genome can be quite substantial: The human genome, for example, has about 600,000 FRT-like sequences. That is, sequences that have a level of homology to FRT, the native recombination target for Flp recombinase. This number corresponds to one FRT-like sequence per ~5 kb. Shah et al. (2011). Such a density allows DNA manipulation in essentially all genome locales, provided the variants that are evolved to recombine these target-like sequences can bind them in their native chromosomal environment, out-competing other DNA binding proteins, primarily histones.

However, tyrosine recombinases appear to lack well-defined DNA binding motifs with clear rules that specify which residues need to be mutated to achieve a particular desired target specificity. Guo F, et al., (1997) Structure of Cre recombinase complexed with DNA in a site-specific recombination synapse. Nature 389(6646):40-46, Chen Y, et al., (2000) Crystal structure of a Flp recombinase-Holliday junction complex: assembly of an active oligomer by helix swapping. Mol Cell 6(4):885-897. Moreover, the entire structure of tyrosine recombinases seems to take part in the functional target recognition. Buchholz F & Stewart A F (2001), Bolusani S, et al. (2006). Such mode of protein-DNA binding restricts the evolution process of the target-specific tyrosine recombinase variants to mainly random target-linked mutagenesis, although the modification of the residues known to participate in the protein-DNA recognition can speed up the evolution process. Buchholz et al. (2001), Sarkar I, et al. (2007), Shultz et al. (2011), Karpinski J, et al. (2016) Directed evolution of a recombinase that excises the provirus of most HIV-1 primary isolates with high specificity. Nat Biotechnol 34(4):401-409, Shah et al., (2015) Target-specific variants of Flp recombinase mediate genome engineering reactions in mammalian cells. The FEBS journal 282(17):3323-3333.

Thus, there remains in the art a need for improved compositions and methods for genomic engineering.

SUMMARY OF THE DISCLOSURE

The invention provides a non-naturally occurring chimeric tyrosine recombinase polypeptide comprising a tyrosine recombinase variant domain and a TAL DNA-binding domain, such as where the tyrosine recombinase variant is selected from a group consisting of Flp, CRE (and Cre-like recombinases such as Dre, SCre, Vcre, Vika, Nigri, and Panto), R, B2, B3, KD, KW, SM, and TD. In certain embodiments of the invention, the chimeric tyrosine recombinase is a chimeric Flp-TAL recombinase and the tyrosine recombinase variant is a Flp recombinase variant. In some embodiments of the invention, the chimeric tyrosine recombinase is a chimeric Cre-TAL recombinase, a chimeric R-TAL recombinase, a chimeric B2-TAL recombinase, a chimeric B3-TAL recombinase, a chimeric KW-TAL recombinase, a chimeric SM-TAL recombinase, and/or a chimeric TD-TAL recombinase.

In certain instances, the presence of a linker peptide may optionally be included in the chimeric tyrosine recombinase of the invention. In such cases, the linker peptide operably connects the tyrosine recombinase variant domain and the TAL DNA-binding domain (TAL DBD). When present, the linker peptide may operably connect the N-terminus of the tyrosine recombinase variant domain to the C-terminus of the TAL DNA-binding domain. Alternatively, the linker peptide may operably connect the C-terminus of the tyrosine recombinase variant domain to the N-terminus of the TAL DNA-binding domain. In certain instances, additional sequences of TAL beyond the core TAL DBD may function as a linker.

In certain embodiments, the chimeric tyrosine recombinase may advantageously include a nuclear localization signal. Certain tyrosine recombinases, such as Flp, contain an endogenous nuclear localization signal. However, a heterologous NLS may still enhance recombinase activity even for those tyrosine recombinases that already contain an endogenous NLS. When utilized, the heterologous nuclear localization signal (NLS) is operably linked to the chimeric tyrosine recombinase.

The recombinase variant domain utilized in the chimeric recombinases of the invention will often have reduced recombinase activity, relative to its respective wild-type tyrosine recombinase. Such activity may be 25, 50, 75, or 90 percent reduced, relative to the wild type level of activity. Activity may be measured, for example, in *E. coli* as described herein.

The chimeric tyrosine recombinases of the invention may have a range of specificities in each of the domains of the chimeric recombinase. For example, the tyrosine recombinase variant domain may be broadly specific, specific, very specific, highly specific, or stringently specific for it target sequence. In the case of Flp, for example, that sequence is denoted FRT. Thus, the for the chimeric Flp-TAL recombinases of the invention, the target sequence for the Flp variant domain will generally be a FRT-like sequence. Similarly, in the case where the chimeric tyrosine recombinase is a chimerice Cre-TAL recombinases, where Cre recognizes a sequence known as Lox (or LoxP), the target sequence will generally be a Lox-like sequence, etc.

Similarly, the TAL DNA-binding domain may also be specific, very specific, highly specific, or stringently specific for its target sequence. Generally, that target sequence of the TAL DNA-binding domain will be upstream or downstream of the target sequence of the recombinase domain. In certain instances, the sequences targeted by the tyrosine recombinase domain and the TAL DNA-binding domains will be separated from one another (upstream and/or downstream) by 3-12 bp.

As noted, the level of specificity for the TAL DNA-binding domain may be specific, very specific, highly specific, or stringently specific for the target nucleic acid sequence. Generally, the length of the target nucleic acid sequence will be in the range of about 9-24 bp, 12-24 bp, or 15-24 bp in length, though in certain instances longer recognition sequences of up to about 35 bp may be used.

In certain embodiments of the invention, the chimeric tyrosine recombinases, including Flp-TAL recombinases of the invention, where the tyrosine recombinase variant domain may a have broad or relaxed target sequence specificity relative to the wild-type recombinase. This may be advantageous in those instances where it is desirable for the target specificity of the chimeric tyrosine recombinase to be driven substantially by the sequence to which the TAL DNA-binding domain has been programmed.

The invention also provides a chimeric tyrosine recombinase, such as a chimeric Flp-TAL recombinase, where the TAL DNA-binding domain stabilizes the binding of the chimeric recombinase on its target sequence and enhances the recombinase activity of the tyrosine recombinase domain.

In certain embodiments, the invention provides a chimeric tyrosine recombinase, such as a Flp-TAL recombinase, wherein the chimeric recombinase is able to recombine a target sequence in a prokaryotic cell. The invention also provides a chimeric tyrosine recombinase, such as a chimeric Flp-TAL, where the chimeric recombinase is able to recombine a genomic target sequence in a eukaryotic cell.

In certain embodiments of the invention, the chimeric tyrosine recombinases are most advantageously utilized in pairs. Thus, the invention also provides a composition where there is a first and a second chimeric tyrosine recombinase, such as a chimeric Flp-TAL recombinase and chimeric Cre-TAL recombinase, where the first chimeric tyrosine recombinase contains a TAL DNA-binding domain that is specific, very specific, highly specific, or stringently specific for a nucleic acid sequence upstream of the recombinase target sequence (such as a FRT-like sequence) and the second chimeric tyrosine recombinase contains a TAL DNA-binding domain that is specific, very specific, highly specific, or stringently specific for a nucleic acid sequence downstream of the recombinase target sequence (such as a FRT-like sequence). Often, the tyrosine recombinase target sequence and the TAL DNA-binding sequence may be separated by 3-12 bp. Pairs of chimeric tyrosine recombinases may have the same tyrosine recombinase module and differ in the TAL DBD module. Alternatively, individual tyrosine recombinases in a pair of chimeric tyrosine recombinases may be contain tyrosine recombinases that differ in the specificity of the recombinase module for its target sequence (as in, a pair of chimeric Flp-TAL recombinases where one is highly specific one FRT-like sequence and the other is highly specific for another FRT-like sequence or broadly specific for many FRT-like sequences). Alternatively, a pair of chimeric tyrosine recombinases may differ in identity of the tyrosine recombinase itself (as in, a chimeric Cre-TAL recombinase and a chimeric R-TAL recombinase).

In those embodiments of the invention, where the chimeric tyrosine recombinase is a chimeric Flp-TAL recombinase, the Flp variant domain may contain at least 2, 3, 4, 5, 6, 7, 8, or 9 amino acid substitutions selected from the group consisting of A35T, I45V, T50A, A55H, A55S, S59G, S59N, S114P, K173R, I295F, A363E. In some embodiments of the invention, the Flp variant domain may contain at least 2, 3, 4, 5, or all 6 amino acid substitutions selected from the group consisting A35T, I45V, T50A, S114P, I295F, and A263E. In some embodiments of the invention, the Flp variant domain may contain at least 2, 3, 4, 5, 6, 7, 8, 9, 10, 11, 12, or all 13 amino acid substitutions selected from the group consisting of A35T, M44V, T50A, A55H, S59G, K75R, S114P, I157V, K173R, S193G, I295F, and A363E. In some embodiments of the invention, the Flp variant domain may contain at least 2, 3, 4, 5, 6, 7, 8, 9, 10, 11, 12, 13, or all 14 amino acid substitutions selected from the group consisting of Q3R, Q18R, A35T, I45V, T50A, A55H, S59G, K85E, S114P, K173R, L285H, I295F, A324I, and A363E. In some embodiments of the invention, the Flp variant domain may contain at least 2, 3, 4, 5, 6, 7, 8, 9, 10, 11, 12, 13, 14, or all 15 amino acid substitutions selected from the group consisting of A35T, I45V, T50A, A55S, M58V, S59N, T62S, S114P, S130P, F171S, T176A, V213E, N290S, I295F, and A363E.

The invention also provides a chimeric Flp-TAL recombinase, where the Flp variant domain is evolved from a library of Flp genes, where genes bearing common as well as unique mutations are used as templates for generating shuffled variant libraries which can be screened to identify the desired target specificity. In some instances, those common mutations may be selected from one or more of A35T, I45V, T50A, S114P, I295F, and A263E. In some embodiments of the invention, the Flp variant domain may also (or alternatively) be evolved from a library of Flp genes that are randomized at codons 55, 58 and 59.

In those embodiments of the invention where the chimeric tyrosine recombinase is a chimeric Flp-TAL recombinase, the Flp variant domain may be a Flp variant identified in a screening system using a reporter construct bearing FRT and FRT-like sequence.

With respect to the TAL DNA-binding domain utilized in the chimeric tyrosine recombinase of the invention (such as with Flp-TAL recombinases) the TAL DNA-binding domain may be a truncation of the N-terminus and/or the C-terminus of the full TAL effector amino acid sequence. In certain embodiments of the invention, the TAL DNA-binding domain is the core TAL DNA-binding domain that begins at position +152 of the N-terminus of the TAL effector and ends at the position +95. In certain embodiments, however, it may be advantageous for the TAL DNA-binding domain to include amino acid sequence from the TAL effector extending from beyond the N-terminus and/or the C-terminus of the core TAL DNA-binding domain. In certain instances, the TAL effector amino acid sequence extending from the N-terminus and/or the C-terminus of the core TAL DNA-binding domain of the TAL effector may function as a linker between the tyrosine recombinase variant domain and the TAL DNA-binding domain.

In some embodiments, the invention provides a chimeric tyrosine recombinase, such as a chimeric Flp-TAL recombinase, where the recombinase variant domain of the chimeric recombinase has broad (relaxed) specificity to more than one recombination target sequence and target specificity is primarily driven by the specificity of the TAL DNA-binding domain. In some embodiments where the chimeric recombinase is a chimeric Flp-TAL recombinase and the Flp recombinase variant domain is broadly specific for a multiplicity of FRT-like target sequences, the TAL DNA-binding domain may be programmed to be specific, very specific, highly specific, or strictly specific for a target sequence. In certain instances, those target sequences may be separated from one another by 3-12 bp.

The invention also provides a chimeric tyrosine recombinase, such as a chimeric Flp-TAL recombinase, where the isolated recombinase variant domain is unable to efficiently recombine a genomic target sequence (such as a FRT-like genomic sequence) in the absence of the TAL DNA-binding domain.

The invention also provides a chimeric tyrosine recombinase, such as a chimeric Flp-TAL recombinase, where both the recombinase variant domain and the TAL-DNA binding domain are evolved or programmed to be specific, very specific, highly specific, or strictly specific for a target sequence. Those target sequences may be separated from one another by 3-12 bp.

The invention also provides a nucleic acid encoding a non-naturally occurring chimeric tyrosine recombinase comprising a regulatory element operable in a target cell, said regulatory element operably linked to a nucleic acid sequence encoding a chimeric tyrosine recombinase having a tyrosine recombinase variant domain and a TAL DNA-binding domain, where the tyrosine recombinase variant is selected from a group consisting of Flp, Cre (and Cre-like recombinases such as Dre, SCre, Vcre, Vika, Nigri, and Panto), R, B2, B3, KD, KW, SM, and TD. In some embodiments of the invention, the encoded chimeric tyrosine recombinase is a chimeric Flp-TAL recombinase and the tyrosine recombinase variant is a Flp recombinase variant. Nucleic acids of the invention may include endogenous or exogenous regulatory elements, such as enhancers, promoters, and polyadenylation sites. Suitable promoters for the nucleic acids of the invention include inducible, constitutive, or tissue specific promoters. Such promotors may be eukaryotic or prokaryotic.

The invention also includes embodiments where the chimeric tyrosine recombinase of the invention that is encoded in the nucleic acid contains an additional nucleic acid sequence encoding a linker peptide. In such cases, the encoded linker peptide operably connects the Flp recombinase domain to the TAL DNA-binding domain of the encoded chimeric polypeptide. When present, the encoded linker peptide may operably connect the N terminus of the recombinase variant domain to the C terminus of the TAL DNA-binding domain. Alternatively, the encoded linker peptide may operably connect the C-terminus of the recombinase variant domain to the N-terminus of the TAL DNA-binding domain.

The invention further provides a nucleic acid that encodes a chimeric tyrosine recombinase, such as a chimeric Flp-TAL recombinase, where the nucleic acid further may further encode a heterologous nuclear localization signal (NLS) operably linked to the chimeric recombinase.

The invention further provides a nucleic acid that encodes a chimeric tyrosine recombinase, such as a chimeric Flp-TAL recombinase, where the encoded tyrosine recombinase variant domain has reduced recombinase activity, relative to wild-type tyrosine recombinase. Such activity may be 25, 50, 75, or 90 percent reduced, relative to the wild type level of activity, as measured in vitro.

The chimeric tyrosine recombinase, such as a chimeric Flp-TAL recombinase, encoded by the nucleic acids of the invention may have a range of specificities in each of the encoded domains of the chimeric recombinase. For example, the tyrosine recombinase variant domain may be broadly specific, specific, very specific, highly specific, or stringently specific for it target sequence. In the case of Flp, for example, that sequence is denoted FRT. Thus, the for the chimeric Flp-TAL recombinases of the invention, the target sequence for the Flp variant domain will generally be a FRT-like sequence.

Similarly, the TAL DNA-binding domain encoded by the nucleic acids of the invention may also be specific, very specific, highly specific, or stringently specific for it's target sequence. Generally, that target sequence will be upstream or downstream of the target sequence of the recombinase domain. In certain instances, the sequences targeted by the tyrosine recombinase domain and the TAL DNA-binding domains will be separated from one another (upstream or downstream) by 3-12 bp. Generally, the length of the target nucleic acid sequence for the encoded TAL DNA-binding domain of the chimeric recombinase will be a nucleic acid sequence about 9-24 bp, 12-24 bp, or 15-24 bp in length, though in certain instances the recognition sequence may be from about 9 bp or up to about 35 bp.

The invention further provides a nucleic acid encoding a chimeric tyrosine recombinase, such as a chimeric Flp-TAL recombinase, where the encoded recombinase variant domain has broad or relaxed target sequence specificity relative to the wild-type recombinase. In such instances the target specificity of the chimeric tyrosine recombinase may be driven substantially by the sequence to which the TAL DNA-binding domain has been programmed.

The invention further provides a nucleic acid encoding a chimeric tyrosine recombinase, such as a chimeric Flp-TAL recombinase, where the encoded TAL DNA-binding domain stabilizes the binding of the encoded chimeric recombinase on its target sequence and enhances the recombinase activity of the encoded tyrosine recombinase domain.

In certain embodiments, the invention further provides a nucleic acid encoding a chimeric tyrosine recombinase, such as a chimeric Flp-TAL recombinase, where the encoded chimeric recombinase is able to recombine a target sequence in a prokaryotic cell. The invention also provides a nucleic acid encoding a chimeric tyrosine recombinase, such as a chimeric Flp-TAL, where the chimeric recombinase is able to recombine a genomic target sequence in a eukaryotic cell.

In those embodiments of the invention, where nucleic acid encodes a chimeric Flp-TAL recombinase, the encoded Flp variant domain may contain at least 2, 3, 4, 5, 6, 7, 8, or 9 amino acid substitutions selected from the group consisting of A35T, I45V, T50A, A55H, A55S, S59G, S59N, S114P, K173R, I295F, A363E. In some embodiments of the invention, the nucleic acid encodes a chimeric Flp-TAL recombinase where the encoded Flp variant domain may contain at least 3, 4, 5, or all 6 amino acid substitutions selected from the group consisting A35T, I45V, T50A, S114P, I295F, and A263E. In some embodiments of the invention, the nucleic acid encodes a chimeric Flp-TAL recombinase where the encoded Flp variant domain may contain at least 2, 3, 4, 5, 6, 7, 8, 9, 10, 11, 12, or all 13 amino acid substitutions selected from the group consisting of A35T, M44V, T50A, A55H, S59G, K75R, S114P, I157V, K173R, S193G, I295F, and A363E. In some embodiments of the invention, the nucleic acid encodes a chimeric Flp-TAL recombinase where the encoded Flp variant domain may contain at least 2, 3, 4, 5, 6, 7, 8, 9, 10, 11, 12, 13, or all 14 amino acid substitutions selected from the group consisting of Q3R, Q18R, A35T, I45V, T50A, A55H, S59G, K85E, S114P, K173R, L285H, I295F, A324I, and A363E. In some embodiments of the invention, the nucleic acid encodes a chimeric Flp-TAL recombinase where the encoded Flp variant domain may contain at least 2, 3, 4, 5, 6, 7, 8, 9, 10, 11, 12, 13, 14, or all 15 amino acid substitutions selected from the group consisting of A35T, I45V, T50A, A55S, M58V, S59N, T62S, S114P, S130P, F171S, T176A, V213E, N290S, I295F, and A363E.

The invention also provides a nucleic acid encoding a chimeric Flp-TAL recombinase, where the encoded Flp variant domain is evolved from a library Flp genes where genes bearing common as well as unique mutations are used as templates for generating shuffled variant libraries which can be screened to identify the desired target specificity. In some embodiments, those common mutations may be selected from one or more of A35T, I45V, T50A, S114P, I295F, and A263E. In certain embodiments of the invention, the nucleic acid may encode a chimeric Flp-TAL recombinase, where the encoded Flp variant domain is also (or alternatively) evolved from a library Flp genes that are randomized at codons 55, 58 and 59.

In those embodiments of the invention where the nucleic acid encodes a chimeric Flp-TAL recombinase, the encoded Flp variant domain may be a domain identified in a screening system using a reporter construct bearing FRT and FRT-like sequences.

The invention also provides a nucleic acid encoding a chimeric tyrosine recombinase, such as a chimeric Flp-TAL recombinase, where the TAL DNA-binding domain encoded by the nucleic acid is a truncation of the N-terminus and/or the C-terminus of the full TAL effector amino acid sequence. In some such embodiments, the encoded TAL DNA-binding domain is the core TAL DNA-binding domain that begins at position +152 of the N-terminus of the TAL effector and ends at the position +95. In some embodiments, however, it may be advantageous for the encoded TAL DNA-binding domain to include amino acid sequences from the TAL effector extending from beyond the N-terminus and/or the C-terminus of the core TAL DNA-binding domain. In some of those instances, the TAL effector amino acid sequence extending from the N-terminus and/or the C-terminus of the core TAL DNA-binding domain of the TAL effector may function as a linker between the tyrosine recombinase variant domain and the TAL DNA-binding domain.

The invention also provides a nucleic acid encoding a chimeric tyrosine recombinase, such as a chimeric Flp-TAL recombinase, where the recombinase variant domain portion of the encoded chimeric recombinase has broad specificity to more than one recombination sequence and target specificity of the chimeric recombinase is primarily driven by the specificity of the TAL DNA-binding domain. In certain of the embodiments where the encoded Flp recombinase variant domain is broadly specific for a multiplicity of FRT-like target sequences, the nucleic acid may encode a chimeric Flp-TAL recombinase where the TAL DNA-binding domain is programmed to be specific, very specific, highly specific, or strictly specific for a target sequence. In certain instances, those target sequences may be separated from one another by 3-12 bp.

The invention also provides a nucleic acid encoding a chimeric tyrosine recombinase, such as a chimeric Flp-TAL recombinase, where the encoded isolated Flp variant domain is unable to efficiently recombine a genomic target sequence (such as a FRT-like genomic target sequence) in the absence of the TAL DNA-binding domain.

The invention also provides a nucleic acid encoding a chimeric tyrosine recombinase, such as a chimeric Flp-TAL recombinase, where both the encoded recombinase variant domain and the encoded TAL-DNA binding domain are evolved or programmed to be specific, very specific, highly specific, or strictly specific for their respective target sequences. In some instances, those target sequences may be separated from one another by 3-12 bp.

The nucleic acids of the invention may be most conveniently utilized when in the form of a nucleic acid vector. Suitable vectors are well known in the art and may be selected according to the particular application. Nucleic acid vectors may include reporter genes, as appropriate.

In some embodiments, the nucleic acids of the invention may include one or more FRT or FRT-like sites (or the corresponding recombination sites when using other tyrosine recombinases). In some instances, it may be advantageous for the nucleic acids to include a pair of FRT and/or FRT-like sites (or their corresponding equivalents). In some such instances, the pair of FRT and/or FRT-like sites may be arranged in a head to head orientation. In other instances, the pair of FRT and/or FRT-like sites may be arranged in a head to tail orientation. In those instances where the vector is an inversion reporter construct, a reporter may be located between a pair of FRT and/or FRT-like sites oriented in a head to head orientation such that a successful inversion recombination event orients the reporter such that it is expressed. In those instances where the vector is an deletion reporter construct, a reporter may be located between a pair of FRT and/or FRT-like sites oriented in a head to tail orientation. In certain embodiments of the invention, any of the nucleic acids and vectors of the invention may also include a selectable marker.

In some embodiments, the invention provides a composition having a pair of vectors where each vector encodes a different chimeric tyrosine recombinase, such as a Flp-TAL recombinase. In such embodiments, typically the first encoded chimeric tyrosine recombinase (such as a chimeric Flp-TAL recombinase) is encoded on a first vector and contains an encoded TAL DNA-binding domain that is specific, very specific, highly specific, or stringently specific for a nucleic acid sequence upstream of a target recombination sequence (such as a FRT-like sequence) and the second encoded chimeric tyrosine recombinase (such as a chimeric Flp-TAL recombinase) is encoded on a second vector and contains an encoded TAL DNA-binding domain that is specific, very specific, highly specific, or stringently specific for a nucleic acid sequence downstream of the recombination target sequence (such as a FRT-like sequence).

The invention also provides a chimeric Flp-TAL recombinase polypeptide system comprising at least two different chimeric Flp-TAL recombinase polypeptides, wherein each of said chimeric Flp-TAL recombinase polypeptides contains a Flp recombinase domain, a linker peptide, and a TAL DNA binding domain, wherein the first of the two different chimeric Flp-TAL recombinase polypeptides binds on a first side of a target nucleic acid sequence in a cell and the second of the two different chimeric Flp-TAL recombinase polypeptides binds on a second side of the target nucleic acid sequence in the cell, forming a nucleic-acid protein complex, whereby the target nucleic acid sequence is altered.

The invention also provides a chimeric Flp-TAL recombinase nucleic acid system comprising at least one nucleic acid vector having a first regulatory element operable in a target cell, where the first regulatory element is operably linked to a nucleotide sequence encoding a first chimeric Flp-TAL recombinase protein, where the first chimeric Flp-TAL recombinase protein contains a first Flp variant recombinase domain, an optional first linker peptide, and a first TAL DNA-binding domain, where the first Flp variant recombinase domain (or the first linker peptide) operably connects the first Flp recombinase domain to the first TAL DNA-binding domain, and a second regulatory element operable in a target cell, where the second regulatory element is operably linked to a nucleic acid encoding a second chimeric Flp-TAL recombinase protein, where the second chimeric Flp-TAL recombinase protein contains a second Flp recombinase domain, an optional second linker peptide, and a second TAL DNA-binding domain, where the second Flp recombinase variant domain (or the second linker peptide) operably connects the second Flp recombinase domain to the second TAL DNA-binding domain, where the first TAL DNA-binding domain of the first of the two different chimeric Flp-TAL recombinase polypeptides binds on a first side of a target nucleic acid sequence in a cell and the second TAL DNA-binding domain of the two different chimeric Flp-TAL recombinase polypeptides binds on a second side of the target nucleic acid sequence in the cell, forming a nucleic acid-protein complex, whereby the target nucleic acid sequence is altered.

The invention also provides a method of altering a target sequence in the genome of a target cell that comprises introducing into the target cell and expressing a chimeric Flp-TAL recombinase nucleic acid system, where the system comprises at least one nucleic acid vector having a first regulatory element operable in the target cell, where the first regulatory element is operably linked to a nucleotide sequence encoding a first chimeric Flp-TAL recombinase protein, and the first chimeric Flp-TAL recombinase protein contains a first Flp recombinase variant domain, an optional first linker peptide, and a first TAL DNA-binding domain, where the first Flp recombinase variant domain (or the optional linker peptide) operably connects the first Flp recombinase domain to the first TAL DNA-binding domain, and a second regulatory element operable in said target cell, where the second regulatory element is operably linked to a nucleotide sequence encoding a second chimeric Flp-TAL recombinase protein, and the second chimeric Flp-TAL recombinase protein contains a second Flp recombinase variant domain, an optional second linker peptide, and a second TAL DNA binding domain, where the second Flp recombinase variant domain (or the optional second linker peptide) operably connects the second Flp recombinase domain to the second TAL DNA-binding domain, where the first TAL DNA-binding domain targets a nucleic acid sequence on a first side of the target sequence and said second TAL DNA-binding domain targets a nucleic acid sequence on a second side of the target sequence forming a nucleic acid-protein complex, whereby the target nucleic acid sequence in the cell is altered. The invention also provides methods where the alteration in the target nucleic sequence is and inversion, a deletion, or dual RMCE.

The invention also provides a method of altering a target sequence in the genome of a target cell that comprises introducing into the target cell a chimeric Flp-TAL recombinase polypeptide system, said system comprising a first chimeric Flp-TAL recombinase protein and a second chimeric Flp-TAL recombinase protein, each of said chimeric Flp-TAL recombinase proteins containing a Flp recombinase variant domain, an optional linker peptide, and a TAL DNA-binding domain, where the Flp recombinase variant domain (or the optional linker peptide) operably connects the Flp recombinase variant domain to the TAL DNA-binding domain, where the TAL DNA-binding domain of the first chimeric Flp-TAL recombinase protein targets a nucleic acid sequence on a first side of the target sequence and the TAL DNA-binding domain of the second chimeric Flp-TAL recombinase protein targets a nucleic acid sequence on a second side of the target sequence and forming a nucleic acid-protein complex, whereby introduction of said first and second chimeric Flp-TAL recombinases in said target cell alters the target sequence of the target cell. The invention also provides methods where the alteration in the target nucleic sequence is an inversion, a deletion, or dual RMCE.

BRIEF DESCRIPTION OF THE DRAWINGS

FIG. 1A shows a general mode of target binding by Flp-TAL recombinases. FIG. 1B shows the possible relative arrangements of the Flp and TAL recognition sequences and the connections between the Flp and TAL modules.

FIG. 2A to FIG. 2C: FRT-like sequences FL-61, FL-63, and FL-71. FIG. 2A shows the relative location of FL-61, FL-63, and FL-71 in the human genome. FIG. 2B shows an alignment of FRT (SEQ ID NO 47), FL-61 (SEQ ID NO 16), FL-63 (SEQ ID NO 17), and FL-71 (SEQ ID NO 18). The base pairs in FL-61, FL-63, and FL-71 that differ from the corresponding base pairs in FRT are shown as lower case bold black letters. FIG. 2C shows FL-61_TAL (SEQ ID NO 19), FL-63_TAL (SEQ ID NO 20), and FL-71_TAL (SEQ ID NO 21) sequences. 5'T bases for the TAL recognition sequences (marked by blue arrows) are shown in red.

FIG. 3A to FIG. 3E: Evolution of Flp-TAL recombinases. FIG. 3A: Inversion assay. The reporter contains the inversion cassette flanked by the recombination targets in the head-to-head orientation: FL-61, FL-63, or FL-71 (marked as RT) and FRT* that bears the spacer either from FL-61, FL-63, or FL-71, respectively. Upon expression of a recombination competent Flp variant, the cassette is inverted so the gene that encodes this variant can be amplified. FIG. 3B: Deletion assay. The deletion reporter has the lacZα cassette flanked by the recombination targets in the head-to-tail orientation. If a Flp variant is able to delete the cassette, the resulting bacterial cells will form white colonies when plated on the X-gal containing plates. FIG. 3C: Mutations in FV61, FV63, and FV71. FIG. 3D: Activity of FV61, FV63, and FV71 on the FL-61, FL-63, and FL-71 substrates. The assays were performed using the deletion reporter. FIG. 3E: Electrophoregram of the uniquely digested plasmid DNA isolated from the colonies poled from the respective plates shown in D. Ctr, control vectors; EV, expression vector; RV, reporter vector; EV+RV, Flpe expression vector and the deletion reporter that bears the lacZα cassette flanked by FRT, which was completely deleted; M, DNA ladder.

FIG. 4A: Schematics of the integration assays. The reporter can be integrated either into FL-61, FL-63, or FL-71 depending on the specificity of the Flp-TAL recombinase. Upon integration of pTarget into FL-61 or FL-63 the resultant cells become hygromycin resistant and red, while if integrated into FL-71, the cells become hygromycin resistant and green (images of the individual expanded $hygro^R$/red and $hygro^R$/green colonies are shown as examples). The analysis of the individual colonies was performed in two biological replicates. LJ and RJ show the locations of the diagnostic PCR products at the left and right junctions of the integrated reporter and genomic DNA. FIG. 4B: PCR analysis of the pooled $hygro^R$ colonies generated in the experiments with the Flp-TAL recombinase, the 'plain' recombinase variant, or the empty expression vector. LJ, RJ, the PCR analysis of the left and right junctions of pTarget integrated into the respective genomic sequences; M, DNA ladder. FIG. 4C, FIG. 4D, and FIG. 4E: Sequencing of the integration-specific PCR products LJ and RJ of pTarget integrated into FL-61 (SEQ ID NO 48) (SEQ ID NO 49), FL-63 (SEQ ID NO 50) (SEQ ID NO 51), and FL-71 (SEQ ID NO 52) (SEQ ID NO 53), respectively, confirmed their identity.

FIG. 5A to FIG. 5C: Flp-TAL recombinase can delete a genome fragment. FIG. 5A Schematic of the deletion assay. Upon expression of FV71-TAL, the DNA fragment that is located between two FL-71 sequences and that contains part of the reporter and genomic DNA gets deleted. FIG. 5B PCR analysis of the FV71-TAL treated cells which bear pTarget integrated into FL-61. The deletion activity was analyzed in three biological replicates. FL-61/LJ and FL-71/RJ, the PCR analysis of the respective junctions of the integrated pTarget before and after the treatment with FV71-TAL. M, DNA ladder. FIG. 5C Sequencing of the deletion-specific PCR product FL-71/RJ confirmed its identity (SEQ ID NO 53).

FIG. 8: Nucleic acid sequences and graphical representations of the recombination targets that are located in the vectors. These recombination targets help the vectors to integrate into the genomic FRT-like sequences FL-61 (SEQ ID NO 34), FL-63 (SEQ ID NO 35), and FL-71 (SEQ ID NO 36), respectively.

FIG. 9: Amino acid sequence and graphical representation of a representative TAL DNA-binding domain (SEQ ID NO 15).

FIG. 10: Amino acid sequence and graphical representation of a representative Flp-TAL recombinase (SEQ ID NO 37).

FIG. 11: Graphical representation of FL-71 Left TAL sequences of different lengths (SEQ ID NO 21), (SEQ ID NO 44), (SEQ ID NO 45).

FIG. 12: Graphical representation of loxP-like sequence 69058 (LL-69), with different TAL sequences (SEQ ID NO 55), (SEQ ID NO 41), (SEQ ID NO 42), (SEQ ID NO 43).

FIG. 13: Graphical representation of partial coding sequence for chimeric iCreM24/69-TAL recombinase (SEQ ID NO 40).

FIG. 14A: Relative location of the loxP-like sequence LL69 and FRT-like sequence FL71 in the human genome. These sequences are recognized by CV69 and FV71, respectively. FIG. 14B: Schematic of the dual RMCE reaction to test the replacement activity of the Cre and Flp variants. The cells, in which the replacement occurred, express both EGFP and DsRed.

DETAILED DESCRIPTION OF THE INVENTION

Figure 1A:
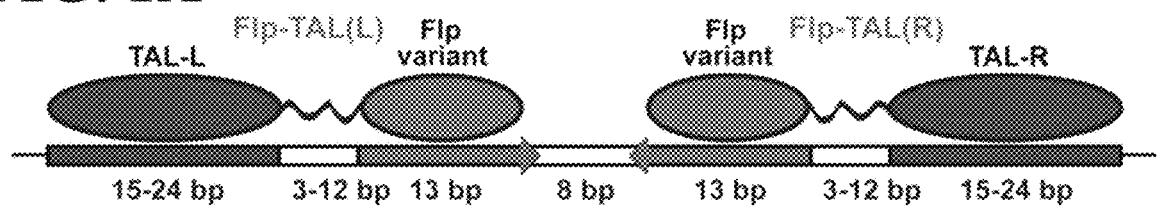
FIG. 1A and FIG. 1B: Flp-TAL recombinases.

The present invention applies a different approach to develop tyrosine recombinases with a desired target specificity. In this approach, a chimeric tyrosine recombinase is utilized that has two modules; one to help direct target binding and another for the catalytic function. In this approach, a tyrosine recombinase variant is fused with a DNA binding domain (DBD), the target specificity of which can be readily. The addition of the target-specific DNA binding domain helps to stabilize the recombinase variant on its target, thereby simplifying the process of reprogramming the target specificity of a tyrosine recombinase and increasing the activity of the chimeric recombinase relative to that of the recombinase module alone.

The present invention offers several advantages over existing compositions and methods for altering the genome of a target cell. First, unlike serine recombinases such as Cas9, the tyrosine recombinases utilized in the present invention do not rely on host cell DNA repair machinery to repair the strand breaks that occur during the recombination event. As such, the present invention is able to be utilized on cells that are not actively replicating, regardless of whether the host cell repair machinery is active or not. Second, unlike serine recombinases, tyrosine recombinases make single-stranded breaks (rather than double-stranded breaks), reducing the likelihood of unintended gross rearrangements of the genome. Moreover, the present invention utilizes tyrosine recombinases that have a greater number of potential target sites well distributed throughout the genome than, for example, the CRISPR/Cas9 system. Lastly, the present invention provides a method of targeting alterations in a genome with exceptional accuracy, with a lower potential for recombining at an unintended "off target" site than systems such as CRISPR/Cas9.

Definitions: In general, throughout this specification, terms are intended to be interpreted as they are understood by a person of ordinary skill in the art. However, the following terms may be more clearly understood by reference to the following definitions:

The term "wild-type" as used herein refers to a typical form of an organism, strain, nucleic acid, gene, protein, polypeptide, or characteristic as it occurs in nature.

The term "variant" as used herein refers to a mutated, artificially evolved, or other form of an organism, strain, gene, nucleic acid, protein, polypeptide, or characteristic that differs in some manner from the corresponding wild-type organism, strain, gene, nucleic acid, protein, polypeptide, or characteristic.

The term "chimeric" as used herein refers to a gene, coding region, nucleic acid, protein, or polypeptide that contains part or all of at least two genes, coding regions, nucleic acids, proteins, and/or polypeptides, that do not naturally exist together as such and have been assembled together to form a gene, coding region, nucleic acid, protein, polypeptide or combination thereof that does not naturally exist in nature.

The term "heterologous" as used herein is a term of art understood to refer to a nucleic acid or polypeptide sequence that is not naturally found with the wild-type nucleic acid, gene, protein, or polypeptide.

The term "tyrosine recombinase" as used herein refers to a group of enzymes that perform site-specific recombination in a manner that involves a tyrosine residue in the recombinase forming a covalent protein-DNA linkage in the reaction intermediate. Tyrosine recombinases break and rejoin single strands in pairs and form a Holliday junction intermediate. Examples of tryosine recombinases include the Flp recombinase from the 2u plasmid of *Saccharomyces cerevisiae* (as well as the thermostable variant of Flp, Flpe (SEQ ID NO 1; SEQ ID NO 2)) the Cre recombinase of bacteriophage P1 (as well as the codon optimized form of Cre, iCre (SEQ ID NO 3; SEQ ID NO 4)), the B2 recombinase from the pSB2 plasmid of *Zygosaccharomyces bailii* (SEQ ID NO 5), the B3 recombinase from the pSB3 plasmid of *Zygosaccharomyces rouxii* (SEQ ID NO 6), the KD recombinase from the pKD1 plasmid of *Kluyveromyces drosophilarum* (SEQ ID NO 7), the KW recombinase from the pKWS1 plasmid of *Kluyveromyces waltii* (SEQ ID NO 8), the R recombinase from the pSR1 plasmid of *Zygosaccharomyces rouxii* (SEQ ID NO 9), the SM recombinase from the pSM1 plasmid of *Zygosaccharomyces fermentati* (SEQ ID NO 10), the TD recombinase from the pTD1 plasmid of yeast *Torulaspora delbrueckii* (SEQ ID NO 11), λ Int, and others. Tyrosine recombinases are distinct from serine recombinases, such as Gin, Hin and others, where a serine residue in the recombinase forms a covalent protein-DNA linkage during the reaction intermediate and all strands are cut prior to strand exchange.

The terms "specific" or "specificity" as used herein refers to the property of having a degree of preference for recognizing, binding, hybridizing, recombining, or reacting with a desired target or substrate versus one or more non-desired targets or substrates under the conditions tested or specified.

In general, the terms "specific for" or having "specificity for" is used to refer to a preference of at least 50% for the desired target or substrate versus two or more non-desired targets or substrates collectively or for at least a 4:1 preference for the desired target or substrate versus a particular undesired target or substrate under the conditions tested or specified. The related term "very specific for" is used to refer to a preference of at least 80% for the desired target or substrate versus two or more non-desired targets or substrates collectively or for at least a 10:1 preference for the desired target or substrate versus a particular undesired target or substrate. The related terms "highly specific for" as used herein is used to refer to a preference of at least 90% for the desired target or substrate versus two or more non-desired targets or substrates collectively or for at least a 20:1 preference for the desired target or substrate versus a particular undesired target or substrate. The related term "strictly specific for" or having "strict specificity" as used herein is used to refer to a preference of at least 98% for the desired target or substrate versus two or more non-desired targets or substrates collectively or for at least a 100:1 preference for the desired target or substrate versus a particular undesired target or substrate. The related terms "completely specific for" or "complete specificity" are used herein to refer to a target or substrate preference of such a degree that no other binding, hybridization, or reaction is detectable under the conditions specified. Note that "completely specific for" and "complete specificity" are not intended to suggest that recognizing, binding, hybridizing, recombining, or reacting with an undesired target or substrate does not occur at all, but rather, that it does not occur beyond a barely detectable level under the conditions tested or specified. The words specific and specificity may be used interchangeably. Each of these levels of specificity may be referred to collectively as "narrow specificity."

In contrast, the terms "broadly specific for" or having "broad specificity" or "relaxed specificity" as used herein refers to the characteristic of being able to recognize, bind, hybridize, recombine, or react with a group of two or more desired potential targets or substrates such that each desired potential target or substrate is at least 75% utilized under the conditions tested or specified.

The terms "TAL DNA-binding domain" or "TAL DBD" as used herein refers to a polypeptide having the core TAL effector DNA-binding domain, which is located between position +152 (Δ152 truncation of the N-terminal segment of the TAL effector) and position +95 of the C-terminal segment of the TAL effector. See e.g., Miller J C, et al. (2011) A TALE nuclease architecture for efficient genome editing. Nat Biotechnol 29(2):143-148.

Chimeric tyrosine recombinases of the invention: Two classes of the chimeric tyrosine recombinases are contemplated as within the scope of the invention that, broadly speaking, differ at the level of the target specificity of their recombinase modules. In the first class of chimeric tyrosine recombinases, both modules of the chimeric recombinase (the tyrosine recombinase variant module and the extra DNA binding domain module) are evolved or engineered to be specific, very specific, highly specific, strictly specific, or completely specific for the particular genomic target sequence of interest. As such, this class of chimeric tyrosine recombinases represents what is perhaps the most target specific genome engineering tool presently available. Although modification of the target specificity of both the recombinase module and the DNA binding module can require more effort than that of the second class (described below), the amount of effort required is still quite manageable.

In the second class of chimeric tyrosine recombinases, the two modules can differ at the level of their target specificity such that a recombinase variant is evolved or utilized that has a somewhat relaxed or broad specificity toward a genomic target sequence (as compared to the wild-type recombinase), while the extra TAL DNA-binding module is engineered to be specific, very specific, highly specific, strictly specific or completely specific for a sequence to the left or right of the recombinase target sequence, so as to deliver the recombinase module to the particular target sequence where the recombination reaction is intended to take place. As the target specificity of the recombinase module is relatively broad, the recombinase module can be used to generate hybrid recombinases of different target specificity simply by changing the target specificity of the extra DNA binding module. Since the target specificity of the DNA-binding can be readily programmed, the effort to modify the target specificity of this class of chimeric tyrosine recombinases is relatively low.

The functional properties of chimeric tyrosine recombinases having a broad or relaxed specificity, are expected to be somewhat different. Since, ideally, the recombinase module should be able to recombine many, if not the majority of the high-scoring target-like sequences, target specificity of the respective chimeric tyrosine recombinases should be easily modified since all that will be required is the assembly of new TAL modules. On the other hand, the relaxed target specificity of this tyrosine recombinase module necessarily reduces specificity of these chimeric tyrosine recombinases. Nevertheless, even reduced, target specificity of these chimeric recombinases is expected to be sufficiently high to target just the sequences of interest since, as explained below, in addition to the target specificity of the two TAL modules (See e.g. Flp-TAL (FIG. 1A)), target specificity of the tyrosine recombinase module as well as the functional specificity of the target-like sequence spacer will also contribute to the overall chimeric tyrosine recombinase specificity.

Taking Flp as a representative example, target specificity of the Flp module with relaxed specificity reflects the sequence characteristics of the FRT-like sequences that differ them from a random nucleic acid sequence. In mammalian genomes, these sequence characteristics translate into one FRT-like sequence per about 5,000 base pairs which respectively decreases the probability to find an FRT-like sequence between two TAL binding sequences (FIG. 1A) by about three orders of magnitude.

This probability is further decreased by about three orders of magnitude due to the functional property of the FRT spacer (also called 'strand exchange region', FIG. 2B) that increases the overall recombination specificity of the Flp/FRT system. Although Flp does not make contacts to the spacer, the recombination specificity of the Flp/FRT system depends on the spacer sequence: only FRT variants with the same spacers will efficiently recombine with each other while FRT variants with different spacers will not. Since FRT has an 8-bp spacer, the probability to find a spacer sequence of this length is $1/4^8$ (or $1/65,536$). For the FRT-like sequences this probability is higher: $1/4^6/2$ (or $\sim 1/2,000$) since the first and the last base pairs of the spacer in these sequences are invariant: T/A and A/T, respectively, and the G/C content of the spacer is set to be equal or lower than 50%.

Taken together, the probability of finding an FRT-like sequence with a unique spacer that is located between the two TAL binding sequences is $\sim 1/10^7$ ($\sim 1/(5 \times 10^3) \times \sim 1/(2 \times 10^3)$) which ensures that the TAL-guided Flp variant with relaxed specificity toward FRT-like sequences will recombine just the sequence of interest. This, however, can only be realized if the tyrosine recombinase module of the chimeric tyrosine recombinase is not sufficiently active to recombine target-like sequences on its own, without the target stabilization effect by the TAL module. It is therefore important that tyrosine recombinase variants with relaxed target specificity are evolved to have a relatively low recombination activity as compared to their wild-type counterparts. Generally, when the activity of these recombinase variants is in the range of about 25 to about 50% relative to their wild-type counterparts, they are essentially inactive in a eukaryotic cell without the support of the TAL DBD.

Herein, we describe both classes of chimeric tyrosine recombinases and their use in genome engineering, primarily as exemplified by chimeric recombinases composed of variants of the tyrosine recombinase Flp (or Cre), together with a programmed DNA binding domain of the TAL effectors. More particularly, the chimeric Flp-TAL recombinases described herein contain a recombinase domain composed of a variant of the Flp recombinase (with either narrow or broad target specificity), fused directly or indirectly to a DNA binding domain composed of a TAL effector DNA binding domain (TAL DBD), with a linker optionally between the two domains. It will be readily apparent that since the tyrosine recombinases have similar three-dimensional organization, similar mode of target binding, and are well amenable to modification of their target specificity, the other members of the tyrosine recombinase family can be also utilized to generate chimeric TAL-fused tyrosine recombinases essentially as described herein. Moreover, since each recombinase has its own set of target sequences in a genome, these additional tyrosine recombinases can greatly diversify the sequences that can be targeted by the chimeric TAL-fused recombination system. Further, different TAL-fused chimeric tyrosine recombinases can be paired to perform dual RMCE to efficiently replace genome fragments. Importantly, the availability of several target-specific hybrid recombinases for dual RMCE would translate into shorter genome fragments that can be replaced: our analysis of the distribution of the target-like sequences for different recombinases in a genome shows that an arsenal of 5-6 hybrid recombinases is sufficient for reducing the size of the replaceable genomic fragments to about 1 kb.

Although this is believed to be the first use of such an approach with tyrosine recombinases, a somewhat similar approach has been previously applied to create chimeric serine recombinases such as zinc-finger recombinases, or ZFRs, TALE recombinases, or TALERs, and Cas9 recombinases, or recCas9, that were created by fusing the activated catalytic domains of the invertase Gin or the resolvase Tn3 with the DNA binding domains of either zinc fingers, TAL effectors, or the catalytically inactive Cas9 protein, respectively. See Akopian et al., Chimeric recombinases with designed DNA sequence recognition. Proc Natl Acad Sci USA 100(15):8688-8691 (2003), Gordley et al., Evolution of programmable zinc finger-recombinases with activity in human cells. J Mol Biol 367(3):802-813 (2007); Mercer et al., Chimeric TALE recombinases with programmable DNA sequence specificity. Nucleic Acids Res 40(21):11163-11172 (2012); and Chaikind et al., A programmable Cas9-serine recombinase fusion protein that operates on DNA sequences in mammalian cells. Nucleic Acids Res 44(20):9758-9770 (2016).

A modular design approach, in which proteins with different functional properties are fused together, has also previously been employed to develop hybrid site-specific nucleases: zinc finger nucleases (ZFNs), and transcription activator-like effector nucleases (TALENs), that are composed of a nonspecific DNA nuclease FokI and the respective DNA binding domains with programmable target specificity. Kim et al., Hybrid restriction enzymes: zinc finger fusions to Fok I cleavage domain. Proc Natl Acad Sci USA 93(3):1156-1160 (1996); Christian et al., Targeting DNA double-strand breaks with TAL effector nucleases. Genetics 186(2):757-761 (2010). Target affinity and specificity in these modular systems can be modified by changing the number of the target recognizing units in their DNA binding domains to achieve the optimal balance between target specificity and non-specific DNA binding. See Miller et al., A TALE nuclease architecture for efficient genome editing. Nat Biotechnol 29(2):143-148 (2011); Porteus et al., Gene targeting using zinc finger nucleases. Nat Biotechnol 23(8): 967-973 (2005); Urnov et al., Highly efficient endogenous human gene co/*rrection using designed zinc-finger nucleases. Nature 435(7042):646-651 (2005); Miller et al., An improved zinc-finger nuclease architecture for highly specific genome editing. Nat Biotechnol 25(7):778-785 (2007); Cermak et al., Efficient design and assembly of custom TALEN and other TAL effector-based constructs for DNA targeting. Nucleic Acids Res 39(12):e82 (2011); Gaj et al., ZFN, TALEN, and CRISPR/Cas-based methods for genome engineering. Trends Biotechnol 31(7):397-405 (2013).

As noted, suitable tyrosine recombinase variants for use in the present compositions and methods include, for example, variants of the Flp recombinase from the 2u plasmid of *Saccharomyces cerevisiae* (including the thermostable form of Flp, Flpe (SEQ ID NO 1; SEQ ID NO 2), variants of the Cre recombinase of bacteriophage P1 (including the codon optimized iCre (SEQ ID NO 3; SEQ ID NO 4), variants of the R recombinase from the pSR1 plasmid of *Zygosaccharomyces rouxii* (SEQ ID NO 9), variants of the B2 recombinase from the pSB2 plasmid of yeast *Zygosaccharomyces bailii* (SEQ ID NO 5), variants of the B3 recombinase from the pSB3 plasmid of *Zygosaccharomyces rouxii* (SEQ ID NO 6), variants of the KD recombinase from the pKD1 plasmid of *Kluyveromyces drosophilarum* (SEQ ID NO 7), variants of the KW recombinase from the pKWS1 plasmid of *Kluyveromyces waltii* (SEQ ID NO 8), variants of the SM recombinase from the pSM1 plasmid of *Zygosaccharomyces fermentati* (SEQ ID NO 10), and variants of the TD recombinase from the pTD1 plasmid of yeast *Torulaspora delbrueckii* (SEQ ID NO 10). Suitable variants of these recombinases will generally have at least 80, 85, 90, or 98 percent amino acid homology to at least the enzymatically active portion of their respective wild-type recombinase enzymes.

Suitable tyrosine recombinase variants may also include deletions mutants, thermostable variants, split recombinase proteins (such as described in Jullien et al., (2003) Nucleic Acids Research, Regulation of Cre recombinase by ligand-induced complementation of inactive fragments, Vol. 31, No. 21:e131; Kawano et al. (2016), A photoactivatable Cre-loxP recombination system for optogenetic genome engineering, dOI: 10.1038/nCHeMBI0.2205; and Jun et al. (2019) Noninvasive optical activation of Flp recombinase for genetic manipulation in deep mouse brain regions, Nature Communications, doi.org/10.1038/s41467-018-08282-8), fusions proteins, and the like.

Flp: Flp is a tyrosine recombinase, originally isolated from *Saccharomyces cerevisiae*. In yeast, Flp is found on the 2µ plasmid, where it promotes an inversion of the DNA between two 599-bp inverted repeats. Flpe is a thermostable form of Flp and may form a suitable basis for further evolution of Flp variants. (SEQ ID NO 1; SEQ ID NO 2) See Mol Biotechnol. 2011 September; 49(1)82-9. The minimal recombination site, known as the Flippase Recombinase Target (FRT), is composed of two inverted 13 bp arms, separated by an 8 bp spacer. The sequence recognized by the wild-type enzyme is 5'GAAGTTCC-TATACtttctagaGAATAGGAACTTC3'. (SEQ ID NO 12).

However, Flp variants are known and can be readily evolved that recognize FRT-like sequences. FRT-like sequences differ from the wild-type recognition sequence at one or more locations from FRT and are widely represented in the genome of mammalian cells. See Bolusani S, et al. (2006) Evolution of variants of yeast site-specific recombinase Flp that utilize native genomic sequences as recombination target sites. Nucleic Acids Res 34(18):5259-5269, Shultz et al., A genome-wide analysis of FRT-like sequences in the human genome. PLoS One 6(3):e18077 (2011), Shah et al., Li F, Voziyanova E, & Voziyanov Y (2015) Target-specific variants of Flp recombinase mediate genome engineering reactions in mammalian cells. The FEBS journal 282(17):3323-3333.

The Flp variants suitable for the chimeric Flp-TAL recombinases of the invention may either have a narrow target specificity or a somewhat relaxed broader target specificity. Flp variants that are specific, very specific, highly specific, strictly specific, or completely specific will generally be most useful for those embodiments of the invention that utilize a chimeric recombinase of the first class. Flp variants having a somewhat relaxed and broad specificity will be those embodiments of the invention that utilize a chimeric Flp-TAL recombinase of the second class.

Flp variants suitable for the chimeric Flp-TAL recombinases of the invention will typically have at least 80, 85, 90, 95, or 98 percent amino acid homology to the wild type Flp enzyme. Typically, suitable Flp variants will contain at least 2, 3, 4, 5, 6, 7, 8, or 9 of the following amino acid substitutions: A35T, I45V, T50A, A55H, A55S, S59G, S59N, S114P, K173R, I295F, A363E. Most typically, suitable Flp variants will contain at least 3, 4, 5, or all 6 of the following amino acid substitutions: A35T, I45V, T50A, S114P, I295F, and A263E. One specific example of a suitable Flp variant contains the following amino acid substitutions: A35T, M44V, I45V, T50A, A55H, S59G, K75R, S114P, I157V, K173R, S193G, I295F, and A363E. Another specific example of a suitable Flp variant contains the following amino acid substitutions: Q3R, Q18R, A35T, I45V, T50A, A55H, S59G, K85E, S114P, K173R, L285H, I295F, A324I, and A363E. Another specific example of a suitable Flp variant contains the following amino acid substitutions: A35T, I45V, T50A, A55S, S59N, T62S, S114P, S130P, F171S, T176A, V213E, N290S, I295F, and A363E. Without intending to be bound by any particular theory, it is believed that these amino acid substitutions contribute to allowing the Flp variants to recognize different FRT-like sequences in the genome. Additional mutations and amino acid substitutions are both permissible and contemplated, as such mutations and substitutions may contribute to relaxing or narrowing the Flp variant's target specificity.

Evolution of suitable target-specific or target-relaxed Flp variants can be facilitated if genes for known Flp variants bearing common as well as unique mutations are used as templates for generating shuffled variant libraries which can be screened to identify the desired target specificity. Examples of such Flp variants are known in the art and are described, for example, in Bolusani et al., Evolution of variants of yeast site-specific recombinase Flp that utilize native genomic sequences as recombination target sites. Nucleic Acids Res. 34(18):5259-5269 (2006), Shultz et al., A genome-wide analysis of FRT-like sequences in the human genome. PLoS One 6(3):e18077 (2011), and Shah et al., Target-specific variants of Flp recombinase mediate genome engineering reactions in mammalian cells. The FEBS journal 282(17):3323-3333 (2015). The pool of the template variant genes can be further enhanced by including in the library Flp genes that are randomized at codons 55, 58 and 59, since the amino acids at these positions contact the first four base pairs of the Flp binding elements of FRT that are known to be the most critical for the Flp-FRT recognition. (Shultz et al. 2011). By following this approach, Flp variants suitable for the Flp-TAL recombinases can be evolved in as little as one or two rounds of protein evolution using a pair of different, but related, recombination sequences such as a genomic FRT-like sequence and FRT.

Most often, the Flp recombinase activity of the variant utilized as the Flp recombinase module in either class of chimeric recombinases is somewhat reduced, as compared to the wild-type recombinase. Generally, the activity of the Flp recombinase variant will retain 75 percent or less, 50 percent or less, or 25 percent or less of the recombinase activity against the FRT-like target to which it was evolved, as compared to the wild type enzyme against its natural target FRT, under the conditions tested in *E. coli* assays, performed essentially the same as in Voziyanov et al., 2002. Briefly, competent cells harboring the recombination reporter pBU are transformed with p33-mFlp (either as individual variants or a mutagenised pool). LB medium (10 g/l NaCl (Sigma), 10 g/l tryptone peptone (Difco) and 5 g/l yeast extract (Difco)) ares added to the cells and Flp variants are expressed by the addition of L-arabinose to a final concentration of 0.1% for 2.5 hours at 37° C. Then cells are then plated on LB-plates (LB plus Bacto Agar (Difco)) supplemented with 100 mg/l ampicillin, 30 mg/l chloramphenicol, and 100-200 mg/l X-gal. Plates are then incubated at 37° C. for 24 hours and the colonies are then scored for their color (blue or white). Without intending to be bound by any particular theory, it is believed that the reduced recombinase activity in the variant utilized as a recombinase module in the chimeric enzyme helps to reduce the probability of undesired recombination of genomic sequences by the catalytic module on its own. In the context of the chimeric enzyme, however, the recombination activity of the recombinase module is enhanced upon binding to the desired target sequence as a result of the target binding stabilization by the TAL DNA binding domain module.

Flp variants with the desired properties may be identified, for example, using a screening system that is composed of inversion and deletion reporters that are used sequentially (FIGS. 3A and B). In such a screening system, reporter cassettes in these vectors are flanked by a pair of FRT or FRT-like recombination sites that are arranged in the head-to-head and head-to-tail orientations, respectively. The inversion and deletion reporters have different purpose. The inversion reporter is used to identify a large pool of Flp variants that are able to recombine both the FRT-like sequence and FRT (or two FRT-like sequences); these variants are selected by amplifying the Flp variant genes in the inversion-positive configuration of the reporter (FIG. 3A). The deletion reporter is used to screen the inversion-positive library of the Flp variants that are sufficiently active to delete the reporter cassette in at least some vector molecules (FIG. 3B).

Figure 6A:
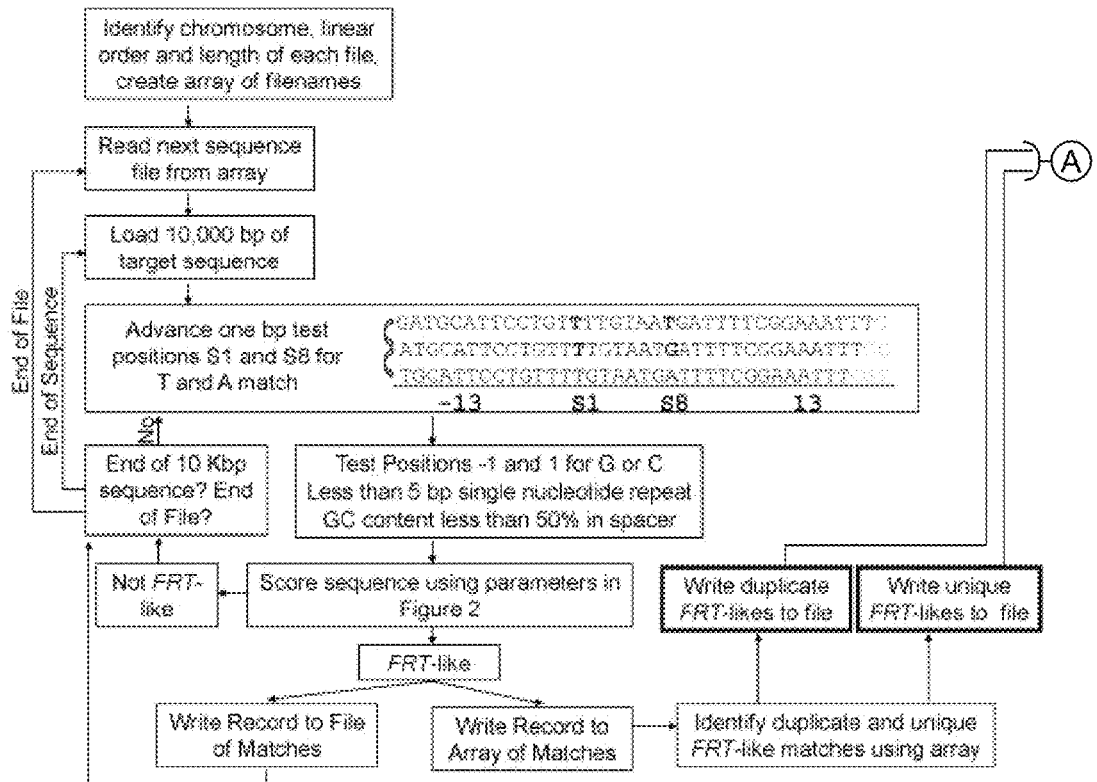
FIG. 6A and FIG. 6B: An overview of the TargetSiteAnalyzer bioinformatics package used to find FRT-like sequences (NCBI build 36.3). Heavy-bordered boxes indicate the creation of a file. File format boxes may have spaces added for readability in this figure (SEQ ID NOS. 54-73).
Figure 6B:
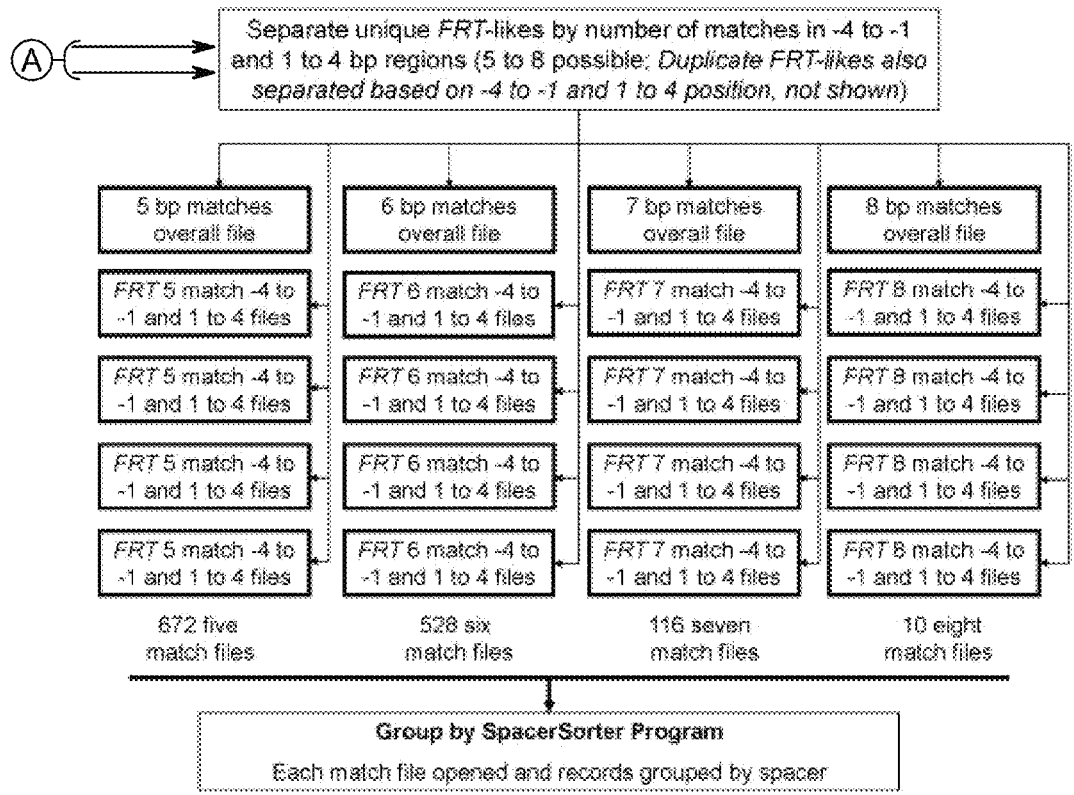

FRT-like sequences: Suitable target FRT-like sequences in a genome or nucleic acid sequence of interest may be identified using the publicly available program TargetSite-Analzyer. Shultz et al., A genome-wide analysis of FRT-like sequences in the human genome. PLoS One 6(3):e18077 (2011). TargetSiteAnalyzer is composed of three JAVA programs that are sequentially run: GenomeScanner, TargetSorter and SpacerSorter. Together, these programs simplify the task of identifying and then sorting FRT-like sequences within a genome of interest. An overview of these programs and the processing steps is shown in FIG. 6 and described in greater detail in Shultz et al. The programs were created and executed within the freely available NetBeans IDE (version 6.8; http://netbeans.org). The JAVA code for TargetSiteAnalyzer is freely available for download (See Shultz et al.).

GenomeScanner sequentially screens each DNA contig file within a genome build for FRT-like sequences using the rules that describe sites that can serve as functional recombination targets. A contig file is successively read as overlapping 34-nucleotide segments in 1-nucleotide increments. Each 34-nucleotide sequence is separated into three regions (See FIG. 6): two potential inverted recombinase binding elements (positions −13 through −1 and positions 1 through 13) and a spacer (positions s1 through s8). As does TargetFinder, GenomeScanner first checks if a putative spacer has a 'T' at position s1 and an 'A' at position s8 and whether GC content of the spacer equals or is below 50%.

Figure 7:
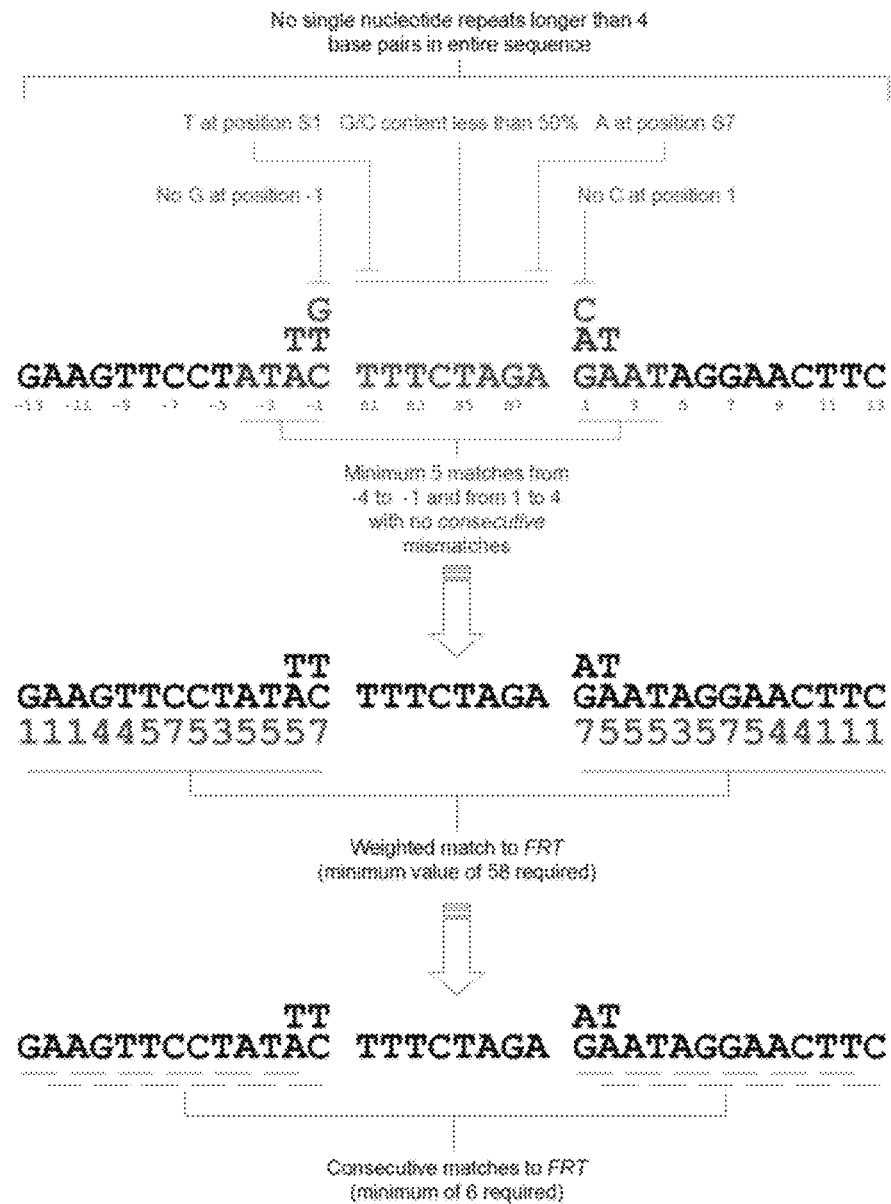
FIG. 7: A graphical representation of some FRT-like sequence identification parameters (relative to the FRT consensus sequence (SEQ ID NO 12).

If these criteria for a functional spacer are met, GenomeScanner tests positions −4 to −1 and 1 to 4 and also −7 and 7 of the putative binding elements of an FRT-like sequence for the number of matches and mismatches to the corresponding positions of FRT. In addition, the entire 34-nucleotide sequence of an FRT-like site is tested for any single nucleotide repeat longer than four nucleotides. The putative binding elements of an FRT-like sequence are also checked for the number of consecutive matches (FIG. 7). Each position in the binding elements of an FRT-like sequence (positions −13 to −1 and 1 to 13) that is matched to the corresponding position in FRT, is given a weighted value and a total score for an FRT-like sequence is generated that includes the number of matches within the 'proximal-8' sequence and the weighted value. Values of 80 or greater are indicative of a functional FRT-like sequence.

During program execution, GenomeScanner writes each match to a linear-order text file and to an internal array. After the last sequence file is processed, GenomeScanner uses the array to determine which FRT-like sequences are unique, then generates two additional output files: one containing only unique FRT-like sequences and a second containing FRT-like sequences with at least one exact duplicate. GenomeScanner reports the position of each identified FRT-like sequence both within the sequence contig files and within a chromosomal fragment map based on linear order of files for each chromosome and the cumulative base pairs for each chromosome.

TargetSorter works with the GenomeScanner generated files that contain both the unique and duplicated FRT-like sequences. The program groups the records based on the sequence of the most functionally important region of the FRT putative recombinase binding elements (−4 to −1 and 1 to 4). In this region, both complimentary strands are assigned a numeric value. The lowest value is used to assign the record to a file.

The SpacerSorter program sorts FRT-like sequences within each output file generated by TargetSorter based on spacer sequence. In similar fashion to the TargetSorter program, both directions of the spacer sequences are used to determine if a match exists. This final sorting step allows identification of those FRT-like sequences that can, in principle, recombine with each other by a single Flp variant specific for a particular sequence pattern in the 'proximal-8' region.

Functional genomic FRT-like sequences may also include 1, 2, or all 3 of the following characteristics: (1) within the proximal 4-bp DNA segments of both binding elements of an FRT-like sequence ('proximal-8 region'; positions 24 through 21 and 1 through 4, which make eight base pairs in total, FIG. 1A), it is desirable that there be at least five matches with the corresponding base pairs of FRT; (2) it is desirable that there not be consecutive mismatches within the same 4-bp DNA segments; (3) it is desirable that at least one binding element have a match at position 7. In addition, functional FRT-like sequences generally do not have mismatches at positions 21 and 1 simultaneously or a 'G' at position 21 or a at position 1. Functional genomic FRT-like sequences also generally have at least 5 matches in one of the binding elements and at least 6 consecutive matches within both of the binding elements.

Cre: Like Flp, Cre is a tyrosine recombinase. Found in bacteriophage P1, Cre promotes recombination between two 34 bp sites known as loxP. As with FRT, loxP is composed of two inverted 13 bp arms, separated by an 8 bp spacer. The sequence recognized by the wild-type enzyme is 5'ATAACTTCGTATAatgtatgcTATACGAAGTTAT3'. (SEQ ID NO 13)

As with Flp, Cre variants are known and can be readily evolved to recognize loxP-like sequences, which differ from the wild-type recognition sequence at one or more locations from loxP. See e.g. Missirlis et al. (2006). A high-throughput screen identifying sequence and promiscuity characteristics of the loxP spacer region in Cre-mediated recombination. BMC Genomics 7:73. As with Flp, Cre variants suitable for the chimeric tyrosine recombinases of the invention will typically have at least 80, 85, 90, 95, or 98 percent amino acid homology to the wild type Cre enzyme. Suitable Cre variants may, for example, contain one or more mutations at the monomer-monomer interface, such as R24M (which corresponds to codon 32 in iCre).

Other Tyrosine Recombinases:

Any tyrosine recombinase, including the R (SEQ ID NO 9), B2 (SEQ ID NO 5), B3 (SEQ ID NO 5), KD (SEQ ID NO 7), KW (SEQ ID NO 8), SM (SEQ ID NO 8), and TD (SEQ ID NO 11) recombinases may be utilized in the chimeric tyrosine recombinases of the invention in essentially the same manner as described for Flp and Cre. Suitable variants of each may be evolved in a manner analogous to the process described in greater detail for Flp.

TAL: TAL's are transcription-like effectors, from *Xanthomonas* sp., that function to bind DNA sequences in the promotor region of sequences in the host plant genes, promoting expression of plant genes that assist in bacterial infection.

TAL effectors contain a central domain of repeats that functions to specify the target sequence for DNA binding. The core TAL DNA-binding domain (DBD) begins at position +152 (Δ152 truncation of the N-terminal segment of the TAL effector) and ends at the position +95 of the C-terminal segment of the TAL effector. Additional N-terminal and/or C-terminal amino acids may be present, if desired, and in some cases may provide a chimeric enzyme with greater activity than just the core DBD alone. See Miller et al., A TALE nuclease architecture for efficient genome editing. Nat Biotechnol 29(2):143-148 (2011). In certain instances, these additional sequences may function as a linker between the Flp variant module and the TAL DBD module in the chimeric Flp-TAL recombinase.

The TAL DNA-binding domain may be readily programmed to be specific for a target nucleic acid sequence of interest. The requirements for the TAL recognition sequence are quite relaxed. The only major prerequisite for a TAL recognition sequence is a thymine at position N−1 of the sequence. Beyond that, the TAL recognition sequence can be readily programmed.

The core TAL DBD comprises a series of tandem 33-35 amino acid repeats, the consensus sequence of which is LTPDQVVAIASHDGGKQALETVQRLLPVLCQDHG. (SEQ ID NO 14) The polymorphic pair of residues at amino acids 12-13 (underlined), known as the repeat variable di-residue (RVD), specifies the nucleotide to which the particular repeat targets according to the following rules: HD→C, NI→A, NG→T, NN→G. See Miller et al. (2011) and Cermak et al., (2011).

The desired number and particular repeats are assembled, according to the above rules, to achieve the desired level of specificity to the desired target sequence. The Golden Gate TALEN kit, for example, may be used to assemble the desired TAL DNA binding domain. See Cermak et al., Efficient design and assembly of custom TALEN and other TAL effector-based constructs for DNA targeting. Nucleic Acids Res 39(12):e82 (2011).

The TAL DBD module is generally programmed to recognize a DNA sequence of about 9-24 bp, 12-24 bp, or 15-24 bp in length, located to the left or the right of desired FRT-like sequence in the genome or nucleic acid of interest. In general, the TAL recognition sequence should be long enough to achieve the desired level of specificity (to be specific, very specific, highly specific, strictly specific, or completely specific) for the particular application. 9-24 bp is a length that is easily manageable from a technical point of view, though longer or shorter recognition sequences such as less than 8 or to 35 bp or more, may be appropriate in particular circumstances and the desired level of specificity. For instance, it may be advantageous for the length of the TAL binding sequences to correlate somewhat with the degree of similarity between the Flp binding elements of the FRT-like sequence and that of FRT: The weaker the similarity, the longer the TAL recognition sequence that may be optimal. Conversely, where there is a stronger the similarity between the Flp binding elements or the FRT-like sequence and FRT, a shorter the TAL recognition sequence may be desired. An example of a TAL DBD module, programmed to recognize an 18 nucleotide sequence is shown in FIG. 9 (SEQ ID NO 15).

Generally, the TAL binding sequence is chosen so as to be separated from the recombinase binding element of the FRT-like sequence by 3 to 12 base pairs, though again, longer and shorter lengths may be appropriate in particular situations. In general, a separation of 3-12 bp is sufficient to minimize steric clashes between the hybrid recombinase module, while still minimizing the spatial separation between the modules in a manner that allows the TAL DBD module to stabilize the Flp variant module and enhance the recombinase activity and/or the target specificity of the Flp variant module.

Chimeric tyrosine recombinase architecture: As exemplified by Flp, the mode of binding of the Flp recombinase to its native recognition sequence, Flp Recombination Target (FRT), specifies the mode of binding of the chimeric Flp-TAL recombinase to its target (FIG. 1A): the Flp variant module binds to the inner segments of the target sequence, which constitutes the actual FRT-like sequence, while the TAL module binds the outer segments of the target sequence.

Analysis of the Flp/DNA and the TAL DBD/DNA complexes shows that the TAL module can be fused to either the C-terminus or to the N-terminus of the module Flp, thus creating two chimeric recombinase architectures: Flp-TAL and TAL-Flp (FIG. 1B). Both Flp-TAL and TAL-Flp are capable of binding to the head-to-tail and the tail-to-tail arrangements of the target sequences, provided the length of the linker that connects the modules is sufficiently long (FIG. 1B). However, in the compact modes of the Flp-TAL and TAL-Flp architectures (that is, when the linker that connects the modules is short) Flp-TAL is able to bind to the 'convenient' head-to-tail arrangement of the target sequence while TAL-Flp can bind to the 'inconvenient' tail-to-tail arrangements of the target sequences (FIG. 1B). The 'convenience' here is the property of the target sequence arrangement that describes (1) how easy it is to increase the length of the DNA sequence to which the TAL module binds without changing the length of the inter-modular linker and (2) how easy is to avoid steric clashes between the hybrid recombinase modules when the TAL module with longer C-terminal domains is used.

A module comprising a TAL DNA-binding domain is fused to the Flp variant module, either directly or through a linker. (FIG. 1C).

Linker: In certain embodiments of the invention, the chimeric Flp-TAL recombinase may optionally contain a linker between the Flp variant module and the TAL DBD module. When a linker is used, the linker may be positioned so as to connect the N terminus of the Flp variant module to the C terminus of the TAL DBD module. Alternatively, the linker may be positioned so as to connect the C terminus of the Flp variant module to the N terminus of the TAL DBD module. Generally, the latter configuration is easier to work with, as modifications to the N terminus of Flp are more likely to adversely affect recombinase activity. Any suitable linker may be used, as long as it does not reduce recombinase activity to such an extent that the chimeric enzyme is rendered non-functional in the desired system. In general, suitable linkers may be about 5 to about 20 amino acids in length, although linkers that are longer or shorter in length may also be used. A selection of suitable linkers are described, for example, in Akopian et al., Chimeric recombinases with designed DNA sequence recognition. Proc Natl Acad Sci USA 100(15):8688-8691 (2003).

NLS: In certain embodiments of the invention, the chimeric Flp-TAL recombinase may optionally include a heterologous nuclear localization signal (NLS). It is known that in certain instances, inclusion of a heterologous NLS may be advantageous and improve activity of the Flp variant. However, the native Flp enzyme, being of eukaryotic origen, naturally localizes to the nucleus. As such, a heterologous NLS is not required for proper functioning of the chimeric Flp-TAL recombinase.

An example of a chimeric Flp-TAL recombinase having a Flp variant domain, a linker, a TAL DBD and an NLS is shown in FIG. 10 (SEQ ID NO 37).

Codon optimization: In certain embodiments of the invention, it may be advantageous to perform codon optimization on all or part of the gene sequence encoding the chimeric Flp-TAL recombinase. Codon optimization is the process of modifying the coding region of a gene to more closely align the codon usage of a gene of interest with the codon usage frequency or codon bias of the target cell or organism, while retaining the same amino acid coding sequence. In some instances, codon optimization may improve translation efficiency. Numerous codon usage tables are publicly available and may be found, for example at https://www.genscript.com/tools/codon-frequency-tablem or https://www.kazusa.or.jp/codon/. See also Athey et al., A new and updated resource for codon usage tables, BMC Bioinformatics. 2017; 18: 391 (2017).

As noted above, genome engineering applications can utilize two versions of the Flp-TAL system that differ at the level of target specificity of the Flp variant modules: either strict or broad. In principle, the latter Flp variants (such as FV71 and/or other variants that can be evolved to have similar target selection functionality) can recognize a significant number if not the majority of the genomic FRT-like sequences. Therefore, the Flp-TAL system with such Flp variants can be quite convenient to use since only the TAL module needs to be engineered to target Flp-TAL recombinase to a new FRT-like sequence.

The efficiency of the integration and deletion reactions mediated by Flp-TAL: ~0.1% and ~10%, respectively, is comparable to that of wild-type Flp recombinase which lends confidence that the activity of Flp-TAL in dual recombinase-mediated cassette exchange (dual RMCE) will be also comparable to that of wild-type Flp.

Importantly, the deletion activity of Flp-TAL appears to be about two orders of magnitude higher than that shown for the hybrid serine recombinase recCas9 (Chaikind et al. (2016) A programmable Cas9-serine recombinase fusion protein that operates on DNA sequences in mammalian cells. Nucleic Acids Res 44(20):9758-9770). Moreover, no integration activity for recCas9 on the genomic targets was reported. Taken together, this demonstrates that the Flp-TAL system is a versatile genome engineering tool that can be significantly more active than other tailor-made target-specific recombination systems.

As the tyrosine recombinases have similar three-dimensional organization, similar mode of target binding, and are apparently well amenable to modification of their target specificity, other members of the tyrosine recombinase family can be also utilized to generate TAL-fused recombinases. These recombinases can greatly diversify the sequences that can be targeted by the TAL-fused recombination system, since each recombinase has its own set of target sequences in a genome. Moreover, different TAL-fused recombinases can be paired to perform dual RMCE to efficiently replace genome fragments. Importantly, the availability of several target-specific hybrid recombinases for dual RMCE would translate into shorter genome fragments that can be replaced: our analysis on the distribution of the target-like sequences for different recombinases in a genome shows that the arsenal of 5-6 hybrid recombinases is sufficient for reducing the size of the replaceable fragment to about 1 kb.

In the following examples, we demonstrate that chimeric target-specific Flp-TAL recombinases are a new versatile genome engineering tool that is able to recombine FRT-like sequences in their native genome environment. To our knowledge, this is the first demonstration of such activity for the target-specific variants of the tyrosine recombinases.

EXAMPLES

The invention may be better understood by reference to the following examples:

Using a simplified protein evolution approach, Flp variants for the chimeric Flp-TAL recombinase are evolved to recognize FRT-like sequences in the human β-globin gene. We examined the integration and deletion activity of the Flp-TAL recombinases in intact human HEK293 cells and demonstrated that only the chimeric Flp-TAL variants, but not the respective target-specific Flp variants, were able to efficiently perform these reactions. We also demonstrated that Flp variants with broad specificity toward FRT-like sequences can be fused to TAL DBDs of a desired target specificity, to direct the variant to new genomic target sequences. We estimate that the efficiency of the integration and deletion reactions mediated by the Flp-TAL variants is about 0.1% and 10%, respectively, which is comparable to that of wild-type Flp. Our results demonstrate that the present chimeric tyrosine recombinases are an attractive genome engineering platform.

Example 1: Selection of Genomic Target-Like Sequences

FRT-like sequences in the human genome are identified, essentially as described in Shultz et al. 2011.

Three FRT-like sequences located upstream of the human δ-globin gene and within the δ-globin and β-globin genes are selected, denoted FL-61 (SEQ ID NO 16), FL-63 (SEQ ID NO 17), and FL-71 (SEQ ID NO 18), respectively, which are separated from each other by 2.7 kb and ~7.5 kb, respectively (FIGS. 2A and B). These FRT-like sequences, as well as other genomic FRT-like sequences, can have several potential upstream and downstream TAL recognition sequences since the requirements for the TAL recognition sequences are quite relaxed—the only major prerequisite being a thymine at the position N−1 of the sequence: 5'T (Lamb B M, Mercer A C, & Barbas C F, 3rd (2013) Directed evolution of the TALE N-terminal domain for recognition of all 5' bases. Nucleic Acids Res 41(21):9779-9785).

We reasoned that to be useful in targeting Flp-TAL recombinases to the desired FRT-like sequences and yet to be easily manageable from the technical point of view, the TAL module should recognize a DNA sequence of about 9-24 bp, 12-24 bp, or 15-24 bp in length. We also reasoned that the TAL binding sequence should be separated from the recombinase binding element of the FRT-like sequence by 3 to 12 base pairs to avoid steric clashes between the hybrid recombinase modules or their significant spatial separation.

Additionally, we reasoned that the length of the TAL binding sequences should correlate with the degree of similarity between the Flp binding elements of the FRT-like sequence and that of FRT: the weaker the similarity, the longer the TAL recognition sequence.

Based on the above considerations, we decided to examine TAL binding sequences of 15 bp in length (except for the upstream 24-bp TAL binding site for FL-71) that are separated from FL-61 (SEQ ID NO 19), FL-63 (SEQ ID NO 20), and FL-71 (SEQ ID NO 21) by 4-5 bp (FIG. 2C)

Example 2: Evolution of Flp Variants with Strict and Relaxed Target Specificity

Previously we had evolved a number of Flp variants that recognize different genomic targets (Bolusani S, et al. (2006); Shultz J L, et al., (2011); (Shah et al. (2015)). In addition to unique mutations, these enzymes contain a group of mutations that is usually present in all variants. Without intending to be bound by a particular theory, we believe that these common mutations collectively relax the strict target specificity of Flp and allow it to recombine not only FRT but also FRT-like sequences. The unique mutations in these Flp variants either further relax or, in contrast, narrow the variant's target specificity.

The Flp variants that bear the common as well the unique mutations can be used to speed up the evolution of the Flp variants with target-specific or target-relaxed phenotypes if their genes are used as templates for generating shuffled variant libraries which can be screened to identify the desired target specificity. The pool of the template variant genes can be enhanced by including the library of the Flp genes that are randomized at codons 55, 58 and 59, since the amino acids at these positions contact the first four base pairs of the Flp binding elements of FRT that were shown to be the most critical for the Flp-FRT recognition (Shultz J L, et al., (2011)). Flp variants suitable for generating hybrid Flp-TAL recombinases, that is, those with relatively low activity and with strict or somewhat relaxed target specificity are evolved by one-two rounds of protein evolution using a pair of different but related recombination sequences: a genomic FRT-like sequence and FRT. Thus, Flp variants for the FL-61 FRT-like sequence are evolved using the recombining pair FL-61/FRT (SEQ ID NO 16/SEQ ID NO 12); Flp variants for the FL-63 FRT-like sequence are evolved using the recombining pair FL-63/FRT (SEQ ID NO 17/SEQ ID NO 12); and Flp variants for the FL-71 FRT-like sequence are evolved using the recombining pair FL-71/FRT (SEQ ID NO 18/SEQ ID NO 12). We then compared the activity of the evolved Flp variants on the FL-61 (SEQ ID NO 16), FL-63 (SEQ ID NO 17), and FL-71 (SEQ ID NO 18) sequences.

To identify Flp variants with the desired properties a screening system that is composed of the inversion and deletion reporters that are used sequentially was utilized (FIGS. 3A and B). The reporter cassettes in these vectors are flanked by the pair of the recombination sites that are arranged in the head-to-head and head-to-tail orientations, respectively. The inversion and deletion reporters have different purpose. The inversion reporter is used to identify a large pool of Flp variants that are able to recombine both the FRT-like sequence and FRT (SEQ ID NO 12); these variants are selected by amplifying the Flp variant genes in the inversion-positive configuration of the reporter (FIG. 3A). The deletion reporter is used to screen the inversion-positive library of the Flp variants that are sufficiently active to delete the reporter cassette in at least some vector molecules (FIG. 3B).

Inversion Experiments

A Flp variant library is constructed using Flp variants that bear both common and unique mutations, as well as Flp genes that are randomized at codons 55, 58, and 59, as templates for generating a shuffled Flp variant library. The shuffled Flp variant library is then ligated into an inversion reporter (a derivative of pBAD33) and transformed into bacterial cells and incubated with the inducer L-arabinose at the final concentration 0.1% for 2.5 hours. The transformed cells (0.3 ml) are then transferred into 20 ml of LB medium supplemented with chloramphenicol (35 µg/ml) and incubated overnight. The reporter plasmids are then isolated and subjected to the PCR analysis to identify those Flp variants that are able to invert the reporter.

The reporter contains the inversion cassette flanked by the recombination targets in the head-to-head orientation: FL-61, FL-63, or FL-71 (marked as RT) and FRT* that bears the spacer either from FL-61, FL-63, or FL-71, respectively. Upon expression of a recombination competent Flp variant, the cassette is inverted so the gene that encodes this variant can be amplified. (FIG. 3A).

Deletion Experiments

The deletion experiments are performed essentially as described in Voziyanov et al., 2002. In brief, the Flp variant library (from the example above) is transformed into bacterial cells that harbor the deletion reporter (a derivative of pBAD24 (Guzman et al. (1995) Tight regulation, modulation, and high-level expression by vectors containing the arabinose PBAD promoter. J Bacteriol 177(14):4121-4130)). After incubating the transformed cells with the inducer L-arabinose at the final concentration 0.1% for 2.5 hours, the cells are plated onto LB/agar plates that contained X-gal to visualize the colonies in which the deletion of the lacZα cassette has occurred. (FIG. 3B).

The deletion reporter has the lacZα cassette flanked by the recombination targets in the head-to-tail orientation. If a Flp variant is able to delete the cassette, the resulting bacterial cells will form white colonies when plated on the X-gal containing plates. (FIG. 3D).

The screen of the library of the shuffled Flp variant genes that bear the desired set of mutations using the respective inversion and deletion reporters identified several Flp variants that were able to recombine the FL-61/FRT (SEQ ID NO 16/SEQ ID NO 12), FL-63/FRT (SEQ ID NO 17/SEQ ID NO 12), and FL-71/FRT (SEQ ID NO 18/SEQ ID NO 12) pairs with reasonable efficiency. The variants that demonstrated the highest activity on their respective recombination pairs were named FV61, FV63, and FV71 and tested for their ability to recombine all three FRT-like sequences to identify the variants with either strict or broad target specificity (FIGS. 3D and E).

Figure 3D:
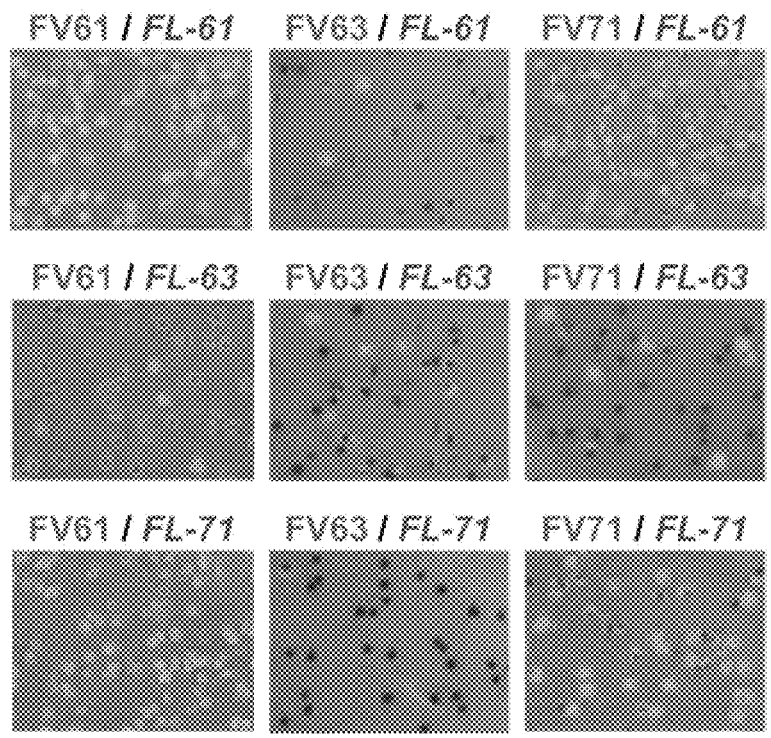
Figure 3E:
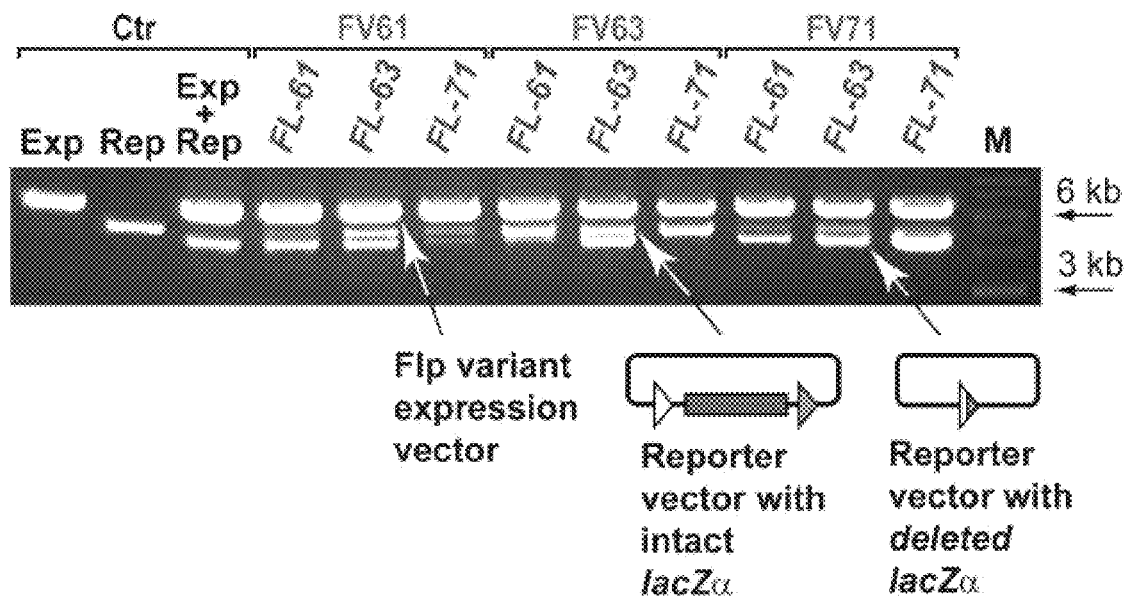

FV61, FV63, and FV71 responded differently when they were challenged with the 'non-cognate' FRT-like sequences (FIGS. 3D and E). FV63 was the most specific and was able to recombine with the reasonable efficiency only the FL-63 sequence; some minor recombination activity was seen on FL-61 but the recombination activity on FL-71 was barely detectable. FV71 was the least specific and was able to recombine all three FRT-like sequences. FV61 was also able to recombine FL-61, FL-63, and FL-71 but we noticed abnormalities in its phenotype: the pale blue colonies in the experiments with all FRT-likes sequences (FIG. 3D) and the faint reporter bands in the FL-71 experiments (both unrecombined and recombined, FIG. 3E); these abnormalities apparently indicate that FV61 binds to DNA (or just to the FRT-like sequences) tighter than do FV63 and FV71. Off note, our evolution experiments sometimes generate Flp variants with the FV61-like phenotype.

The mutational profile of FV61, FL63, and FV71 is shown in FIG. 3C. As anticipated, these Flp variants bear a group of common mutations at positions 45, 50, 114, 295, and 363. In addition, each variant has a set of unique mutations, some of which were seen before in other target-specific Flp variants (positions 44, 62, 130, 173, 176, 193, and 324) while the other unique mutations are new (positions 3, 18, 75, 85, 157, 171, 213, and 290). In addition, FV61 and FV63 have the same set of mutations at positions 55, 58, and 59 which is different from that of FV71. We also noted that the profile of mutations in FV61, FL63, and FV71 is different from that of the Flp variants that were evolved to recombine FL-61, FL-63, and FL-71 (individually, rather than against the combinations FRT/FL-61, FRT/FL063, or FRT/FL-71) (Shultz et al. (2011)).

Note: All bacterial experiments were performed using *E. coli* strain NEB 10-beta from New England Biolabs: araD139 Δ(ara-leu)7697 fhuA lacX74 galK (φ80 Δ(lacZ) M15) mcrA galU recA1 endA1 nupG rpsL (StrR) Δ(mrr-hsdRMS-mcrBC).

Example 3: Flp-TAL Variants can Integrate a Reporter into the Desired Locations in the Human Genome As noted, FL-61 (SEQ ID NO 16), FL-63 (SEQ ID NO 17), and FL-71 (SEQ ID NO 18) each have several potential TAL DBD upstream and downstream of these sites. Since it was reasoned that the TAL DBD should be separated from each FRT-like sequence by about 3-12 to avoid steric clashes between the hybrid recombinase module while still minimizing the separation so as to bet the most substantial benefit of the TAL DBD stabilizing the recombinase module on the FRT-like site, TAL DBD's are programmed to be specific for sequences separated from FL-61, FL-63, and FL-71 by 4-5 bp (FIG. 2C) (SEQ ID NO 19, SEQ ID NO 20, SEQ ID NO 21). Sequences of 15 bp in length upstream and downstream of each of the sites are selected, with the exception of the sequence upstream from FL-71. A longer sequence of 24 bp is chosen for the latter TAL DBD. Sequences of 15 and 18 bp were also tested for the upstream sequences of FL-71.

(SEQ ID NO 44 and SEQ ID NO 45). These sequences performed as well as the longer 24 bp sequence.

Figure 1B:
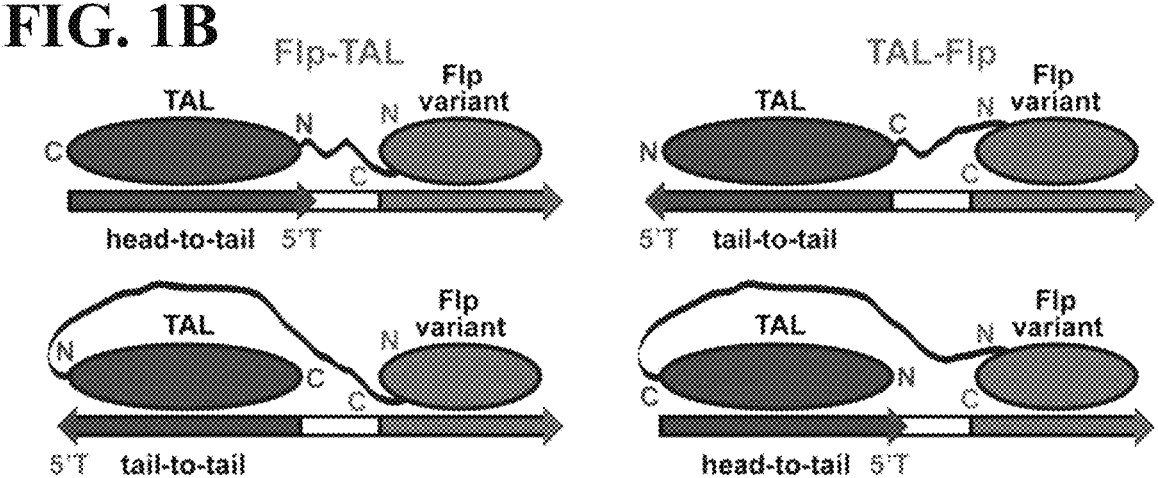
Figure 1C:
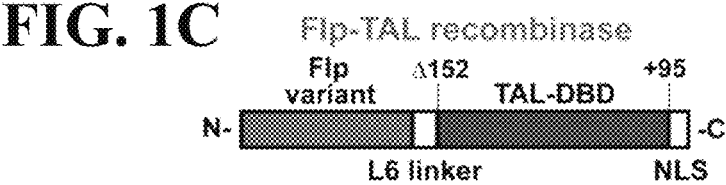
FIG. 1C shows an example schematic of a Flp-TAL recombinase.

To demonstrate that Flp-TAL recombinases are capable of targeting FRT-like sequences in their native environment, we fused the FV61, FV63, and FV71 variants with their respective TAL modules (FIGS. 1A and 2C). Since the TAL modules in the Flp-TAL recombinase have to be specific for both upstream and downstream TAL recognition sequences of the FRT-like sequence, two Flp-TAL variants for each fusion recombinase were engineered: Flp-TAL(L) and Flp-TAL(R), FIG. 1A. For the sake of simplicity, the left and the right Flp-TAL variants of FV61, FV63, and FV71 are collectively called FV61-TAL, FV63-TAL, and FV71-TAL, respectively.

TAL DBD's are programmed using the Golden Gate TALEN kit, following the procedure of Cermak et al. (2011). Following the known rules, where the repeat variable di-residues (RVD) HD, NI, NG, and NN encode for binding to C, A, T, and G, respectively, 15 tandem repeats are assembled for the sequences upstream and downstream (left and right) of FL-61 (SEQ ID NO 22) (SEQ ID NO 23) and FL-63 (SEQ ID NO 24) (SEQ ID NO 25) and downstream of FL-71 (SEQ ID NO 27), as denoted in FIG. 2C. 24 tandem repeats are assembled to be specific for the 24 bp upstream of FL-71 (SEQ ID NO 26). These TAL DBD's are referred to as FL-61_TAL(L) (SEQ ID NO 28), FL-61_TAL(R) (SEQ ID NO 29), FL-63_TAL(L) (SEQ ID NO 30), FL-63_TAL(R) (SEQ ID NO 31), FL-71_TAL(L) (SEQ ID NO 32), FL-71_TAL(R) (SEQ ID NO 33), respectively.

Mammalian cell experiments were performed in human embryonic kidney HEK-293 cells (ATCC, CRL-1573) which were propagated in EMEM medium. Cell transfections were performed using DNA-In (Molecular Transfer) or Turbo293 reagents (Speed BioSystems).

Flp and Flp-TAL variants were expressed from the pOG100 vector (a derivative of pOG44 (Anderson et al. (2012) Flp and Cre expressed from Flp-2A-Cre and Flp-IRES-Cre transcription units mediate the highest level of dual recombinase-mediated cassette exchange. Nucleic Acids Res 40(8):e62.). The pTarget reporter is a derivative of the pDNA3 vector (Invitrogen).

The experiments to integrate pTarget into FL-61 (SEQ ID NO 16), FL-63 (SEQ ID NO 17), and FL-71 (SEQ ID NO 18) were performed as follows. HEK-293 cells were co-transfected, in 24-well plates, with pTarget (0.4 μg) and the respective pOG100-FV-TAL vector (1 μg). 48 hours post-transfection, 1/10 of the cells were transferred into 6-well plate containing EMEM medium supplemented with hygromycin (550 mg/l). About 10 days later, all hygromycin resistant colonies were pooled and analyzed by PCR and sequencing. Alternatively, individual red (FV61-TAL and FV63-TAL experiments) or green (FV71-TAL experiments) colonies were transferred into 48-well plate, expanded and analyzed.

The deletion experiments were performed by transfecting the respective cells in 24-well plates with pOG100-FV71-TAL (1 μg). 48 hours post transfection, all cells were transferred into 6-well plates, allowed to become confluent, collected, and analyzed by PCR and sequencing.

The targeting activity of the hybrid Flp-TAL recombinases were analyzed via integration and deletion assays (FIGS. 4 and 5). The schematic of the integration assay is shown in FIG. 4A. The reporter vector pTarget bears three transcriptional units that express EGFP, hygromycin B phosphotransferase (hygroR), and DsRed. In this reporter, the hybrid FRT/FL-61 (SEQ ID NO 34) (or FRT/FL-63 (SEQ ID NO 35)) site is located between the CMV promoter and the EGFP gene while the hybrid FRT/FL-71 site is positioned between the EF1α promoter and the DsRed gene (SEQ ID NO 36). (FIG. 8).

Figure 4A:
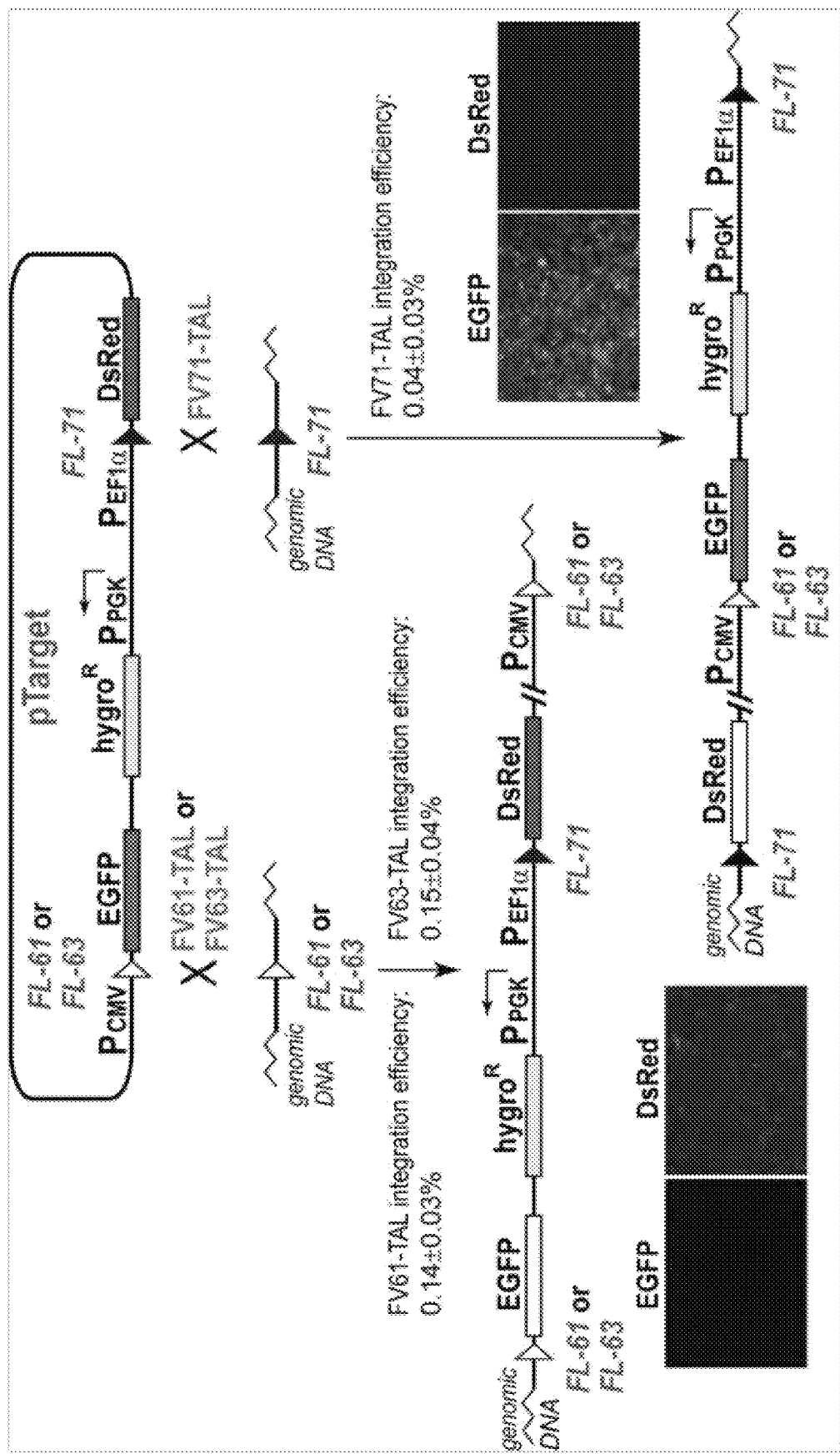
FIG. 4A to FIG. 4E: Flp-TAL variants can target FL-61, FL-63, and FL-71 in unmodified HEK-293 cells.

If FV61-TAL (or FV63-TAL) integrates pTarget into the native FL-61 (SEQ ID NO 16) (or FL-63 (SEQ ID NO 17)) sequence, the EGFP gene loses its promoter and thus cannot be expressed. The resultant cells should be therefore red and not green (FIG. 4A). Alternatively, if FV71-TAL is capable of integrating pTarget into the native FL-71 sequence (SEQ ID NO 18), the DsRed gene loses its promoter and cannot be expressed. The resultant cells should be therefore just green (FIG. 4A).

To demonstrate the integration activity of the Flp-TAL recombinases, we co-transfected HEK293 cells with the pTarget reporter and the vectors that express FV61-TAL, FV63-TAL, or FV71-TAL. 48 hours post-transfection, ⅒ of the cells were transferred into medium supplemented with hygromycin and incubated for about 10 days until the hygroR colonies are formed. Four types of colonies were observed: with no color, green and red, just green, and just red. We did not note apparent differences in the ratios of these colony types in the experiments with FV61-TAL, FV63-TAL, and FV71-TAL.

Figure 4B:
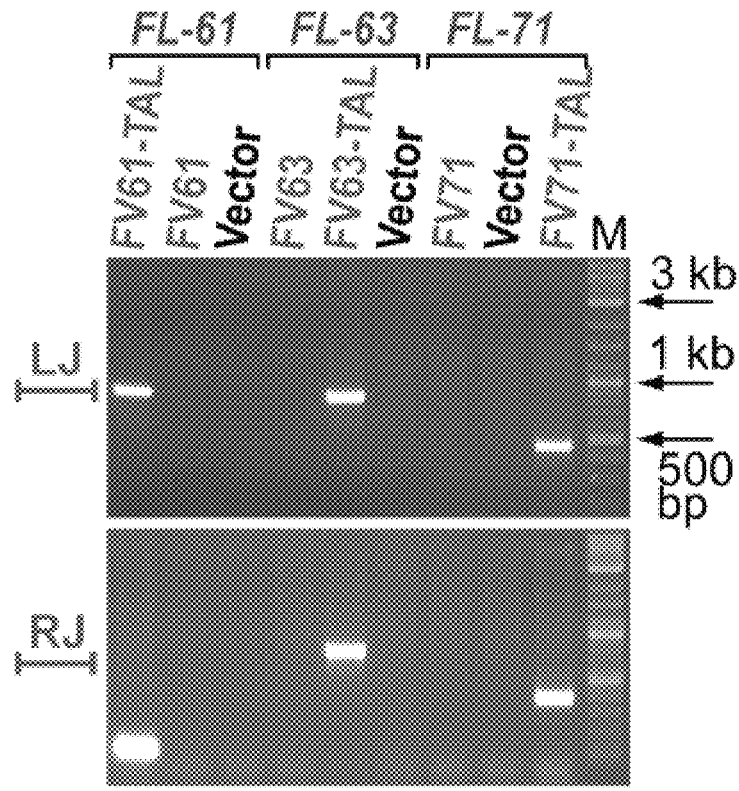
Figure 4C:
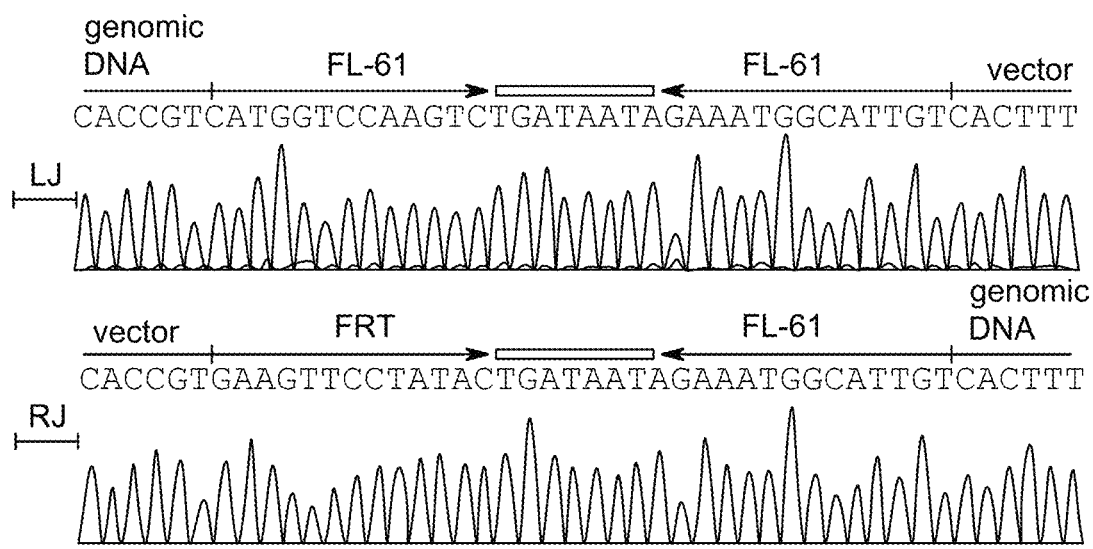
Figure 4D:
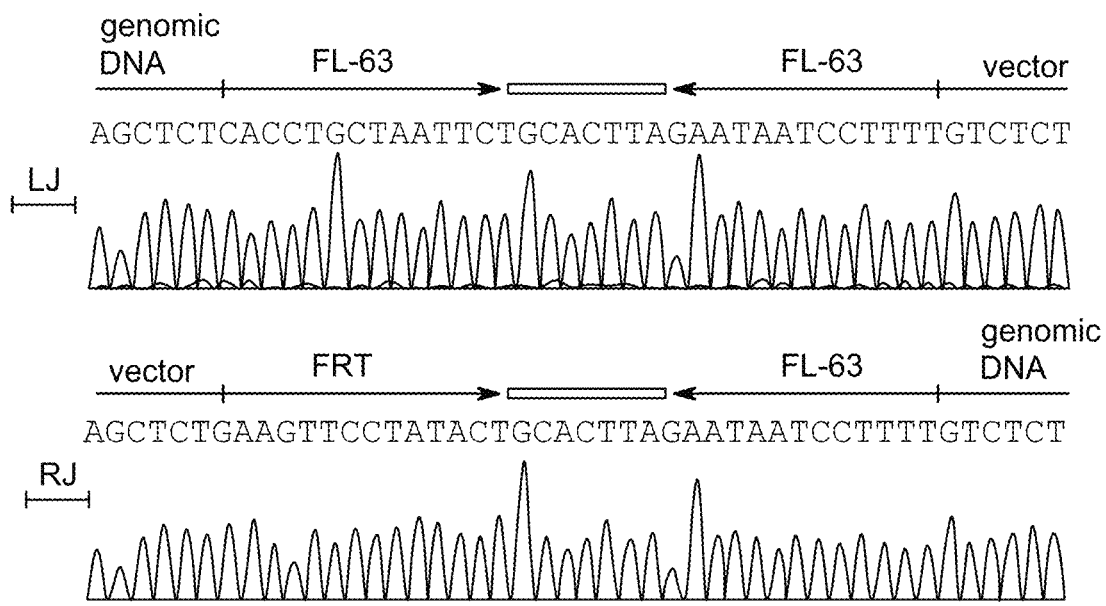
Figure 4E:
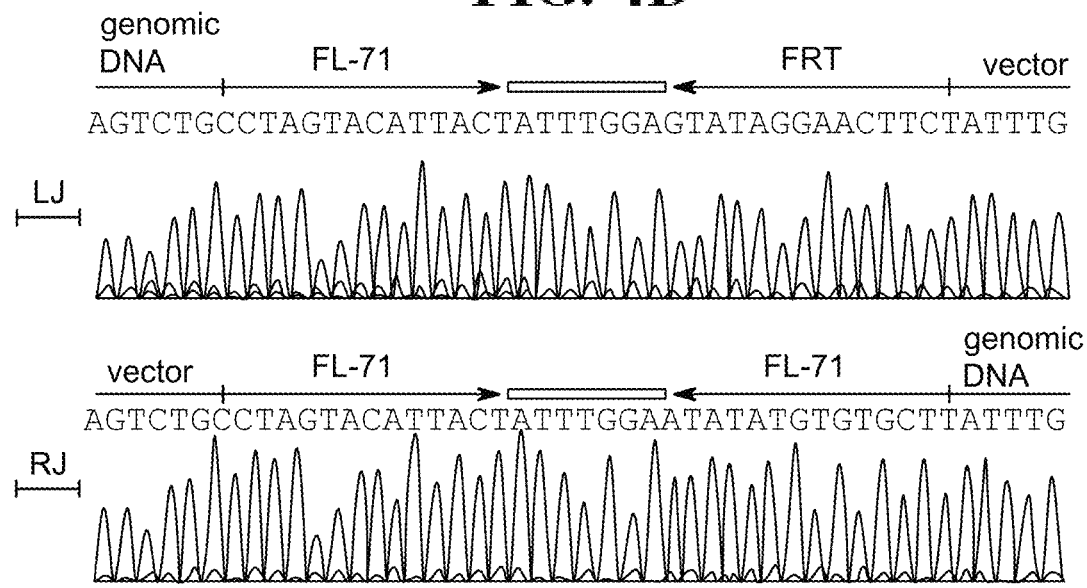

To demonstrate that the Flp-TAL recombinases are capable of integrating the reporter into the desired FRT-like sequences, the hygromycin resistant colonies were pooled and their genomic DNA isolated and subjected to the PCR analysis, which confirmed the correct integration events (FIG. 4B).

Importantly, the control experiments with the 'plain' (i.e., lacking a TAL DBD) Flp variants FV61, FV63, and FV71 did not yield detectable integration of the reporter into the respective genomic FRT-like sequences.

To determine the efficiency of integration, we performed a series of integration experiments as described above but instead of pooling all hygromycin resistance colonies we expanded only either just red colonies (FV61-TAL and FV63-TAL experiments) or just green colonies (FV71-TAL experiments) and subjected them to the PCR analysis. These experiments revealed that the hybrid recombinases integrated the reporter vector, on average, in about 0.1% of the transfected cells (although the efficiency of integration into FL-61 (SEQ ID NO 16) and FL-63 (SEQ ID NO 17) was about three times higher than into FL-71) (SEQ ID NO 18).

Example 4: FV71 can Recombine Different FRT-Like Sequences in the Human Genome when Fused to the TAL Modules with the Respective Target Specificity We next examine whether FV71, which was able to recombine different FRT-like sequences in bacteria (FIGS. 3E and D), could also recombine these sequences in their native genome environment. For this, we fused FV71 with the respective TAL modules that are specific for either FL-61 or FL-63 (FIG. 2C) to obtain the FV71-TAL61 and FV71-TAL63 variants, respectively. We then performed the integration experiments as described in the previous section and found that FV71-TAL61 and FV71-TAL63 were able to target FL-61 and FL-63 as efficiently as did FV61-TAL and FV63-TAL (FIG. 4).

In parallel, we also tested whether FV61, which showed an apparent tight binding phenotype in bacterial cells (FIGS. 3E and D), was able to target FL-71 if fused to the respective TAL module. Despite extensive experimenting we were unable to detect FV61-TAL71-mediated integration of the reporter vector into FL-71.

Example 5: Flp-TAL Recombinases can Delete Genome Fragments

Finally, we examined the ability of the Flp-TAL recombinases to delete large genome fragments. In these experiments we utilized the property of the targeting vector to bear two different FRT-like sequences (FIG. 4A). Upon integration of the vector into one of the respective genomic FRT-like sequences, the other vector-borne FRT-like sequence can be used to delete the DNA fragment that is located between this sequence and the corresponding genomic FRT-like sequence (FIG. 5A).

In the deletion assays we used the expanded integration-positive red cells that were obtained in the FV61-TAL integration experiments (FIG. 5). These cells were transfected with the vector that expresses the FV71-TAL recombinase and then expanded and subjected to the PCR analysis to assess the ratio of the cells, in which the 14.7 kb DNA fragment was deleted. The analysis of the sequentially diluted genomic DNA (Chaikind et al. A programmable Cas9-serine recombinase fusion protein that operates on DNA sequences in mammalian cells. Nucleic Acids Res 44, 9758-9770, doi:10.1093/nar/gkw707 (2016)) revealed that the deletion occurred, on average, in about 10% of the transfected cells.

Example 6: Evolution of iCre Variant Having Relaxed Target Specificity

Essentially as described in Example 2 above, iCre variants with relaxed target specificity are evolved using loxP (SEQ ID NO 13) and the lox-like target sequence 69058 (LL-69) (SEQ ID NO 46). One particular clone is selected for further characterization and experimentation. The variant contains an amino acid R to M substitution at position 32 of iCre (SEQ ID NO 4), which corresponds to an R to M substation at position 24 of wild-type Cre. The iCre variant is referred to herein as iCreM24 (SEQ ID NO 38) (SEQ ID NO 39).

Chimeric tyrosine recombinases using iCreM24 as the recombinase module are then constructed, as described above, using different TAL DBD modules designed to target potential TAL binding sites near LL-69 (SEQ ID NO 41) (SEQ ID NO 42) (SEQ ID NO 43). (FIG. 12) Each were successfully tested in CHO cells, essentially as described above. TAL/L15-TAL/R12_1 (SEQ ID NO 41) was recombined by the mixture of two variants: iCreM24-TAL(L15-1) and iCreM24-TAL(R12); TAL/L15-TAL/R15_2 (SEQ ID NO 42) was recombined by the mixture of two variants: iCreM24-TAL(L15-2) and iCreM24-TAL(R15); and TAL/L15-TAL/R12_2 (SEQ ID NO 43) was recombined by the mixture of two variants: iCreM24-TAL(L15-2) and iCreM24-TAL(R12). The chimeric Cre-TAL recombinase pairs directed to LL-69 are referred to collectively as Cre69-TAL.

A partial sequence of a CreM24-TAL chimeric recombinase is shown in FIG. 13. (SEQ ID NO 40). Note that in this instance, the TAL DBD module begins at position delta-117. The additional TAL sequence is believed to function as a longer linker. In general, chimeric Cre-TAL recombinases appear to function better with longer linker sequences than Flp-TAL recombinases. Without intending to be bound by any particular theory, it is believed that this is related to the differences in the 3D structures of Flp and Cre. In Flp, the C-terminus is closer to the 5'-end of the recombinase binding sequence than that of Cre.

Example 7: Dual RMCE Mediated by Cre-TAL and Flp-TAL

Figure 14A:
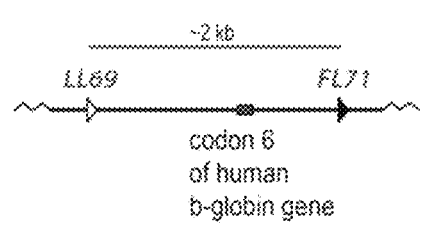
FIG. 14A to FIG. 14B: Dual RMCE mediated by Cre-TAL and Flp-TAL variants CV69 and FV71.
Figure 14B:
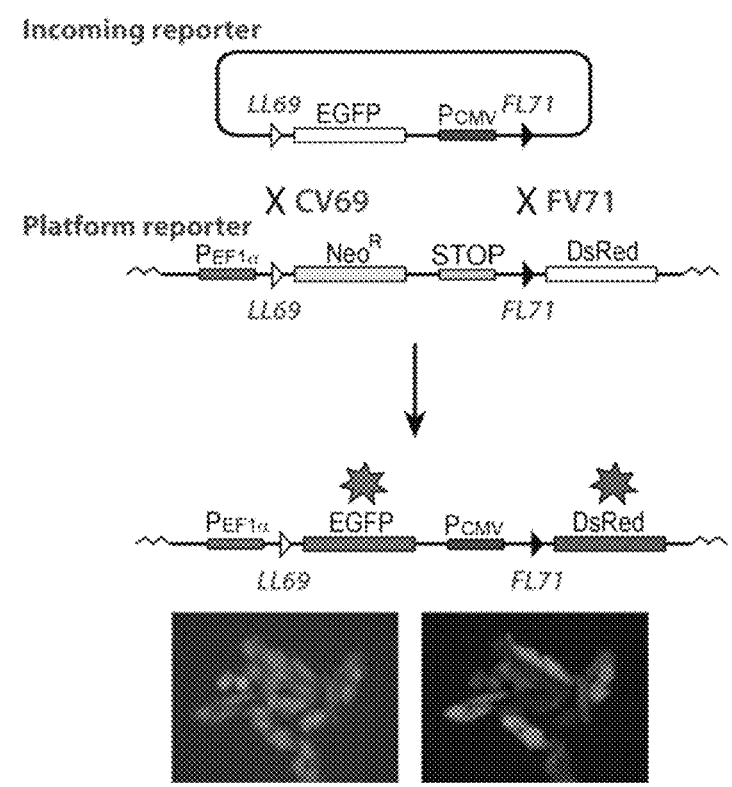

To monitor the activity of Flp71-TAL and Cre69-TAL during dual RMCE, we have constructed a set of two reporter plasmids that, via activating the expression of two different fluorescent markers, can assess the efficiency of a replacement reaction catalyzed by the hybrid recombinases in the absence of a selection force (FIG. 14B). One of the two reporter plasmids serves as a platform that is integrated into an actively transcribed locus of the CHO genome, and the other is an incoming reporter.

The reporter cassette in the platform plasmid p1372/69-71 contains the NeoR gene under the control of the EF1α promoter. The NeoR gene is followed by the transcription terminator STOP (Sauer, B. (1993) Manipulation of transgenes by site-specific recombination: use of Cre recombinase. Methods Enzymol, 225, 890-900)) and the promoterless DsRed gene. The Cre69-TAL cognate sequence LL-69 (SEQ ID NO 46) is located between the EF1α promoter and the NeoR gene; the Flp71-TAL cognate sequence FL-71 (SEQ ID NO 18) is located between STOP and the DsRed gene. The platform reporter p1372/69-71, which is a derivative of the pcTD plasmid of the TD-In system (Anderson et al. (2012) Flp and Cre expressed from Flp-2A-Cre and Flp-IRES-Cre transcription units mediate the highest level of dual recombinase-mediated cassette exchange. Nucleic Acids Res, 40, e62.), was integrated into the TDRT site located in the genome of the CHO TD-In cells using the TD-40 variant of TD recombinase to obtain the CHO-1372/69-71 cell line. The incoming plasmid p1345/69-71 carries a reporter cassette composed of the promoterless EGFP gene followed by the CMV promoter. LL-69 and FL-71 that can recombine with their counterparts in the plasmid p1372/69-71, flank the EGFP-CMV reporter cassette (FIG. 14A).

Cre69-TAL-catalyzed recombination between the LL-69 sites located on the platform and the incoming reporters leads to the swap between the NeoR and the EGFP genes and therefore activates the expression of the EGFP gene (FIG. 14B). Flp71-TAL-catalyzed recombination between the FL-71 sites leads to the swap between the transcription terminator STOP and the CMV promoter thus activating the expression of the DsRed gene (FIG. 14B).

A dual RMCE reaction between the reporter cassettes located in the incoming and the platform plasmids is catalyzed by a simultaneous supply of both Cre69-TAL and Flp71-TAL recombinases (FIG. 14B). Successful dual RMCE is expected to replace the NeoR-STOP cassette in the integrated platform reporter with the EGFP-CMV cassette in the incoming plasmid. As a result, the expression of both EGFP and DsRed genes is activated which can be detected by the appearance of cells that are both green and red (FIG. 14B).

Construction of CHO-1372/69-71 cell line

To construct CHO-1372/69-71 cell line, CHO TD-In cells were co-transfected with the platform reporter p1372/69-71 and pOG-TD1-40 (Anderson et al. (2012)), which expresses the TD1-40 variant of the TD recombinase (Blaisonneau, et al. (1997) A circular plasmid from the yeast *Torulaspora delbrueckii*. Plasmid, 38, 202-209.). 48 hours post-transfection, ⅙ of the cells were transferred into a 100 mm plate into the medium supplemented with hygromycin. After about 10 days, several hygromycin resistant colonies were transferred into 96-well plate and their sensitivity to zeocin and neomycin was tested. The colonies that were sensitive to zeocin and resistant to neomycin were used in the RMCE experiments.

Recombinase-Mediated Cassette Exchange Experiments

Dual RMCE experiments were performed by transfecting the platform CHO-1372/69-71 cells with the incoming reporter p1372/69-71 and both expression vectors: Cre69-TAL and Flp71-TAL. 48 hours post transfection, ⅙ of the cells were transferred into 6-well plates, the cells were allowed to become confluent, and the number of the green, red, and green-red colonies was counted. Several colonies that were both green and red were expanded and analyzed. The efficiency of the replacement reaction was about 0.01-0.03%.

REFERENCES

1. Miller J C, et al. (2011) A TALE nuclease architecture for efficient genome editing. Nat Biotechnol 29(2):143-148.
2. Cong L, et al. (2013) Multiplex genome engineering using CRISPR/Cas systems. Science 339(6121):819-823.
3. Komor A C, Kim Y B, Packer M S, Zuris J A, & Liu D R (2016) Programmable editing of a target base in genomic DNA without double-stranded DNA cleavage. Nature 533(7603):420-424.
4. Kim Y B, et al. (2017) Increasing the genome-targeting scope and precision of base editing with engineered Cas9-cytidine deaminase fusions. Nat Biotechnol 35(4): 371-376.
5. Grindley N D, Whiteson K L, & Rice P A (2006) Mechanisms of site-specific recombination. Annual review of biochemistry 75:567-605.
6. Buchholz F & Stewart A F (2001) Alteration of Cre recombinase site specificity by substrate-linked protein evolution. Nat Biotechnol 19(11):1047-1052.
7. Sarkar I, Hauber I, Hauber J, & Buchholz F (2007) HIV-1 proviral DNA excision using an evolved recombinase. Science 316(5833):1912-1915.
8. Bolusani S, et al. (2006) Evolution of variants of yeast site-specific recombinase Flp that utilize native genomic sequences as recombination target sites. Nucleic Acids Res 34(18):5259-5269.
9. Shultz J L, Voziyanova E, Konieczka J H, & Voziyanov Y (2011) A genome-wide analysis of FRT-like sequences in the human genome. PLoS One 6(3):e18077.
10. Guo F, Gopaul D N, & van Duyne G D (1997) Structure of Cre recombinase complexed with DNA in a site-specific recombination synapse. Nature 389(6646):40-46.
11. Chen Y, Narendra U, Iype L E, Cox M M, & Rice P A (2000) Crystal structure of a Flp recombinase-Holliday junction complex: assembly of an active oligomer by helix swapping. Mol Cell 6(4):885-897.
12. Karpinski J, et al. (2016) Directed evolution of a recombinase that excises the provirus of most HIV-1 primary isolates with high specificity. Nat Biotechnol 34(4):401-409.
13. Shah R, Li F, Voziyanova E, & Voziyanov Y (2015) Target-specific variants of Flp recombinase mediate genome engineering reactions in mammalian cells. The FEBS journal 282(17):3323-3333.
14. Akopian A, He J, Boocock M R, & Stark W M (2003) Chimeric recombinases with designed DNA sequence recognition. Proc Natl Acad Sci USA 100(15):8688-8691.

15. Gordley R M, Smith J D, Graslund T, & Barbas C F, 3rd (2007) Evolution of programmable zinc finger-recombinases with activity in human cells. J Mol Biol 367(3): 802-813.
16. Mercer A C, Gaj T, Fuller R P, & Barbas C F, 3rd (2012) Chimeric TALE recombinases with programmable DNA sequence specificity. Nucleic Acids Res 40(21):11163-11172.
17. Chaikind B, Bessen J L, Thompson D B, Hu J H, & Liu D R (2016) A programmable Cas9-serine recombinase fusion protein that operates on DNA sequences in mammalian cells. Nucleic Acids Res 44(20):9758-9770.
18. Kim Y G, Cha J, & Chandrasegaran S (1996) Hybrid restriction enzymes: zinc finger fusions to Fok I cleavage domain. Proc Natl Acad Sci USA 93(3):1156-1160.
19. Christian M, et al. (2010) Targeting DNA double-strand breaks with TAL effector nucleases. Genetics 186(2):757-761.
20. Porteus M H & Carroll D (2005) Gene targeting using zinc finger nucleases. Nat Biotechnol 23(8):967-973.
21. Urnov F D, et al. (2005) Highly efficient endogenous human gene correction using designed zinc-finger nucleases. Nature 435(7042):646-651.
22. Miller J C, et al. (2007) An improved zinc-finger nuclease architecture for highly specific genome editing. Nat Biotechnol 25(7):778-785.
23. Cermak T, et al. (2011) Efficient design and assembly of custom TALEN and other TAL effector-based constructs for DNA targeting. Nucleic Acids Res 39(12):e82.
24. Gaj T, Gersbach C A, & Barbas C F, 3rd (2013) ZFN, TALEN, and CRISPR/Cas-based methods for genome engineering. Trends Biotechnol 31(7):397-405.
25. Mak A N, Bradley P, Cernadas R A, Bogdanove A J, & Stoddard B L (2012) The crystal structure of TAL effector PthXo1 bound to its DNA target. Science 335(6069):716-719.
26. Lamb B M, Mercer A C, & Barbas C F, 3rd (2013) Directed evolution of the TALE N-terminal domain for recognition of all 5' bases. Nucleic Acids Res 41(21): 9779-9785.
27. Guzman L M, Belin D, Carson M J, & Beckwith J (1995) Tight regulation, modulation, and high-level expression by vectors containing the arabinose PBAD promoter. J Bacteriol 177(14):4121-4130.
28. Voziyanov Y, Stewart A F, & Jayaram M (2002) A dual reporter screening system identifies the amino acid at position 82 in Flp site-specific recombinase as a determinant for target specificity. Nucleic Acids Res 30(7): 1656-1663.
29. Anderson R P, Voziyanova E, & Voziyanov Y (2012) Flp and Cre expressed from Flp-2A-Cre and Flp-IRES-Cre transcription units mediate the highest level of dual recombinase-mediated cassette exchange. Nucleic Acids Res 40(8):e62.

Although the present invention has been described in terms of the preferred embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention. Each or the documents cited herein are incorporated by reference in their entirety.

What is claimed is:

1. A nucleic acid encoding a non-naturally occurring chimeric Flp-TAL recombinase comprising a regulatory element operable in a target cell, said regulatory element operably linked to a nucleic acid sequence encoding a chimeric Flp-TAL recombinase having a Flp recombinase variant domain and a TAL DNA-binding domain, wherein said chimeric Flp-TAL recombinase has a more narrow or more broad target specificity for FRT-like target sequences, relative to wild-type Flp recombinase.

2. A method of altering a target sequence in the genome of a target cell that comprises introducing into the target cell and expressing a chimeric Flp-TAL recombinase nucleic acid system, said system comprising at least one nucleic acid vector having
   a) a first regulatory element operable in said target cell, said first regulatory element operably linked to a nucleotide sequence encoding a first chimeric Flp-TAL recombinase protein, said first chimeric Flp-TAL recombinase protein comprising a first Flp recombinase variant domain, a first linker peptide, and a first TAL DNA-binding domain, where the first linker peptide operably connects the first Flp recombinase variant domain to the first TAL DNA-binding domain, wherein said first chimeric Flp-TAL recombinase has a more narrow or more broad target specificity for FRT-like target sequences, relative to wild-type Flp recombinase, and
   b) a second regulatory element operable in said target cell, said second regulatory element operably linked to a nucleotide sequence encoding a second chimeric Flp-TAL recombinase protein, said second chimeric Flp-TAL recombinase protein comprising a second Flp recombinase variant domain, a second linker peptide, and a second TAL DNA binding domain, where the second linker peptide operably connects the second Flp recombinase variant domain to the second TAL DNA-binding domain, wherein said second chimeric Flp-TAL recombinase has a more narrow or more broad target specificity for FRT-like target sequences, relative to wild-type Flp recombinase, wherein said first TAL DNA-binding domain targets a nucleic acid sequence upstream of the target sequence and said second TAL DNA-binding domain targets a nucleic acid sequence downstream of the target sequence forming a nucleic acid-protein complex, whereby the target nucleic acid sequence in the cell is altered.

* * * * *

SEQUENCE LISTING

```
Sequence total quantity: 73
SEQ ID NO: 1            moltype = DNA  length = 1272
FEATURE                 Location/Qualifiers
misc_feature            1..1272
                        note = Thermostable derivitive of wild-type Flp.
source                  1..1272
                        mol_type = other DNA
                        organism = synthetic construct
SEQUENCE: 1
atgtcacaat ttgatatatt atgtaaaaca ccacctaagg tcctggttcg tcagtttgtg   60
gaaaggtttg aaagaccttc aggggaaaaa atagcatcat gtgctgctga actaacctat  120
ttatgttgga tgattactca taacggaaca gcaatcaaga gagccacatt catgagctat  180
aatactatca taagcaattc gctgagtttc gatattgtca acaaatcact ccagtttaaa  240
tacaagacgc aaaaagcaac aattctggaa gcctcattaa agaaattaat tcctgcttgg  300
gaatttacaa ttattcctta caatggacaa aaacatcaat ctgatatcac tgatattgta  360
agtagtttgc aattacagtt cgaatcatcg gaagaagcag ataagggaaa tagccacagt  420
aaaaaaatgc ttaaagcact tctaagtgag ggtgaaagca tctgggagat cactgagaaa  480
atactaaatt cgtttgagta tacctcgaga tttacaaaaa caaaactttt ataccaattc  540
ctcttcctag ctactttcat caattgtgga agattcagcg atattaagaa cgttgatccg  600
aaatcattta aattagtcca aaataagtat ctgggagtaa taatccagtg tttagtgaca  660
gagacaaaga caagcgttag taggcacata tacttcttta gcgcaagggg taggatcgat  720
ccacttgtat atttggatga attttttgagg aattctgaac cagtcctaaa acgagtaaat  780
aggaccggca attcttcaag caacaaacag gaataccaat tattaaaaga taacttagtc  840
agatcgtaca acaaggcttt gaagaaaaat gcgccttatc caatctttgc tataaagaat  900
ggcccaaaat ctcacattgg aagacatttg atgacctcat ttctgtcaat gaagggccta  960
acggagttga ctaatgttgt gggaaattgg agcgataagc gtgcttctgc cgtggccagg 1020
acaacgtata ctcatcagat aacagcaata cctgatcact acttcgcact agtttctcgg 1080
tactatgcat atgatccaat atcaaaggaa atgatagcat tgaaggatga gactaatcca 1140
attgaggagt ggcagcatat agaacagcta aagggtagtg ctgaaggaag catacgatac 1200
cccgcatgga atgggataat atcacaggag gtactagact acctttcatc ctacataaat 1260
agacgcatat aa                                                     1272

SEQ ID NO: 2            moltype = AA  length = 423
FEATURE                 Location/Qualifiers
REGION                  1..423
                        note = Amino acid sequence of the thermostable varient of
                        Flp, Flpe.
```

```
source                       1..423
                             mol_type = protein
                             organism = synthetic construct
SEQUENCE: 2
MSQFDILCKT PPKVLVRQFV ERFERPSGEK IASCAAELTY LCWMITHNGT AIKRATFMSY    60
NTIISNSLSF DIVNKSLQFK YKTQKATILE ASLKKLIPAW EFTIIPYNGQ KHQSDITDIV   120
SSLQLQFESS EEADKGNSHS KKMLKALLSE GESIWEITEK ILNSFEYTSR FTKTKTLYQF   180
LFLATFINCG RFSDIKNVDP KSFKLVQNKY LGVIIQCLVT ETKTSVSRHI YFFSARGRID   240
PLVYLDEFLR NSEPVLKRVN RTGNSSSNKQ EYQLLKDNLV RSYNKALKKN APYPIFAIKN   300
GPKSHIGRHL MTSFLSMKGL TELTNVVGNW SDKRASAVAR TTYTHQITAI PDHYFALVSR   360
YYAYDPISKE MIALKDETNP IEEWQHIEQL KGSAEGSIRY PAWNGIISQE VLDYLSSYIN   420
RRI                                                                  423

SEQ ID NO: 3                 moltype = DNA   length = 1056
FEATURE                      Location/Qualifiers
misc_feature                 1..1056
                             note = iCre gene from pDIRE. ICre is a codon optimized
                              variant of Cre wt.
source                       1..1056
                             mol_type = other DNA
                             organism = synthetic construct
SEQUENCE: 3
atggtgccca agaagaagag gaaagtctcc aacctgctga ctgtgcacca aaacctgcct    60
gccctccctg tggatgccac ctctgatgaa gtcaggaaga acctgatgga catgttcagg   120
gacaggcagg cctttctcta acacacctgg aagatgctcc tgtctgtgtg cagatcctgg   180
gctgcctggt gcaagctgaa caacaggaaa tggttccctg ctgaacctga ggatgtgagg   240
gactacctcc tgtacctgca agccagaggc ctggctgtga agaccatcca acagcacctg   300
ggccagctca acatgctgca caggagatct ggcctgcctc gcccttctga ctccaatgct   360
gtgtccctgt gatgaggag aatcagaaag agaatgtgg atgctgggga gagagccaag   420
caggcccctg cctttgaacg cactgacttt gaccaagtca gatccctgac ggagaactgt   480
gacagatgcc aggacatcag gaacctggcc ttcctgggca ttgcctacaa caccctgctg   540
cgcattgccg aaattgccag aatcagagtc aaggacatct cccgcaccga tggtgggaga   600
atgctgatcc acattggcag gaccaagacc ctggtgtcca gctggtgt ggagaaggcc   660
ctgtccctgg gggttaccaa gctggtggag agatggatct ctgtgtctgg tgtggctgat   720
gaccccaaca actacctgtt ctgccgggtc agaaagaatg gtgtggctgc cccttctgcc   780
acctcccaac tgtccacccg ggccctgaa gggatctttg aggccaccca ccgcctgatc   840
tatggtgcca aggatgactc tgggcagaga tacctggcct ggtctggcca ctctgccaga   900
gtgggtgctg ccagggacat ggccagggct ggtgtgtcca tccctgaaat catgcaggct   960
ggtggctgga ccaatgtgaa cattgtgatg aactacatca gaaacctgga ctctgagact  1020
ggggccatgg tgaggctgct cgaggatggg gactga                            1056

SEQ ID NO: 4                 moltype = AA   length = 351
FEATURE                      Location/Qualifiers
REGION                       1..351
                             note = Amino acid sequence of iCre.
source                       1..351
                             mol_type = protein
                             organism = synthetic construct
SEQUENCE: 4
MVPKKKRKVS NLLTVHQNLP ALPVDATSDE VRKNLMDMFR DRQAFSEHTW KMLLSVCRSW    60
AAWCKLNNRK WFPAEPEDVR DYLLYLQARG LAVKTIQQHL GQLNMLHRRS GLPRPSDSNA   120
VSLVMRRIRK ENVDAGERAK QALAFERTFD DQVRSLMENS DRCQDIRNLA FLGIAYNTLL   180
RIAEIARIRV KDISRTDGGR MLIHIGRTKT LVSTAGVEKA LSLGVTKLVE RWISVSGVAD   240
DPNNYLFCRV RKNGVAAPSA TSQLSTRALE GIFEATHRLI YGAKDDSGQR YLAWSGHSAR   300
VGAARDMARA GVSIPEIMQA GGWTNVNIVM NYIRNLDSET GAMVRLLEDG D           351

SEQ ID NO: 5                 moltype = AA   length = 474
FEATURE                      Location/Qualifiers
source                       1..474
                             mol_type = protein
                             organism = Zygosaccharomyces bailii
SEQUENCE: 5
MSEFSELVRI LPLDQVAEIK RILSRGDPIP LQRLASLLTM VILTVNMSKK RKSSPIKLST    60
FTKYRRNVAK SLYYDMSSKT VFFEYHLKNT QDLQEGLEQA IAPYNFVVKV HKKPIDWQKQ   120
LSSVHERKAG HRSILSNNVG AEISKLAETK DSTWSFIERT MDLIEARTRQ PTTRVAYRFL   180
LQLTFMNCCR ANDLKNADPS TFQIIADPHL GRILRAFVPE TKTSIERFIY FFPCKGRCDP   240
LLALDSYLLW VGPVPKTQTT DEETQYDYQL LQDTLLISYD RFIAKESKEN IFKIPNGPKA   300
HLGRHLMASY LGNNSLKSEA TLYGNWSVER QEGVSKMADS RYMHTVKKSP PSYLFAFLSG   360
YYKKSNQGEY VLAETLYNPL DYDKTLPITT NEKLICRRYG KNAKVIPKDA LLYLYTYAQQ   420
KRKQLADPNE QNRLFSSESP AHPFLTPQST GSSTPLTWTA PKTLSTGLMT PGEE         474

SEQ ID NO: 6                 moltype = AA   length = 568
FEATURE                      Location/Qualifiers
source                       1..568
                             mol_type = protein
                             organism = Zygosaccharomyces rouxii
SEQUENCE: 6
MSSYMDLVDD EPATLYHKFV ECLKAGENFC GDKLSGIITM AILKAIKALT EVKKTTFNKY    60
KTTIKQGLQY DVGSSTISFV YHLKDCDELS RGLSDAFEPY KFKIKSNKEA TSFKTLFRGP   120
```

```
SFGSQKNWRK KEVDREVDNL FHSTETDESI FKFILNTLDS IETQTNTDRQ KTVLTFILLM   180
TFFNCCRNND LMNVDPSTFK IVKNKFVGYL LQAEVKQTKT RKSRNIFFFP IRENRFDLFL   240
ALHDFFRTCQ PTPKSRLSDQ VSEQKWQLFR DSMVIDYNRF FRKFPASPIF AIKHGPKSHL   300
GRHLMNSFLH KNELDSWANS LGNWSSSQNQ RESGARLGYT HGGRDLPQPL FGFLAGYCVR   360
NEEGHIVGLG LEKDINDLFD GIMDPLNEKE DTEICESYGE WAKIVSKDVL IFLKRYHSKN   420
ACRRYQNSTL YARTFLKTES VTLSGSKGSE EPSSPVRIPI LSMGKASPSE GRKLRASEHA   480
NDDNEIEKID SDSSQSEEIP IEMSDSEDET TASNISGIYL DMSKANSNVV YSPPSQTGRA   540
AGAGRKRGVG GRRTVESKRR RVLAPINR                                      568

SEQ ID NO: 7               moltype = AA   length = 447
FEATURE                    Location/Qualifiers
source                     1..447
                           mol_type = protein
                           organism = Kluyveromyces drosophilarum
SEQUENCE: 7
MSTFAEAAHL TPHQCANEIN EILESDTFNI NAKEIRNKLA SLFSILTMQS LSIRREMKIN    60
TYRSYKSAIG KSLSFDKDDK IIKFTVRLRK TESLQKDIES ALPSYKVVVS PFKNQEVSLF   120
DRYEETHKYD ASMVGLQFTN ILSKEKDIWK IVSRIACFFD QSCVTTTKRA EYRLLLLGAV   180
GNCCRYSDLK NLDPRTFEIY NNSFLGPIVR ATVTETKSRT ERYVNFYPVN GDCDLLISLY   240
DYLRVCSPIE KTVSSNRPTN QTHQFLPESL ARTFSRFLTQ HVDEPVFKIW NGPKSHFGRH   300
LMATFLSRSE KGKYVSSLGN WAGDREIQSA VARSHYSHGS VTVDDRVFAF ISGFYKEAPL   360
GSEIYVLKDP SNKPLSREEL LEEEGNSLGS PPLSPPSSPR LVAQSFSAHP SLQLFEQWHG   420
IISDEVLQFI AEYRRKHELR SQRTVVA                                       447

SEQ ID NO: 8               moltype = AA   length = 413
FEATURE                    Location/Qualifiers
source                     1..413
                           mol_type = protein
                           organism = Kluyveromyces waltii
SEQUENCE: 8
MSVFEELISK NLMSLMEELM SMLTNEKEFQ RERFASLLAY MIMATGELEE KKLSTFTKYS    60
RRIRQTVEFD SNNQIVRFEY HLKNPTELKE TLDKAFKPVV FEIKSKKKVV SMLELAAKLD   120
KRGSDSAGGT VASEVSKLVR EEEIWLLLVN VKNTIQEKVR KSSLRAELTY ILTASFFNCC   180
RHSDLRNADP ATFELVPNKY VGHVVRVLVC ETKTRKPRFI YFFPVNTAAD PLVALHDLFS   240
STFPSKKSRT SERKQEQEWQ IVRDASINNY DRFVGKHATE SVFAILHGPK SHLGRHLMSS   300
YLAYTHHGEW VSPYGNWSAG KGTIESSVAR AKYAHVQAEI PSDLFAFLSQ YYQESKSGDF   360
ELNDTSKDPT KLVRHSASQL EINRTYGPWS RLVNKDVLGF VHSYAMAKRY EGK          413

SEQ ID NO: 9               moltype = AA   length = 490
FEATURE                    Location/Qualifiers
source                     1..490
                           mol_type = protein
                           organism = Zygosaccharomyces rouxii
SEQUENCE: 9
MQLTKDTEIS TINRQMSDFS ELSQILPLHQ ISKIKDILEN ENPLPKEKLA SHLTMIILMA    60
NLASQKRKDV PVKRSTFLKY QRSISKTLQY DSSTKTVSFE YHLKDPSKLI KGLEDVVSPY   120
RFVVGVHEKP DDVMSHLSAV HMRKEAGRKR DLGNKINDEI TKIAETQETI WGFVGKTML    180
IEARTTRPTT KAAYNLLLQA TFMNCCRADD LKNTDIKTFE VIPDKHLGRM LRAFVPETKT   240
GTRFVYFFPC KGRCDPLLAL DSYLQWTDPI PKTRTTDEDA RYDYQLLRNS LLGSYDGFIS   300
KQSDESIFKI PNGPKAHLGR HVTASYLSNN EMDKEATLYG NWSAAREEGV SRVAKARYMH   360
TIEKSPPSYL FAFLSGFYNI TAERACELVD PNSNPCEQDK NIPMISDIET LMARYGKNAE   420
IIPMDVLVFL SSYARFKNNE GKEYKLQARS SRGVPDFPDN GRTALYNALT AAHVKRRKIS   480
IVVGRSIDTS                                                          490

SEQ ID NO: 10              moltype = AA   length = 414
FEATURE                    Location/Qualifiers
source                     1..414
                           mol_type = protein
                           organism = Zygosaccharomyces fermentati
SEQUENCE: 10
MSLFEELVSR NITSLVNELK EMLNSEHKLP SEKFASLLAY VIMATFSKLS ERKRSTFIKY    60
SREIRQSVQY DREAQIVKFN YHLKRPHELK DVLDKTFAPI VFEVSSTKKV ESMVELAAKM   120
DKVEGKGGHN AVAEEITKIV RADDIWTLLS GVEVTIQKRA FKRSLRAELK YVLITSFFNC   180
SRHSDLKNAD PTKFELVKNR YLNRVLRVLV CETKTRKPRY IYFFPVNKKT DPLIALHDLF   240
SEAEPVPKSR ASHQKTDQEW QMLRDSLLTN YDRFIATHAK QAVFGIKHGP KSHLGRHLMS   300
SYLSHTNHGQ WVSPFGNWSA GKDTVESNVA RAKYVHIQAD IPDELFAFLS QYYIQTPSGD   360
FELIDSSEQP TTFINNLSTQ EDISKSYGTW TQVVGQDVLE YVHSYAMGKL GIRK         414

SEQ ID NO: 11              moltype = AA   length = 427
FEATURE                    Location/Qualifiers
source                     1..427
                           mol_type = protein
                           organism = Torulaspora delbrueckii
SEQUENCE: 11
MSEFRKLLET NIEVTKQKIL EILCSGSLPQ HKDQFGAYMA MTILKYNALN GRSMEEAREI    60
KINTFKKYRS LIANTVTFRA DDNVSFKYH TGRMQDLNEQ LSAYFKDINF DIQSVRKTSM    120
DTVFSGKEIK IVKRSTKLEG SKLINEAFSK LVTLNMRLGH DIVVPMKSI  TDYTKSASTN   180
AEYSFMFLLT VYNCCRQSDL KNLDPETFEI IHNTFLGRMI RALVTDTKTR KARFIYFYPV   240
AGPHDPILAL HYLLCETKPK MKSLTSNIES DQQYQLLREN LVTQYDRFLA KRRPLGLFGI   300
```

```
THGPKSHFGR HLMTTYLSTH NLGELVTPFG NWCATDDLIS SKTARSNYGH RTQEIPDHLF    360
GFLSDFYRLE DGKYVLVDQQ RDPKMADRQL ECSTTYETPY GSWQELIKAE VLSFVWYYSQ    420
RRLQQAA                                                              427

SEQ ID NO: 12              moltype = DNA   length = 34
FEATURE                    Location/Qualifiers
misc_feature               1..34
                           note = Consensus recongition sequence for the wild-type
                            recombinase Flp.
source                     1..34
                           mol_type = other DNA
                           organism = synthetic construct
SEQUENCE: 12
gaagttccta tactttctag agaataggaa cttc                                34

SEQ ID NO: 13              moltype = DNA   length = 34
FEATURE                    Location/Qualifiers
source                     1..34
                           mol_type = other DNA
                           organism = Bacteriophage P1
SEQUENCE: 13
ataacttcgt ataatgtatg ctatacgaag ttat                                34

SEQ ID NO: 14              moltype = AA    length = 34
FEATURE                    Location/Qualifiers
REGION                     1..34
                           note = Consensus sequence of TAL DBD repeat.
source                     1..34
                           mol_type = protein
                           organism = synthetic construct
SEQUENCE: 14
LTPDQVVAIA SHDGGKQALE TVQRLLPVLC QDHG                                34

SEQ ID NO: 15              moltype = AA    length = 830
FEATURE                    Location/Qualifiers
REGION                     1..830
                           note = TAL-18 is a representative sequence of a TAL DBD.
source                     1..830
                           mol_type = protein
                           organism = synthetic construct
SEQUENCE: 15
MVDLRTLGYS QQQQEKIKPK VRSTVAQHHE ALVGHGFTHA HIVALSQHPA ALGTVAVTYQ    60
HIITALPEAT HEDIVGVGKQ WSGARALEAL LTDAGELRGP PLQLDTGQLV KIAKRGGVTA    120
MEAVHASRNA LTGAPLNLTP DQVVAIASNN GGKQALETVQ RLLPVLCQDH GLTPDQVVAI    180
ASHDGGKQAL ETVQRLLPVL CQDHGLTPDQ VVAIASNIGG KQALETVQRL LPVLCQDHGL    240
TPDQVVAIAS NGGGKQALET VQRLLPVLCQ DHGLTPDQVV AIASNIGGKQ ALETVQRLLP    300
VLCQDHGLTP DQVVAIASNG GGKQALETVQ RLLPVLCQDH GLTPDQVVAI ASNGGGKQAL    360
ETVQRLLPVL CQDHGLTPDQ VVAIASHDGG KQALETVQRL LPVLCQDHGL TPDQVVAIAS    420
NIGGKQALET VQRLLPVLCQ DHGLTPDQVV AIASNGGGKQ ALETVQRLLP VLCQDHGLTP    480
DQVVAIASNI GGKQALETVQ RLLPVLCQDH GLTPDQVVAI ASNIGGKQAL ETVQRLLPVL    540
CQDHGLTPDQ VVAIASNGGG KQALETVQRL LPVLCQDHGL TPDQVVAIAS HDGGKQALET    600
VQRLLPVLCQ DHGLTPDQVV AIASNGGGKQ ALETVQRLLP VLCQDHGLTP DQVVAIASHD    660
GGKQALETVQ RLLPVLCQDH GLTPDQVVAI ASHDGGKQAL ETVQRLLPVL CQDHGLTPDQ    720
VVAIASHDGG KQALESIVAQ LSRPDPALAA LTNDHLVALA CLGGRPAMDA VKKGLPHAPE    780
LIRRVNRRIG ERTSHRVADY AQVVRVLEFF QCHSHPAYAF DEAMTQFGMS               830

SEQ ID NO: 16              moltype = DNA   length = 34
FEATURE                    Location/Qualifiers
misc_feature               1..34
                           note = sequence of the genomic FRT-like sequence FL61.
                            Sequence arranced as Flp binding element-spacer-Flp
                            binding element.
source                     1..34
                           mol_type = other DNA
                           organism = synthetic construct
SEQUENCE: 16
catggtccaa gtctgataat agaaatggca ttgt                                34

SEQ ID NO: 17              moltype = DNA   length = 34
FEATURE                    Location/Qualifiers
misc_feature               1..34
                           note = Sequence of the genomic FRT-like sequence FL63.
                            Sequence is arranged as Flp binding element-spacer-Flp
                            binding element.
source                     1..34
                           mol_type = other DNA
                           organism = synthetic construct
SEQUENCE: 17
cacctgctaa ttctgcactt agaataatcc tttt                                34
```

```
SEQ ID NO: 18            moltype = DNA  length = 34
FEATURE                  Location/Qualifiers
misc_feature             1..34
                         note = Sequence of the geneomic FRT-like sequence FL71. The
                          sequence is arranged as Flp binding element-spacer-Flp
                          binding element.
source                   1..34
                         mol_type = other DNA
                         organism = synthetic construct
SEQUENCE: 18
cctagtacat tactatttgg aatatatgtg tgct                                    34

SEQ ID NO: 19            moltype = DNA  length = 75
FEATURE                  Location/Qualifiers
misc_feature             1..75
                         note = FL-61 and flanking TAL-targeted sequences
source                   1..75
                         mol_type = other DNA
                         organism = synthetic construct
SEQUENCE: 19
ttcacgactg acatcaccgt catggtccaa gtctgataat agaaatggca ttgtcacttt        60
cttccctact gcaac                                                        75

SEQ ID NO: 20            moltype = DNA  length = 76
FEATURE                  Location/Qualifiers
misc_feature             1..76
                         note = FL-63 and flanking TAL-targeted sequences
source                   1..76
                         mol_type = other DNA
                         organism = synthetic construct
SEQUENCE: 20
caaattatgc ataccagctc tcacctgcta attctgcact tagaataatc cttttgtctc        60
tccacatggg tatggg                                                       76

SEQ ID NO: 21            moltype = DNA  length = 84
FEATURE                  Location/Qualifiers
misc_feature             1..84
                         note = FL-71 and flanking TAL-target sequences;
                          (TAL/L24-TAL/R15)
source                   1..84
                         mol_type = other DNA
                         organism = synthetic construct
SEQUENCE: 21
gtaacttaaa aaaaaacttt acacagtctg cctagtacat tactatttgg aatatatgtg        60
tgcttatttg catattcata atct                                              84

SEQ ID NO: 22            moltype = DNA  length = 15
FEATURE                  Location/Qualifiers
misc_feature             1..15
                         note = FL-61_TAL(L) TAL DBD target sequence
source                   1..15
                         mol_type = other DNA
                         organism = synthetic construct
SEQUENCE: 22
gatgtcagtc gtgaa                                                        15

SEQ ID NO: 23            moltype = DNA  length = 15
FEATURE                  Location/Qualifiers
misc_feature             1..15
                         note = Sequence targeted by FL-61_TAL(R) TAL DBD.
source                   1..15
                         mol_type = other DNA
                         organism = synthetic construct
SEQUENCE: 23
cttccctact gcaac                                                        15

SEQ ID NO: 24            moltype = DNA  length = 15
FEATURE                  Location/Qualifiers
misc_feature             1..15
                         note = Sequence targeted by the FL-63_TAL(L) DBD.
source                   1..15
                         mol_type = other DNA
                         organism = synthetic construct
SEQUENCE: 24
ggtatgcata atttg                                                        15

SEQ ID NO: 25            moltype = DNA  length = 15
FEATURE                  Location/Qualifiers
```

```
misc_feature            1..15
                        note = Target sequence of the FL-63_TAL(R) TAL DBD
source                  1..15
                        mol_type = other DNA
                        organism = synthetic construct
SEQUENCE: 25
ccacatgggt atggg                                                            15

SEQ ID NO: 26           moltype = DNA  length = 24
FEATURE                 Location/Qualifiers
misc_feature            1..24
                        note = Target sequence of FL-71_TAL(L) TAL DBD
source                  1..24
                        mol_type = other DNA
                        organism = synthetic construct
SEQUENCE: 26
gtgtaaagtt tttttttaag ttac                                                  24

SEQ ID NO: 27           moltype = DNA  length = 15
FEATURE                 Location/Qualifiers
misc_feature            1..15
                        note = Target sequence for FL-71_TAL(R)
source                  1..15
                        mol_type = other DNA
                        organism = synthetic construct
SEQUENCE: 27
gcatattcat aatct                                                            15

SEQ ID NO: 28           moltype = AA  length = 496
FEATURE                 Location/Qualifiers
REGION                  1..496
                        note = Tandem repeats within the TAL DBD to bind to
                         GATGTCAGTCGTGAA.
source                  1..496
                        mol_type = protein
                        organism = synthetic construct
SEQUENCE: 28
LTPDQVVAIA SNNGGKQALE TVQRLLPVLC QDHGLTPDQV VAIASNIGGK QALETVQRLL   60
PVLCQDHGLT PDQVVAIASN GGGKQALETV QRLLPVLCQD HGLTPDQVVA IASNNGGKQA  120
LETVQRLLPV LCQDHGLTPD QVVAIASNGG KQALETVQR  LLPVLCQDHG LTPDQVVAIA  180
SHDGGKQALE TVQRLLPVLC QDHGLTPDQV VAIASNIGGK QALETVQRLL PVLCQDHGLT  240
PDQVVAIASN NGGKQALETV QRLLPVLCQD HGLTPDQVVA IASNGGGKQA LETVQRLLPV  300
LCQDHGLTPD QVVAIASHDG GKQALETVQR LLPVLCQDHG LTPDQVVAIA SNNGGKQALE  360
TVQRLLPVLC QDHGLTPDQV VAIASNGGGK QALETVQRLL PVLCQDHGLT PDQVVAIASN  420
NGGKQALETV QRLLPVLCQD HGLTPDQVVA IASNIGGKQA LETVQRLLPV LCQDHGLTPD  480
QVVAIASNIG GKQALE                                                 496

SEQ ID NO: 29           moltype = AA  length = 496
FEATURE                 Location/Qualifiers
REGION                  1..496
                        note = Tandem repeats within the FL-61_TAL(R) TAL DBD to
                         bind to CTTCCCTACTGCAAC
source                  1..496
                        mol_type = protein
                        organism = synthetic construct
SEQUENCE: 29
LTPDQVVAIA SHDGGKQALE TVQRLLPVLC QDHGLTPDQV VAIASNGGGK QALETVQRLL   60
PVLCQDHGLT PDQVVAIASN GGGKQALETV QRLLPVLCQD HGLTPDQVVA IASHDGGKQA  120
LETVQRLLPV LCQDHGLTPD QVVAIASHDG GKQALETVQR LLPVLCQDHG LTPDQVVAIA  180
SHDGGKQALE TVQRLLPVLC QDHGLTPDQV VAIASNGGGK QALETVQRLL PVLCQDHGLT  240
PDQVVAIASN IGGKQALETV QRLLPVLCQD HGLTPDQVVA IASHDGGKQA LETVQRLLPV  300
LCQDHGLTPD QVVAIASNGG GKQALETVQR LLPVLCQDHG LTPDQVVAIA SNNGGKQALE  360
TVQRLLPVLC QDHGLTPDQV VAIASHDGGK QALETVQRLL PVLCQDHGLT PDQVVAIASN  420
IGGKQALETV QRLLPVLCQD HGLTPDQVVA IASNIGGKQA LETVQRLLPV LCQDHGLTPD  480
QVVAIASHDG GKQALE                                                 496

SEQ ID NO: 30           moltype = AA  length = 496
FEATURE                 Location/Qualifiers
REGION                  1..496
                        note = Tandem repeats within the FL-63(TAL)(L) TAL DBD to
                         bind to GGTATGCATAATTTG
source                  1..496
                        mol_type = protein
                        organism = synthetic construct
SEQUENCE: 30
LTPDQVVAIA SNNGGKQALE TVQRLLPVLC QDHGLTPDQV VAIASNNGGK QALETVQRLL   60
PVLCQDHGLT PDQVVAIASN GGGKQALETV QRLLPVLCQD HGLTPDQVVA IASNIGGKQA  120
LETVQRLLPV LCQDHGLTPD QVVAIASNGG KQALETVQR  LLPVLCQDHG LTPDQVVAIA  180
SNNGGKQALE TVQRLLPVLC QDHGLTPDQV VAIASHDGGK QALETVQRLL PVLCQDHGLT  240
```

-continued

```
PDQVVAIASN IGGKQALETV QRLLPVLCQD HGLTPDQVVA IASNGGGKQA LETVQRLLPV    300
LCQDHGLTPD QVVAIASNIG GKQALETVQR LLPVLCQDHG LTPDQVVAIA SNIGGKQALE    360
TVQRLLPVLC QDHGLTPDQV VAIASNGGGK QALETVQRLL PVLCQDHGLT PDQVVAIASN    420
GGGKQALETV QRLLPVLCQD HGLTPDQVVA IASNGGGKQA LETVQRLLPV LCQDHGLTPD    480
QVVAIASNNG GKQALE                                                    496

SEQ ID NO: 31           moltype = AA  length = 496
FEATURE                 Location/Qualifiers
REGION                  1..496
                        note = Tandem repeats within the FL-63_TAL(R) TAL DBD to
                         bind to CCACATGGGTATGGG
source                  1..496
                        mol_type = protein
                        organism = synthetic construct
SEQUENCE: 31
LTPDQVVAIA SHDGGKQALE TVQRLLPVLC QDHGLTPDQV VAIASHDGGK QALETVQRLL    60
PVLCQDHGLT PDQVVAIASN IGGKQALETV QRLLPVLCQD HGLTPDQVVA IASHDGGKQA    120
LETVQRLLPV LCQDHGLTPD QVVAIASNIG GKQALETVQR LLPVLCQDHG LTPDQVVAIA    180
SNGGGKQALE TVQRLLPVLC QDHGLTPDQV VAIASNNGGK QALETVQRLL PVLCQDHGLT    240
PDQVVAIASN NGGKQALETV QRLLPVLCQD HGLTPDQVVA IASNNGGKQA LETVQRLLPV    300
LCQDHGLTPD QVVAIASNGG GKQALETVQR LLPVLCQDHG LTPDQVVAIA SNIGGKQALE    360
TVQRLLPVLC QDHGLTPDQV VAIASNGGGK QALETVQRLL PVLCQDHGLT PDQVVAIASN    420
NGGKQALETV QRLLPVLCQD HGLTPDQVVA IASNNGGKQA LETVQRLLPV LCQDHGLTPD    480
QVVAIASNNG GKQALE                                                    496

SEQ ID NO: 32           moltype = AA  length = 802
FEATURE                 Location/Qualifiers
REGION                  1..802
                        note = Tandem repeats within the FL-71_TAL(L) TAL DBD to
                         bind to GTGTAAAGTTTTTTTTAAGTTAC
source                  1..802
                        mol_type = protein
                        organism = synthetic construct
SEQUENCE: 32
LTPDQVVAIA SNNGGKQALE TVQRLLPVLC QDHGLTPDQV VAIASNGGGK QALETVQRLL    60
PVLCQDHGLT PDQVVAIASN NGGKQALETV QRLLPVLCQD HGLTPDQVVA IASNGGGKQA    120
LETVQRLLPV LCQDHGLTPD QVVAIASNIG GKQALETVQR LLPVLCQDHG LTPDQVVAIA    180
SNIGGKQALE TVQRLLPVLC QDHGLTPDQV VAIASNIGGK QALETVQRLL PVLCQDHGLT    240
PDQVVAIASN NGGKQALETV QRLLPVLCQD HGLTPDQVVA IASNGGGKQA LETVQRLLPV    300
LCQDHGLTPD QVVAIASNGG GKQALETVQR LLPVLCQDHG LTPDQVVAIA SNGGGKQALE    360
TVQRLLPVLC QDHGLTPDQV VAIASNGGGK QALETVQRLL PVLCQDHGLT PDQVVAIASN    420
GGGKQALETV QRLLPVLCQD HGLTPDQVVA IASNGGGKQA LETVQRLLPV LCQDHGLTPD    480
QVVAIASNGG GKQALETVQR LLPVLCQDHG LTPDQVVAIA SNGGGKQALE TVQRLLPVLC    540
QDHGLTPDQV VAIASNGGGK QALETVQRLL PVLCQDHGLT PDQVVAIASN IGGKQALETV    600
QRLLPVLCQD HGLTPDQVVA IASNIGGKQA LETVQRLLPV LCQDHGLTPD QVVAIASNNG    660
GKQALETVQR LLPVLCQDHG LTPDQVVAIA SNGGGKQALE TVQRLLPVLC QDHGLTPDQV    720
VAIASNGGGK QALETVQRLL PVLCQDHGLT PDQVVAIASN IGGKQALETV QRLLPVLCQD    780
HGLTPDQVVA IASHDGGKQA LE                                             802

SEQ ID NO: 33           moltype = AA  length = 496
FEATURE                 Location/Qualifiers
REGION                  1..496
                        note = Tandem repeats within the FL71_TAL(R) TAL DBD to
                         bind to GCATATTCATAATCT
source                  1..496
                        mol_type = protein
                        organism = synthetic construct
SEQUENCE: 33
LTPDQVVAIA SNNGGKQALE TVQRLLPVLC QDHGLTPDQV VAIASHDGGK QALETVQRLL    60
PVLCQDHGLT PDQVVAIASN IGGKQALETV QRLLPVLCQD HGLTPDQVVA IASNGGGKQA    120
LETVQRLLPV LCQDHGLTPD QVVAIASNIG GKQALETVQR LLPVLCQDHG LTPDQVVAIA    180
SNGGGKQALE TVQRLLPVLC QDHGLTPDQV VAIASNGGGK QALETVQRLL PVLCQDHGLT    240
PDQVVAIASH DGGKQALETV QRLLPVLCQD HGLTPDQVVA IASNIGGKQA LETVQRLLPV    300
LCQDHGLTPD QVVAIASNGG GKQALETVQR LLPVLCQDHG LTPDQVVAIA SNIGGKQALE    360
TVQRLLPVLC QDHGLTPDQV VAIASNIGGK QALETVQRLL PVLCQDHGLT PDQVVAIASN    420
GGGKQALETV QRLLPVLCQD HGLTPDQVVA IASHDGGKQA LETVQRLLPV LCQDHGLTPD    480
QVVAIASNGG GKQALE                                                    496

SEQ ID NO: 34           moltype = DNA  length = 191
FEATURE                 Location/Qualifiers
misc_feature            1..191
                        note = Outer FRT; the EM-7 promoter is located before the
                         recombination site.
source                  1..191
                        mol_type = other DNA
                        organism = synthetic construct
SEQUENCE: 34
catcggcata gtatatcggc atagtataat acgacaaggt gaggaactaa acccctattc    60
ttgtgttcac gactgacatc accgtgaagt tcctatactg ataatagaaa tggcattgtc    120
```

```
actttcttcc ctactgcaac agaagcccag ctcttcccct tgaaaaacac gatgataata   180
tggccacaac c                                                        191

SEQ ID NO: 35           moltype = DNA  length = 180
FEATURE                 Location/Qualifiers
misc_feature            1..180
                        note = Outer FRT; the EM-7 promoter is located before the
                         recombination site.
source                  1..180
                        mol_type = other DNA
                        organism = synthetic construct
SEQUENCE: 35
catcggcata gtatatcggc atagtataat acgacaaggt gaggaactaa accacaactc   60
aaattatgca taccagctct gaagttccta tactgcactt agaataatcc ttttgtctct   120
ccacatgggt atgggagagg ccttcccttt gaaaaacacg atgataatat ggccacaacc   180

SEQ ID NO: 36           moltype = DNA  length = 201
FEATURE                 Location/Qualifiers
misc_feature            1..201
                        note = Outer FRT site; the lacIQ promoter is located before
                         the recombination site.
source                  1..201
                        mol_type = other DNA
                        organism = synthetic construct
SEQUENCE: 36
gactcactat agggagaccc aagctggcta ggtggtgcaa aacctttcgc ggtatggcat   60
gatagcgccc ggaagagagt caattcaggg agatacatta gtaacttaa aaaaaaactt    120
tacacagtct gcctagtaca ttactatttg gagtatagga acttctattt gcatattcat   180
aatctcccta ctttatttc t                                              201

SEQ ID NO: 37           moltype = AA   length = 1277
FEATURE                 Location/Qualifiers
REGION                  1..1277
                        note = 71-18_TLA is an aa sequence of a representative
                         chimeric Fl-TAL recombinase.
source                  1..1277
                        mol_type = protein
                        organism = synthetic construct
SEQUENCE: 37
MSQFDILCKT PPKVLVRQFV ERFERPSGEK IASCTAELTY LCWVVTHNGA AIKRSTFVNY    60
NSIISNSLSF DIVNKSLQFK YKTQKATILE ASLKKLIPAW EFTIIPYNGQ KHQPDITDIV    120
SSLQLQFESP EEADKGNSHS KKMLKALLSE GESIWEITEK ILNSFEYTSR STKTKALYQF    180
LFLATFINCG RFSDIKNVDP KSFKLVQNKY LGEIIQCLVT ETKTSVSRHI YFFSARGRID   240
PLVYLDEFLR NSEPVLKRVN RTGNSSSNKQ EYQLLKDNLV RSYNKALKKS APYPFFAIKN   300
GPKSHIGRHL MTSFLSMKGL TELTNVVGNW SDKRASAVAR TTYTHQITAI PDHYFALVSR   360
YYEYDPISKE MIALKDETNP IEEWQHIEQL KGSAEGSIRY PAWNGIISQE VLDYLSSYIN   420
RRIGTGSGGS GGSGGSGTSV DLRTLGYSQQ QQEKIKPKVR STVAQHHEAL VGHGFTHAHI   480
VALSQHPAAL GTVAVTYQHI ITALPEATHE DIVGVGKQWS GARALEALLT DAGELRGPPL   540
QLDTGQLVKI AKRGGVTAME AVHASRNALT GAPLNLTPDQ VVAIASNNGG KQALETVQRL   600
LPVLCQDHGL TPDQVVAIAS HDGGKQALET VQRLLPVLCQ DHGLTPDQVV AIASNIGGKQ   660
ALETVQRLLP VLCQDHGLTP DQVVAIASNG GGKQALETVQ RLLPVLCQDH GLTPDQVVAI   720
ASNIGGKQAL ETVQRLLPVL CQDHGLTPDQ VVAIASNGGG KQALETVQRL LPVLCQDHGL   780
TPDQVVAIAS NGGGKQALET VQRLLPVLCQ DHGLTPDQVV AIASHDGGKQ ALETVQRLLP   840
VLCQDHGLTP DQVVAIASNI GGKQALETVQ RLLPVLCQDH GLTPDQVVAI ASNGGGKQAL   900
ETVQRLLPVL CQDHGLTPDQ VVAIASNIGG KQALETVQRL LPVLCQDHGL TPDQVVAIAS   960
NIGGKQALET VQRLLPVLCQ DHGLTPDQVV AIASNGGGKQ ALETVQRLLP VLCQDHGLTP   1020
DQVVAIASHD GGKQALETVQ RLLPVLCQDH GLTPDQVVAI ASNGGGKQAL ETVQRLLPVL   1080
CQDHGLTPDQ VVAIASHDGG KQALETVQRL LPVLCQDHGL TPDQVVAIAS HDGGKQALET   1140
VQRLLPVLCQ DHGLTPDQVV AIASHDGGKQ ALESIVAQLS RPDPALAALT NDHLVALACL   1200
GGRPAMDAVK KGLPHAPELI RRVNRRIGER TSHRVADYAQ VVRVLEFFQC HSHPAYAFDE   1260
AMTQFGMSGP PKKKRKV                                                  1277

SEQ ID NO: 38           moltype = DNA  length = 1056
FEATURE                 Location/Qualifiers
misc_feature            1..1056
                        note = Coding sequence of iCreM24.
source                  1..1056
                        mol_type = other DNA
                        organism = synthetic construct
SEQUENCE: 38
atggtgccca agaagaagag gaaagtctcc aacctgctga ctgtgcacca aaacctgcct   60
gccctccctg tggatgccac ctctgatgaa gtcatgaaga acctgatgga catgttcagg   120
gacaggcagg ccttctctga acacacctgg aagatgctcc tgtctgtgtg cagatcctgg   180
gctgcctgtc gcaagtgaa caacaggaaa tggttcccgg ctgaacctga ggatgtgagg   240
gactacctcc tgtacctgca agccagaggc ctggctgtga agaccatcca acagcacctg   300
ggccagctca acatgctgca caggagatct ggcctgcctc gccttctga ctccaatgct   360
gtgtccctgg tgatgaggag aatcagaaag gagaatgtgg atgctgggga gagagccaag   420
caggccctgg cctttgaacg cactgacttt gaccaagtca gatcctgat ggagaactct   480
gacagatgcc aggacatcag gaacctggcc ttcctgggca ttgcctacaa caccctgctg   540
```

```
cgcattgccg aaaattgccag aatcagagtg aaggacatct cccgcaccga tggtgggaga    600
atgctgatcc acattggcag gaccaagacc ctggtgtcca cagctggtgt ggagaaggcc    660
ctgtccctgg gggttaccaa gctggtggag agatggatct ctgtgtctgg tgtggctgat    720
gaccccaaca actacctgtt ctgccgggtc agaaagaatg gtgtggctgc ccttctgcc    780
acctccaaac tgtccacccg ggccctgaa gggatcttcg aggcaccca ccgcctgatc    840
tatggtgcca aggatgactc tgggcagaga tacctggcct ggtctggcca ctctgccaga    900
gtgggtgctg ccaggacat ggccagggct ggtgtgtcca tccctgaaat catgcaggct    960
ggtggctgga ccaatgtgaa cattgtgatg aactacatca gaaacctgga ctctgagact   1020
ggggccatgt gaggctgct cgaggatggg gactga                              1056

SEQ ID NO: 39         moltype = AA  length = 351
FEATURE               Location/Qualifiers
REGION                1..351
                      note = aa sequence of iCreM24.
source                1..351
                      mol_type = protein
                      organism = synthetic construct
SEQUENCE: 39
MVPKKKRKVS NLLTVHQNLP ALPVDATSDE VMKNLMDMFR DRQAFSEHTW KMLLSVCRSW     60
AAWCKLNNRK WFPAEPEDVR DYLLYLQARG LAVKTIQQHL GQLNMLHRRS GLPRPSDSNA    120
VSLVMRRIRK ENVDAGERAK QALAFERTDF DQVRSLMENS DRCQDIRNLA FLGIAYNTLL    180
RIAEIARIRV KDISRTDGGR MLIHIGRTKT LVSTAGVEAL LSLGVTKLVE RWISVSGVAD    240
DPNNYLFCRV RKNGVAAPSA TSQLSTRALE GIFEATHRLI YGAKDDSGQR YLAWSGHSAR    300
VGAARDMARA GVSIPEIMQA GGWTNVNIVM NYIRNLDSET GAMVRLLEDG D             351

SEQ ID NO: 40         moltype = DNA  length = 1385
FEATURE               Location/Qualifiers
misc_feature          1..1385
                      note = iCreM24-TAL partial coding sequence
source                1..1385
                      mol_type = other DNA
                      organism = synthetic construct
SEQUENCE: 40
atggtgccca agaagaagag gaaagtctcc aacctgctga ctgtgcacca aaacctgcct     60
gccctccctg tggatgccac ctctgatgaa gtcatgaaga acctgatgga catgttcagg    120
gacaggcagg ccttctctga acacacctgg aagatgctcc tgtctgtgtg cagatcctgg    180
gctgcctggt gcaagctgaa caacaggaaa tggttccctg ctgaacctga ggatgtgagg    240
gactacctca tgtacctgca agccagaggc ctggctgtga gaccatcca acagcacctg    300
ggccagctca acatgctgca caggagatct ggcctgcctc gccttctga ctccaatgct    360
gtgtccctgg tgatgaggag aatcagaaag gagaatgtgg atgctgggga gagagccaag    420
caggccctgg cctttgaacg cactgacttt gaccaagtca gatcccctgat ggagaactct    480
gacagatgcc aggacatcag gaacctggcc ttcctgggca ttgcctacaa caccctgctg    540
cgcattgccg aaaattgccag aatcagagtg aaggacatct cccgcaccga tggtgggaga    600
atgctgatcc acattggcag gaccaagacc ctggtgtcca cagctggtgt ggagaaggcc    660
ctgtccctgg gggttaccaa gctggtggag agatggatct ctgtgtctgg tgtggctgat    720
gaccccaaca actacctgtt ctgccgggtc agaaagaatg gtgtggctgc ccttctgcc    780
acctccaaac tgtccacccg ggccctgaa gggatcttcg aggcaccca ccgcctgatc    840
tatggtgcca aggatgactc tgggcagaga tacctggcct ggtctggcca ctctgccaga    900
gtgggtgctg ccaggacat ggccagggct ggtgtgtcca tccctgaaat catgcaggct    960
ggtggctgga ccaatgtgaa cattgtgatg aactacatca gaaacctgga ctctgagact   1020
ggggccatgt gaggctgct cgaggatggg gactga ccgtaccg gatcaggcgg aagcggaccg  1080
catacagcgg ctgccccagc agagtgggat gaggcgcaat cggctctgcg tgcagccgat   1140
gacccgccac ccaccgtgcg tgtcgctgtc actgccgcgc ggccgccgcg cgccaagccg   1200
gccccgcgac ggcgtgctgc gcaacccctc gacgcttcgc cggccgcgca ggtggatcta   1260
cgcacgctcg gctacagtca gcagcagcaa gagaagatca aaccgaaagg tgcgttcgac   1320
agtggcgcag caccacgagg cactggtggg ccatgggttt acacacgcgc acatcgttgc   1380
gctca                                                               1385

SEQ ID NO: 41         moltype = DNA  length = 71
FEATURE               Location/Qualifiers
misc_feature          1..71
                      note = loxP-like sequence 69058 (LL-69) with flanking
                      sequences for TAL binding
source                1..71
                      mol_type = other DNA
                      organism = synthetic construct
SEQUENCE: 41
aaataagaaa tttgtaaatt tccttctgat aactagaaat agaggatcca gtttcttttg     60
gttaacctaa a                                                          71

SEQ ID NO: 42         moltype = DNA  length = 80
FEATURE               Location/Qualifiers
misc_feature          1..80
                      note = loxP-like sequence 69058 (LL-69) with flanking
                      sequences for TAL binding
source                1..80
                      mol_type = other DNA
                      organism = synthetic construct
SEQUENCE: 42
```

```
caatggaaat aagaaatttg taaatttcct tctgataact agaaatagag gatccagttt    60
cttttggtta acctaaattt                                                80

SEQ ID NO: 43          moltype = DNA   length = 77
FEATURE                Location/Qualifiers
misc_feature           1..77
                       note = loxP-like sequence 69058 (LL-69) with flanking
                         sequences for TAL binding
source                 1..77
                       mol_type = other DNA
                       organism = synthetic construct
SEQUENCE: 43
caatggaaat aagaaatttg taaatttcct tctgataact agaaatagag gatccagttt    60
cttttggtta acctaaa                                                   77

SEQ ID NO: 44          moltype = DNA   length = 78
FEATURE                Location/Qualifiers
misc_feature           1..78
                       note = FL-71, left TAL sequences of different lengths
                         (TAL/L18-TAL/R15)
source                 1..78
                       mol_type = other DNA
                       organism = synthetic construct
SEQUENCE: 44
taaaaaaaaa ctttcacacag tctgcctagt acattactat ttggagtata ggaacttcta   60
tttgcatatt cataatct                                                  78

SEQ ID NO: 45          moltype = DNA   length = 75
FEATURE                Location/Qualifiers
misc_feature           1..75
                       note = FL-71, left TAL seqences of different lengths
                         (TAL/L15-TAL/R15)
source                 1..75
                       mol_type = other DNA
                       organism = synthetic construct
SEQUENCE: 45
aaaaaaactt tacacagtct gcctagtaca ttactatttg gagtatagga acttctattt    60
gcatattcat aatct                                                     75

SEQ ID NO: 46          moltype = DNA   length = 34
FEATURE                Location/Qualifiers
misc_feature           1..34
                       note = Lox-like sequence 69058 (LL-69)
source                 1..34
                       mol_type = other DNA
                       organism = synthetic construct
SEQUENCE: 46
tttccttctg ataactagaa atagaggatc cagt                                34

SEQ ID NO: 47          moltype = DNA   length = 34
FEATURE                Location/Qualifiers
misc_feature           1..34
                       note = Consensus FRT sequence
source                 1..34
                       mol_type = other DNA
                       organism = synthetic construct
SEQUENCE: 47
gaagttccta twctttctag agwataggaa cttc                                34

SEQ ID NO: 48          moltype = DNA   length = 46
FEATURE                Location/Qualifiers
misc_feature           1..46
                       note = Sequencing of integration-specific PCR product LJ of
                         pTarget integrated into FL-61
source                 1..46
                       mol_type = other DNA
                       organism = synthetic construct
SEQUENCE: 48
caccgtcatg gtccaagtct gataatagaa atggcattgt cacttt                   46

SEQ ID NO: 49          moltype = DNA   length = 46
FEATURE                Location/Qualifiers
misc_feature           1..46
                       note = Sequencing of integration-specific PCR product RJ of
                         pTarget integrated into FL-61
source                 1..46
                       mol_type = other DNA
                       organism = synthetic construct
SEQUENCE: 49
```

-continued

```
caccgtgaag ttcctatact gataatagaa atggcattgt cacttt            46

SEQ ID NO: 50           moltype = DNA  length = 46
FEATURE                 Location/Qualifiers
misc_feature            1..46
                        note = Sequencing of integration-specific PCR product LJ of
                         pTarget integrated into FL-63
source                  1..46
                        mol_type = other DNA
                        organism = synthetic construct
SEQUENCE: 50
agctctcacc tgctaattct gcacttagaa taatccttt gtctct             46

SEQ ID NO: 51           moltype = DNA  length = 46
FEATURE                 Location/Qualifiers
misc_feature            1..46
                        note = Sequencing of integration-specific PCR product RJ of
                         pTarget integrated into FL-63
source                  1..46
                        mol_type = other DNA
                        organism = synthetic construct
SEQUENCE: 51
agctctgaag ttcctatact gcacttagaa taatccttt gtctct             46

SEQ ID NO: 52           moltype = DNA  length = 46
FEATURE                 Location/Qualifiers
misc_feature            1..46
                        note = Sequencing of integration-specific PCR product LJ of
                         pTarget integrated into FL-71
source                  1..46
                        mol_type = other DNA
                        organism = synthetic construct
SEQUENCE: 52
agtctgccta gtacattact atttggagta taggaacttc tatttg            46

SEQ ID NO: 53           moltype = DNA  length = 46
FEATURE                 Location/Qualifiers
misc_feature            1..46
                        note = Sequencing of integration-specific PCR product RJ of
                         pTarget integrated into FL-71
source                  1..46
                        mol_type = other DNA
                        organism = synthetic construct
SEQUENCE: 53
agtctgccta gtacattact atttggaata tatgtgtgct tatttg            46

SEQ ID NO: 54           moltype = DNA  length = 37
FEATURE                 Location/Qualifiers
misc_feature            1..37
                        note = Genome scanner sequence file
source                  1..37
                        mol_type = other DNA
                        organism = synthetic construct
SEQUENCE: 54
gatgcattcc tgttttgtaa tgattttcgg aaatttc                      37

SEQ ID NO: 55           moltype = DNA  length = 37
FEATURE                 Location/Qualifiers
misc_feature            1..37
                        note = Genome Scanner sequence
source                  1..37
                        mol_type = other DNA
                        organism = synthetic construct
SEQUENCE: 55
atgcattcct gttttgtaat gattttcgga aatttcg                      37

SEQ ID NO: 56           moltype = DNA  length = 37
FEATURE                 Location/Qualifiers
misc_feature            1..37
                        note = Genome Scanner sequence
source                  1..37
                        mol_type = other DNA
                        organism = synthetic construct
SEQUENCE: 56
tgcattcctg ttttgtaatg attttcggaa atttcgt                      37

SEQ ID NO: 57           moltype = DNA  length = 34
FEATURE                 Location/Qualifiers
misc_feature            1..34
```

```
                    note = Genome Scanner sequence
source              1..34
                    mol_type = other DNA
                    organism = synthetic construct
SEQUENCE: 57
attgtttctt ttattcgtac agtaaatgat tatt                              34

SEQ ID NO: 58       moltype = DNA  length = 34
FEATURE             Location/Qualifiers
misc_feature        1..34
                    note = Genome Scanner sequence
source              1..34
                    mol_type = other DNA
                    organism = synthetic construct
SEQUENCE: 58
tgcattcctg ttttgtaatg attttcggaa attt                              34

SEQ ID NO: 59       moltype = DNA  length = 34
FEATURE             Location/Qualifiers
misc_feature        1..34
                    note = Genome Scanner sequence
source              1..34
                    mol_type = other DNA
                    organism = synthetic construct
SEQUENCE: 59
atagtttctt tgttgagaag actatatgag gaac                              34

SEQ ID NO: 60       moltype = DNA  length = 34
FEATURE             Location/Qualifiers
misc_feature        1..34
                    note = Genome Scanner sequence
source              1..34
                    mol_type = other DNA
                    organism = synthetic construct
SEQUENCE: 60
attttattta ttttaattttt aaaatttggt ttta                             34

SEQ ID NO: 61       moltype = DNA  length = 34
FEATURE             Location/Qualifiers
misc_feature        1..34
                    note = SpacerSorter sequence
source              1..34
                    mol_type = other DNA
                    organism = synthetic construct
SEQUENCE: 61
gatttacata tattagcaat aaaagcagag caaa                              34

SEQ ID NO: 62       moltype = DNA  length = 34
FEATURE             Location/Qualifiers
misc_feature        1..34
                    note = SpacerSorter sequence
source              1..34
                    mol_type = other DNA
                    organism = synthetic construct
SEQUENCE: 62
cagtggccca tattagcaat aaaagttgag ttag                              34

SEQ ID NO: 63       moltype = DNA  length = 34
FEATURE             Location/Qualifiers
misc_feature        1..34
                    note = SpacerSorter sequence
source              1..34
                    mol_type = other DNA
                    organism = synthetic construct
SEQUENCE: 63
attttacatc ttttagcaat aatataaaac attg                              34

SEQ ID NO: 64       moltype = DNA  length = 34
FEATURE             Location/Qualifiers
misc_feature        1..34
                    note = SpacerSorter sequence
source              1..34
                    mol_type = other DNA
                    organism = synthetic construct
SEQUENCE: 64
tatagatctc ttttattgct aatatatgtt tcct                              34

SEQ ID NO: 65       moltype = DNA  length = 34
FEATURE             Location/Qualifiers
```

```
misc_feature               1..34
                           note = SpacerSorter sequence
source                     1..34
                           mol_type = other DNA
                           organism = synthetic construct
SEQUENCE: 65
gtgtcacctc ttttattgct aatattggta attt                             34

SEQ ID NO: 66              moltype = DNA  length = 34
FEATURE                    Location/Qualifiers
misc_feature               1..34
                           note = SpacerSorter sequence
source                     1..34
                           mol_type = other DNA
                           organism = synthetic construct
SEQUENCE: 66
ttcaaaccca tattgaagcc aaaagattaa gggt                             34

SEQ ID NO: 67              moltype = DNA  length = 34
FEATURE                    Location/Qualifiers
misc_feature               1..34
                           note = SpacerSorter sequence
source                     1..34
                           mol_type = other DNA
                           organism = synthetic construct
SEQUENCE: 67
cttgtggctc ttttggcttc aatattcgct tggc                             34

SEQ ID NO: 68              moltype = DNA  length = 34
FEATURE                    Location/Qualifiers
misc_feature               1..34
                           note = SpacerSorter sequence
source                     1..34
                           mol_type = other DNA
                           organism = synthetic construct
SEQUENCE: 68
tgccttctta tattaataag aaaagtaaaa caaa                             34

SEQ ID NO: 69              moltype = DNA  length = 34
FEATURE                    Location/Qualifiers
misc_feature               1..34
                           note = SpacerSorter sequence
source                     1..34
                           mol_type = other DNA
                           organism = synthetic construct
SEQUENCE: 69
ttttctattc ttttaataag aatatttgac ttaa                             34

SEQ ID NO: 70              moltype = DNA  length = 34
FEATURE                    Location/Qualifiers
misc_feature               1..34
                           note = SpacerSorter sequence
source                     1..34
                           mol_type = other DNA
                           organism = synthetic construct
SEQUENCE: 70
tctggttttc ttttactggg aatatcagga attt                             34

SEQ ID NO: 71              moltype = DNA  length = 34
FEATURE                    Location/Qualifiers
misc_feature               1..34
                           note = SpacerSorter sequence
source                     1..34
                           mol_type = other DNA
                           organism = synthetic construct
SEQUENCE: 71
catttccttc ttttatctgc aatataagaa ggaa                             34

SEQ ID NO: 72              moltype = DNA  length = 34
FEATURE                    Location/Qualifiers
misc_feature               1..34
                           note = SpacerSorter sequence
source                     1..34
                           mol_type = other DNA
                           organism = synthetic construct
SEQUENCE: 72
catgtcagga tatttcctat aaaaggagag acaa                             34

SEQ ID NO: 73              moltype = DNA  length = 34
```

```
FEATURE              Location/Qualifiers
misc_feature         1..34
                     note = SpacerSorter sequence
source               1..34
                     mol_type = other DNA
                     organism = synthetic construct
SEQUENCE: 73
cttaatccac ttttaactgc aatatagcat tctg                              34
```